US011045543B2

United States Patent
Yu et al.

(10) Patent No.: US 11,045,543 B2
(45) Date of Patent: Jun. 29, 2021

(54) EGFR-DIRECTED CAR THERAPY FOR GLIOBLASTOMA

(71) Applicant: CYTOIMMUNE THERAPEUTICS, INC., Wilmington, DE (US)

(72) Inventors: Jianhua Yu, Columbus, OH (US); Michael Caligiuri, Columbus, OH (US)

(73) Assignee: CYTOIMMUNE THERAPEUTICS, INC., Wilmington, DE (US)

( * ) Notice: Subject to any disclaimer, the term of this patent is extended or adjusted under 35 U.S.C. 154(b) by 55 days.

(21) Appl. No.: 15/564,166

(22) PCT Filed: Apr. 5, 2016

(86) PCT No.: PCT/US2016/026057
§ 371 (c)(1),
(2) Date: Oct. 3, 2017

(87) PCT Pub. No.: WO2016/164370
PCT Pub. Date: Oct. 13, 2016

(65) Prior Publication Data
US 2018/0117146 A1   May 3, 2018

Related U.S. Application Data

(60) Provisional application No. 62/143,744, filed on Apr. 6, 2015.

(51) Int. Cl.
| C07K 16/28  | (2006.01) |
| A61K 39/395 | (2006.01) |
| C07K 14/725 | (2006.01) |
| C07K 14/705 | (2006.01) |
| A61P 35/00  | (2006.01) |
| A61K 39/00  | (2006.01) |
| C07K 16/30  | (2006.01) |

(52) U.S. Cl.
CPC .... *A61K 39/395* (2013.01); *A61K 39/001104* (2018.08); *A61P 35/00* (2018.01); *C07K 14/7051* (2013.01); *C07K 14/70521* (2013.01); *C07K 16/2863* (2013.01); *C07K 16/30* (2013.01); *A61K 2039/5156* (2013.01); *A61K 2039/5158* (2013.01); *A61K 2039/80* (2018.08); *C07K 2317/622* (2013.01); *C07K 2319/03* (2013.01); *C07K 2319/33* (2013.01); *C12N 2740/15043* (2013.01)

(58) Field of Classification Search
None
See application file for complete search history.

(56) References Cited

U.S. PATENT DOCUMENTS

| 2004/0038339 A1 | 2/2004  | Kufer et al.     |
| 2006/0210564 A1 | 9/2006  | Kumagai et al.   |
| 2009/0155275 A1 | 6/2009  | Wu et al.        |
| 2011/0052570 A1 | 3/2011  | Klagsbrun et al. |
| 2012/0034245 A9 | 2/2012  | Thompson et al.  |
| 2012/0148552 A1 | 6/2012  | Jensen           |
| 2013/0280285 A1 | 10/2013 | Schonfeld et al. |
| 2014/0037628 A1 | 2/2014  | Morgan et al.    |
| 2014/0242701 A1 | 8/2014  | Shiku et al.     |
| 2014/0294834 A1 | 10/2014 | Harms et al.     |
| 2014/0302037 A1 | 10/2014 | Borges et al.    |
| 2014/0314667 A1 | 10/2014 | Hill et al.      |
| 2015/0005477 A1* | 1/2015 | Lowman ........... A61K 47/6889 530/391.5 |
| 2015/0017141 A1 | 1/2015  | June et al.      |
| 2015/0038684 A1 | 2/2015  | Jensen           |
| 2015/0307564 A1 | 10/2015 | Young et al.     |
| 2016/0046724 A1 | 2/2016  | Brogdon et al.   |
| 2016/0331793 A1 | 11/2016 | Champion et al.  |
| 2018/0237519 A1 | 8/2018  | Caligiuri et al. |

FOREIGN PATENT DOCUMENTS

| CN | 103113470 A      | 5/2013  |
| JP | 2005-521398 A    | 7/2005  |
| JP | 2005333993 A *   | 12/2005 |
| WO | WO-2012/079000 A1 | 6/2012 |
| WO | WO-2014/138704 A1 | 9/2014 |
| WO | WO-2014/179759 A1 | 11/2014 |
| WO | WO-2015/142675 A2 | 9/2015 |
| WO | WO-2016/154585 A1 | 9/2016 |
| WO | WO-2017/079705 A1 | 5/2017 |
| WO | WO-2018/039247 A1 | 3/2018 |

OTHER PUBLICATIONS

Mariuzza et al. (Annu. Rev. Biophys. Biophys. Chem., 16: 139-159, 1987).*
Edwards etal (J Mol Biol, 14;334(1):103-118, 2003).*
Lloyd etal (Protein Engineering, Design & Selection, 22:159-168, 2009).*
Hayashi etal (CII, 53:497-509, 2004).*
Suzuki etal (PBC, 62:1326-1336, Apr. 1, 2015).*
International Search Report and Written Opinion (ISA/US) for International Application No. PCT/US2016/026057, dated Aug. 12, 2016.
International Preliminary Report on Patentability on International Application No. PCT/US2016/026057 dated Oct. 19, 2017, 8 pages.
Caruana, Iganzio, Iulia Diaconu, and Gianpietro Dotti. "From monoclonal antibodies to chimeric antigen receptors for the treatment of human malignancies." Seminars in oncology. vol. 41. No. 5. Elsevier, 2014, pp. 661-666.

(Continued)

*Primary Examiner* — Brad Duffy
(74) *Attorney, Agent, or Firm* — Foley & Lardner LLP

(57) ABSTRACT

Glioblastoma (GB) remains the most aggressive primary brain malignancy; brain metastasis, such as breast cancer brain metastases (BCBMs), are also aggressive and are associated with poor prognosis. Adoptive transfer of chimeric antigen receptor (CAR)-modified immune cells has emerged as a promising anti-cancer approach, yet the potential utility of CAR-engineered cells to treat brain cancers has not been explored. The present disclosure presents compositions and methods for using CAR expressing cells in the treatment of various cancers, including brain cancers such as GB and BCBMs.

33 Claims, 24 Drawing Sheets

Specification includes a Sequence Listing.

(56) References Cited

OTHER PUBLICATIONS

Hillary G. Caruso, "Car-Modified Cells Capable of Distinguishing Normal Cells from Malignant Cells", UT GSBS Dissertations and Theses (Open Access), May 1, 2014, 1-205.

Nishiyama et al., "Oncolytic Virotherapy using Replication-Competent Herpes Simplex Viruses", Virus, vol. 57, No. 1, 2007, pp. 57-66.Nishiyama et al., "Oncolytic Virotherapy using Replication-Competent Herpes Simplex Viruses", Virus, vol. 57, No. 1, 2007, pp. 57-66 (English Translation).

Schuster, et al., "A phase II, multicenter trial of rindopepimut (CDX-110) in newly diagnosed glioblastoma: the ACT III study", Neuro-Oncology 17(6), 854-861, 2015.

Chen, X. et al. (2016) "A combinational therapy of EGFR-CAR NK cells and oncolytic herpes simplex virus 1 for breast cancer brain metastases," Oncotarget 7(19):27764-27777.

Congdon, K.L. et al. (2014) "Epidermal growth factor receptor and variant III targeted immunotherapy," Neuro-Oncology 16:viii20-viii25.

Database Geneseq [Online] (2007) "Fusion protein VH-VL of anti-EGFR antibody 528, Seq ID: 5," retrived from EBI accession No. GSP:AGE14548.

Han, J. et al. (2015) "CAR-Engineered NK Cells Targeting Wild-Type EGFR and EGFRvIII Enhance Killing of Glioblastoma and Patient-Derived Glioblastoma Stem Cells," Scientific Reports 5:11483, 1-13.

Johnson, L.A. et al. (2015) "Rational development and characterization of humanized anti-EGFR variant III chimeric antigen receptor T cells for glioblastoma," Science Translational Medicine 7(275):275ra22, 1-16.

Zhou, X. et al. (2013) "Cellular Immunotherapy for Carcinoma Using Genetically Modified EGFR-Specific T Lymphocytes," Neoplasia 15(5):544-553.

Extended European Search Report in European Application No. 16777143.5, dated Aug. 13, 2018.

Nishiyama et al., "Oncolytic Virotherapy using Replication-Competent Herpes Simplex Viruses", Virus, vol. 57, No. 1, 2007, pp. 57-66 (English Abstract).

Schonfeld et al., "Selective Inhibition of Tumor Growth by Clonal NK Cells Expressing an ErbB2/HER2-Specific Chimeric Antigen Receptor", Mol. Ther., vol. 23, No. 2, Dec. 9, 2014, pp. 330-338.

Zhou et al., "In vitro and in vivo anti-tumor activities of anti-Egfr single-chain variable fragment fused with recombinant gelonin toxin", Journal of Cancer Research and Clinical Oncology. vol. 138, Mar. 7, 2012, pp. 1081-1090.

Ahmed N, Salsman VS, Kew Y, et al. HER2-specific T cells target primary glioblastoma stem cells and induce regression of autologous experimental tumors. Clin Cancer Res. 2010;16(2):474-485. do1:10.1158/1078-0432.CCR-09-1322.

Biernat W, Huang H, Yokoo H, Kleihues P, Ohgaki H. Predominant expression of mutant EGFR (EGFRvIII) is rare in primary glioblastomas. Brain Pathol. 2004;14(2):131-136. doi:10.1111/j.1750-3639.2004.tb00045.x.

Brennan C, Momota H, Hambardzumyan D, et al. Glioblastoma subclasses can be defined by activity among signal transduction pathways and associated genomic alterations. PLoS One. 2009;4(11):e7752. Published Nov. 13, 2009. doi:10.1371/journal.pone.0007752.

Chandramohan V, Bao X, Keir ST, et al. Construction of an immunotoxin, D2C7-(scdsFv)-PE38KDEL, targeting EGFRwt and EGFRvIII for brain tumor therapy. Clin Cancer Res. 2013;19(17):4717-4727. do1:10.1158/1078-0432.CCR-12-3891.

Fan QW, Cheng CK, Gustafson WC, et al. EGFR phosphorylates tumor-derived EGFRvIII driving STAT3/5 and progression in glioblastoma. Cancer Cell. 2013;24(4):438-449. doi:10.1016/j.ccr.2013.09.004.

Gan HK, Cvrljevic AN, Johns TG. The epidermal growth factor receptor variant III (EGFRvIII): where wild things are altered. FEBS J. 2013;280(21):5350-5370. doi:10.1111/febs.12393.

Gedeon et al., "An EGFRvIII-targeted bispecific T-cell engager overcomes limitations of the standard of care for glioblastoma", Expert Rev. Clin. Pharamcol., vol. 6, No. 4, Jul. 2013, pp. 1-23.

Hayashi H, Asano R, Tsumoto K, et al. A highly effective and stable bispecific diabody for cancer immunotherapy: cure of xenografted tumors by bispecific diabody and T-LAK cells. Cancer Immunol Immunother. 2004;53(6):497-509. doi:10.1007/s00262-003-0465-9.

Humphrey PA, Wong AJ, Vogelstein B, et al. Anti-synthetic peptide antibody reacting at the fusion junction of deletion-mutant epidermal growth factor receptors in human glioblastoma. Proc Natl Acad Sci U S A. 1990;87(11):4207-4211. doi:10.1073/pnas.87.11.4207.A IgBLAST Search Results of PDB entry 1YY8 Heavy Chain obtained from https://www.ncbi.nlm.nih.gov/igblast.cgi on Jun. 18, 2020, 2 pages.

IgBLAST Search Results of PDB entry 1YY8 Light Chain obtained from https://www.ncbi.nlm.nih.gov/igblast.cgi on Jun. 18, 2020, 2 pages.

IMGT/2Dstructure-DB card for INN 8545, retrieved from imgt.org/3Dstructure-DB/cgi/details.cgi?pdbcode=8545 on May 27, 2020.

Kambara H, Okano H, Chiocca EE, Saeki Y. An oncolytic HSV-1 mutant expressing ICP34.5 under control of a nestin promoter increases survival of animals even when symptomatic from a brain tumor. Cancer Res. 2005;65(7):2832-2839. doi:10.1158/0008-5472.CAN-04-3227.

Mellman I, Coukos G, Dranoff G. Cancer immunotherapy comes of age. Nature. 2011;480(7378):480-489. Published Dec. 21, 2011. doi:10.1038/nature10673.

Morgan, R.A. et al. (2012) Recognition of glioma stem cells by genetically modified T cells targeting EGFRvIII and development of adoptive cell therapy for glioma. Hum Gene Ther. 23:1043-1053.

Ohno M, Natsume A, Ichiro Iwami K, et al. Retrovirally engineered T-cell-based immunotherapy targeting type III variant epidermal growth factor receptor, a glioma-associated antigen. Cancer Sci. 2010;101(12):2518-2524. doi:10.1111/j.1349-7006.2010.01734.x.

Parsons DW, Jones S, Zhang X, et al. An integrated genomic analysis of human glioblastoma multiforme. Science. 2008;321(5897):1807-1812. doi:10.1126/science.1164382.

PDB entry 1YY8, retrieved from https://www.rcsb.org/pdb/explore/remediatedSequence.do?structureId=1YY8 on May 27, 2020, 4 pages.

Phillips HS, Kharbanda S, Chen R, et al. Molecular subclasses of high-grade glioma predict prognosis, delineate a pattern of disease progression, and resemble stages in neurogenesis. Cancer Cell. 2006;9(3):157-173. doi:10.1016/j.ccr.2006.02.019.

Sampson JH, Choi BD, Sanchez-Perez L, et al. EGFRvIII mCAR-modified T-cell therapy cures mice with established intracerebral glioma and generates host immunity against tumor-antigen loss. Clin Cancer Res. 2014;20(4):972-984. doi:10.1158/1078-0432.CCR-13-0709.

Soffietti R, Ruda R, Mutani R. Management of brain metastases. J Neurol. 2002;249(10):1357-1369. doi:10.1007/s00415-002-0870-6.

Varghese S, Rabkin SD. Oncolytic herpes simplex virus vectors for cancer virotherapy. Cancer Gene Ther. 2002;9(12):967-978. doi:10.1038/sj.cgt.7700537.

Verhaak RG, Hoadley KA, Purdom E, et al. Integrated genomic analysis identifies clinically relevant subtypes of glioblastoma characterized by abnormalities in PDGFRA, IDH1, EGFR, and NF1. Cancer Cell. 2010;17(1):98-110. doi:10.1016/j.ccr.2009.12.020.

(56) References Cited

OTHER PUBLICATIONS

Zandi R, Larsen AB, Andersen P, Stockhausen MT, Poulsen HS. Mechanisms for oncogenic activation of the epidermal growth factor receptor. Cell Signal. 2007;19(10):2013-2023. doi:10.1016/j.cellsig.2007.06.023.

* cited by examiner

Fig. 4 A, B

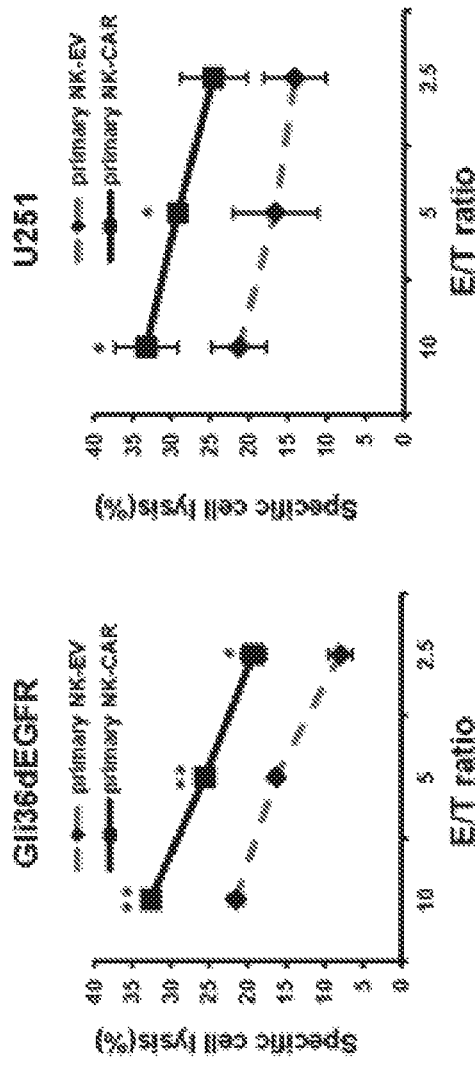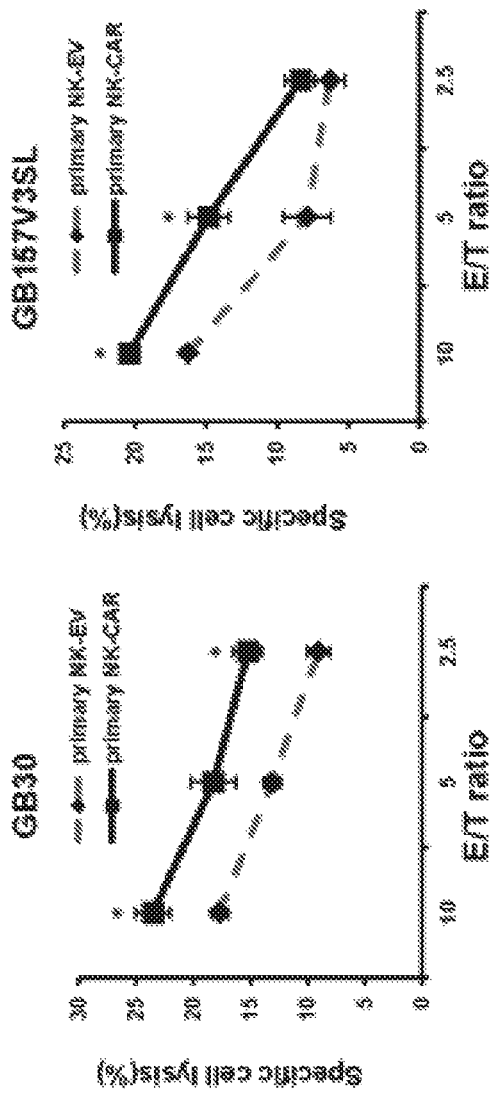
FIG. 8A
FIG. 8B

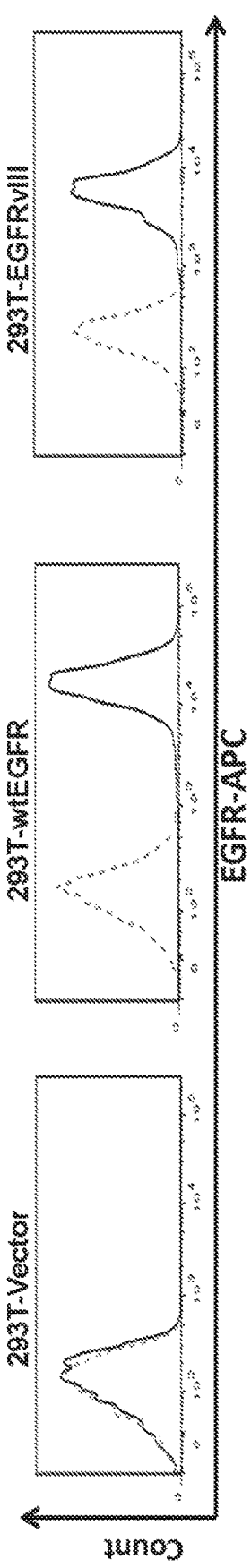
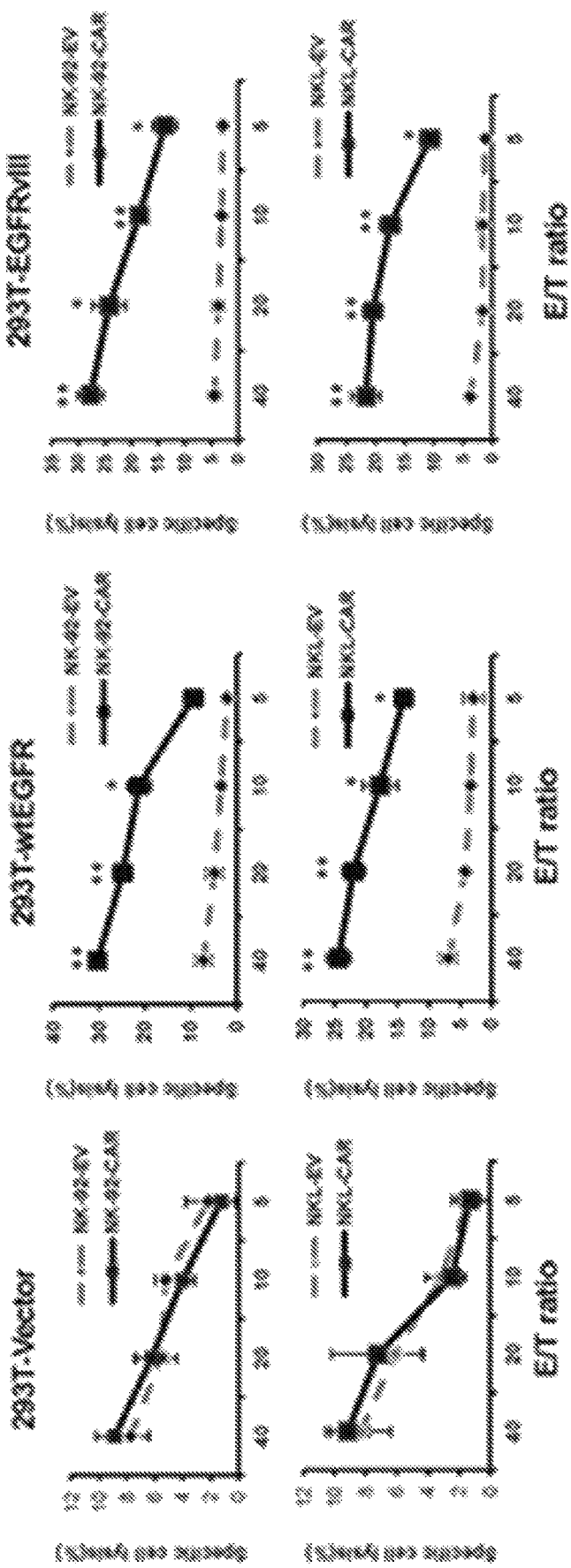
FIG. 9A
FIG. 9B

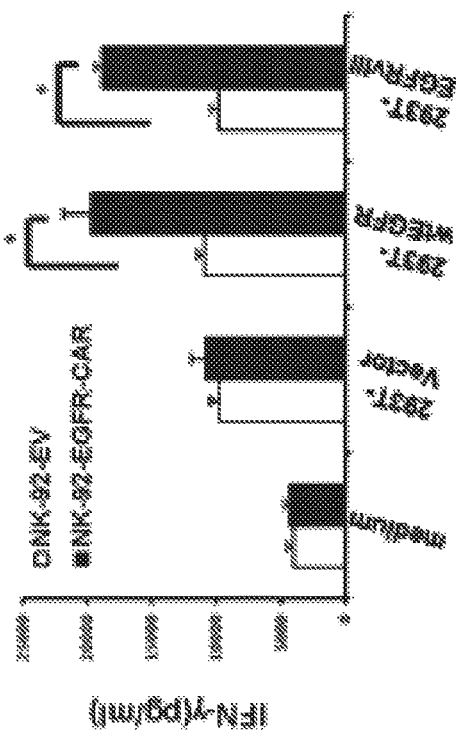
FIG. 9C
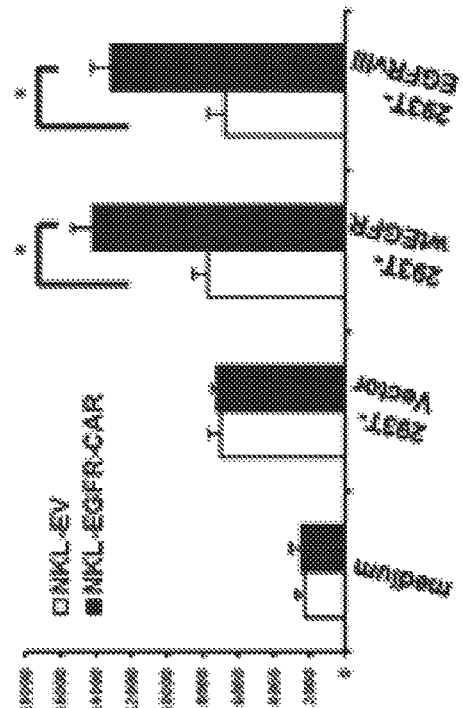
FIG. 10A
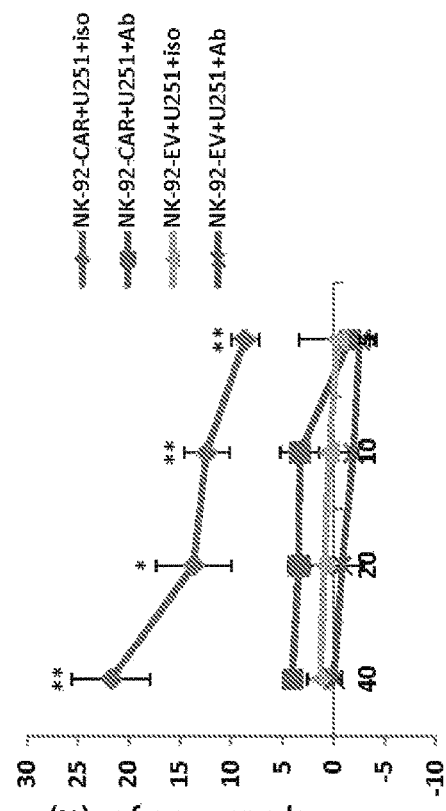
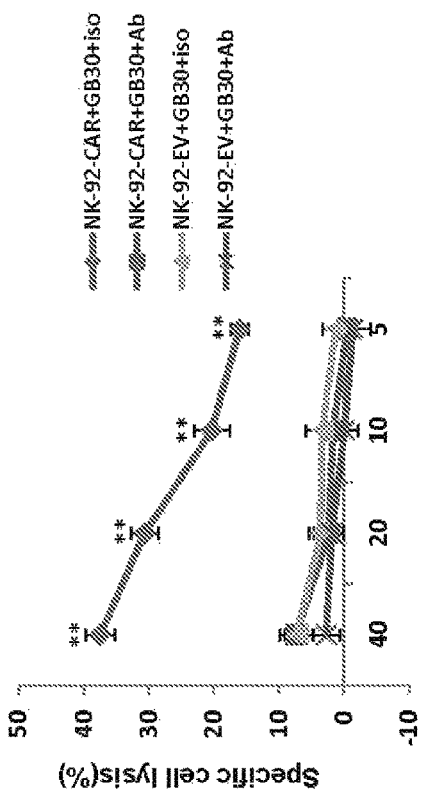

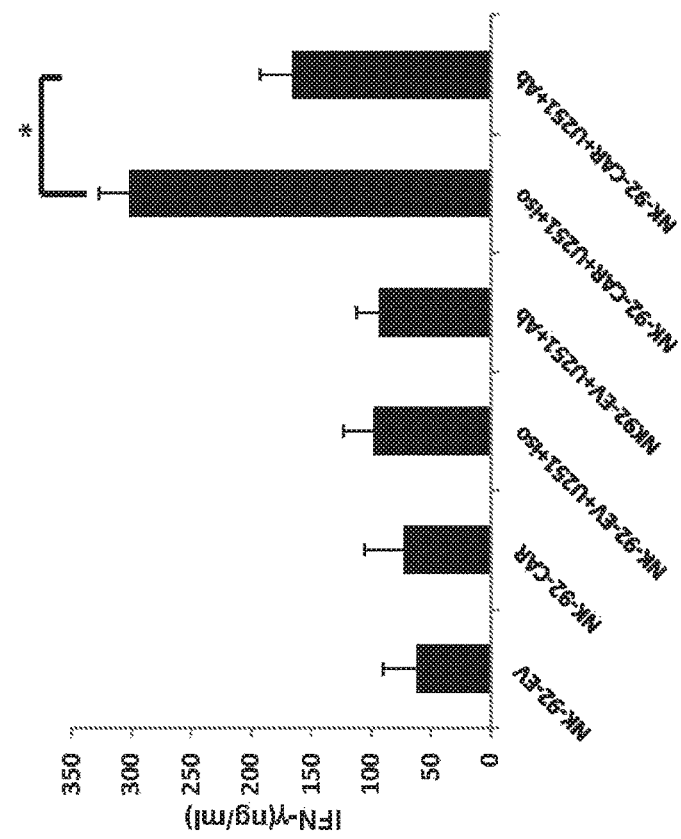
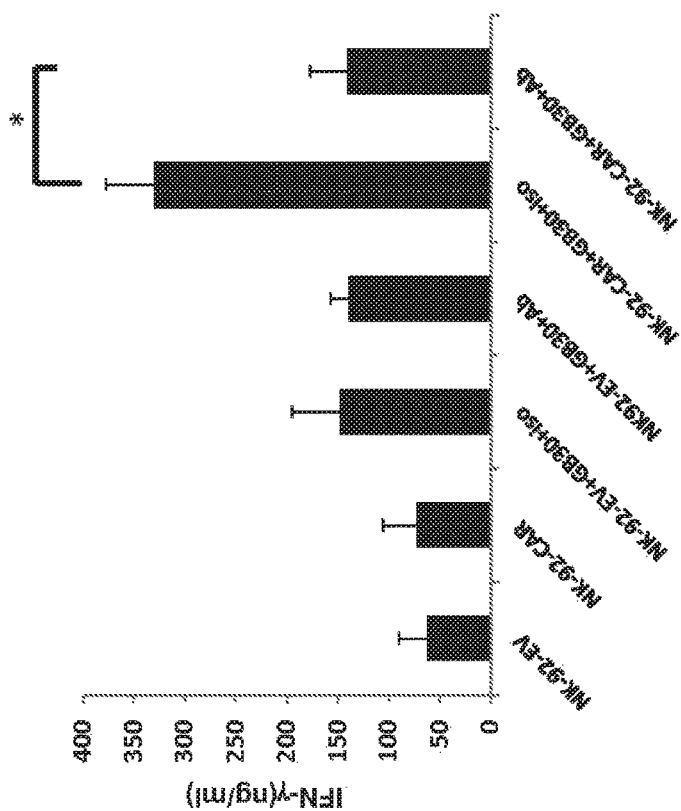
FIG. 10B

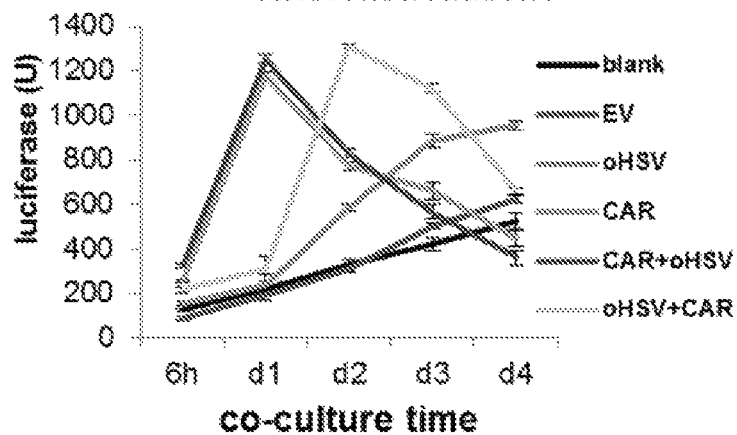
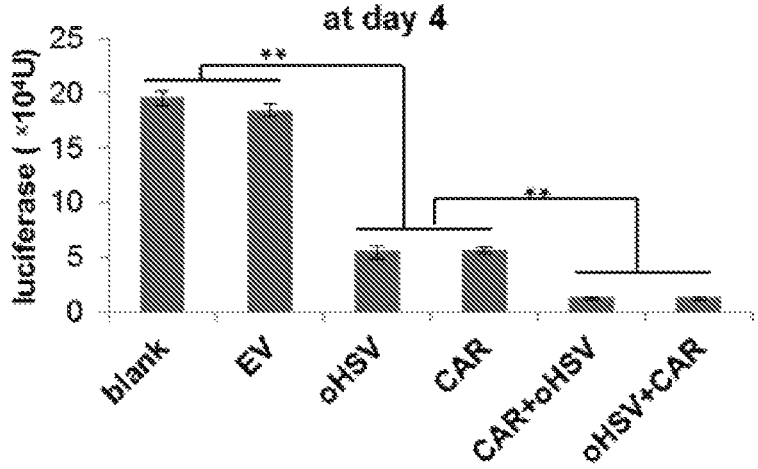
FIG. 16

EGFR-DIRECTED CAR THERAPY FOR GLIOBLASTOMA

CROSS-REFERENCE TO RELATED APPLICATIONS

This application is a national stage entry under 35 U.S.C. § 371 of International Application No. PCT/US2016/026057, filed Apr. 5, 2016, which in turn claims priority under 35 U.S.C. § 119(e) to U.S. Provisional Application No. 62/143,744, filed Apr. 6, 2015, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 18, 2016, is named 113086-0610_SL.txt and is 40,754 bytes in size.

BACKGROUND

Brain cancers are dangerous and difficult to treat. Glioblastoma (GB) is the most common and the most aggressive primary brain tumor. Cancer of the brain also poses a risk where it is the result of metastasis from another source; for example, breast cancer brain metastases (BCBMs) are common in patients with metastatic breast cancer. Even with chemotherapy, radiation, and surgical resection, the median overall survival of GB patients is only 14.6 months (Morgan, R. A. et al. (2012) Hum Gene Ther. 23:1043-1053). BCBMs are likewise highly resistant to available treatment and indicate poor prognosis for the patient. Conventional therapies generally lack specificity and can cause damage to the surrounding brain parenchyma and systemic tissues, a factor that limits their use (Imperato, J. P. et al. (1990) Ann Neurol. 28:818-822). Immune-based therapies for GB are a promising alternative to conventional treatments with a potential long-term benefit of generating a sustainable anti-tumor response with potential to target both localized and infiltrating tumor cells (Mellman, I. et al. (2011) Nature 480:480-489). The epidermal growth factor receptor (EGFR) plays an important role in various tumors including GB. EGFR is the most frequently amplified gene in GB, while its expression in normal brain tissue is either undetectable or extremely low (Parsons, D. W. et al. (2008) Science 321:1807-1812; Salomon, D. S. et al. (1995) Crit. Rev Oncol Hematol. 19:183-232). Binding of ligand to EGFR leads to receptor homo- and heterodimers formation, autophosphorylation of several key tyrosine residues leading to activation of several intracellular downstream signaling pathways including the Ras/Raf/MEK/ERK pathway, the PLCγ-PKC pathway and the PI3K/AKT pathway, resulting in cell proliferation, motility and survival (Zandi, R. et al. (2007) Cell Signal 19:2013-2023). Approximately 20-40% of EGFR-amplified tumors harbor the EGFR variant III mutant (EGFRvIII), which contains a deletion of exons 2-7 in the extracellular ligand-binding domain (Aldape, K. D. et al. (2004) Journal of Neuropathology and Experimental Neurology 63:700-707; Biernat, W. et al. (2004) Brain Pathol. 14:131-136; Fan, Q. W. et al. (2013) Cancer Cell 24:438-449; Sugawa, N. et al. (1990) Proc Natl Acad Sci. USA 87:8602-8606). This mutant form shows constitutive activation in the absence of ligand to activate the tumor-promoting signaling pathways (Ohno, M. et al. (2010) Cancer Sci. 101:2518-2524).

SUMMARY OF THE DISCLOSURE

Glioblastoma (GB) remains the most aggressive primary brain malignancy. Adoptive transfer of chimeric antigen receptor (CAR)-modified immune cells has emerged as a promising anti-cancer approach, yet the potential utility of CAR-engineered natural killer (NK) cells to treat GB has not been explored. Tumors from approximately 50% of GB patients express wild-type EGFR (wtEGFR) and in fewer cases express wtEGFR and the mutant form EGFRvIII; however, previously reported CAR T cell only focuses on targeting EGFRvIII.

Aspects of the disclosure relate to a chimeric antigen receptor (CAR) comprising: (a) an antigen binding domain; (b) a hinge domain; (c) a transmembrane domain; and (d) an intracellular domain. This disclosure provides a novel CAR—an Epidermal Growth Factor Receptor ("EGFR") chimeric antigen receptor (CAR) comprising, or alternatively consisting essentially of, or yet further consisting of: (a) an antigen binding domain of an anti-EGFR antibody that recognized both wild type and/or mutant Epidermal Growth Factor Receptor (EGFR) ("wt EGFR and mutant EGFR"); (b) a hinge domain polypeptide; (c) a costimulatory polypeptide; and (d) a CD3 zeta signaling domain. In one aspect, the costimulatory molecule comprises an intracellular domain and a transmembrane domain. Non-limiting examples include CD8, a 4-1BB costimulatory signaling region, a CD28 costimulatory molecule, OX40, ICOS and CD27. In one aspect, the antigen binding domain of the anti-EGFR antibody comprises an anti-EGFR heavy chain (HC) variable region and an anti-EGFR light chain (LC) variable region. In a yet further aspect, the EGFR CAR further comprises, or alternatively consists essentially of, or yet further consists of a linker polypeptide located between the anti-EGFR HC variable region and the anti-EGFR LC variable region. The CAR can further comprise a detectable label or a purification marker.

Polynucleotides encoding the EGFR CARs and their complements and equivalents of each are further disclosed herein. Vectors and host cells containing the polynucleotides and/or EGFR CARs are provided herein. The vectors are plasmids or vectors. The cells can be prokaryotic or eukaryotic cells. In one aspect, the cells are T cells or NK cells. The cells can be expanded and therefore an expanded population of the cells is further provided herein. The cells are, in one aspect, an activated population of cells such as T cells.

Diagnostic and therapeutic use of these compositions are further provided herein. For example, provided is method of inhibiting the growth of one or more of a cell and/or tumor expressing wt EGFR or mutant EGFR, or wt EGFR and mutant EGFR on the surface of the cell or a stem cell expressing EGFR, by contacting these cells with an effective amount of an isolated cell comprising an EGFR CAR as described herein. The cell can be a tumor cell, e.g., a glioblastoma or a cancer stem cell, e.g., a glioblastoma stem cell. The contacting can be in vitro or in vivo. When practiced in vitro, the method is useful to screen for new therapies or combination therapies. In vivo, the method is useful to treat a patient suffering from a cancer that expresses EGFR, e.g., a brain cancer such as glioblastoma or metastasis of another cancer (e.g. breast cancer) in the brain.

In another aspect, this disclosure provides a method of inhibiting the growth of one or more of: a cell expressing wt EGFR or mutant EGFR, or wt EGFR and mutant EGFR, on the surface of the cell in a subject in need thereof. This method comprises, or alternatively consisting essentially of, or yet further consisting of, administering to the subject an effective amount of the isolated cell comprising the EGFR CAR as described herein. The cell expressing EGFR can be a tumor cell or a cancer stem cell, e.g., a glioblastoma or a glioblastoma stem cell. The isolated cells expressing the EGFR CAR can be autologous to the subject receiving the cells. Yet further provided are methods to treat a cancer in a subject in need thereof, wherein the cancer cell expresses wt EGFR or mutant EGFR, or wt EGFR and mutant EGFR, by administering to the subject an effective amount the isolated cell comprising the EGFR CAR as described herein. The isolated cells of these methods can be NK cells and/or T-cells and can be autologous to the subject being treated. In a further aspect, the cells are administered by any appropriate route as determined by the treating physician and include without limitation, intracranial injection, intravenous administration Yet further provided is an isolated complex comprising the EGFR CAR as described herein and an EGFR protein or a fragment thereof and/or mutant EGFR protein or a fragment thereof. In another aspect, provided herein is an isolated complex comprising the EGFR CAR as described herein and a cell expressing a wt EGFR or mutant EGFR, or wt EGFR and mutant EGFR.

Further aspects of the disclosure relate to compositions and combination cancer therapy with the EGFR CAR expressing cells, such as T cells or NK cells, described herein and oncolytic herpes simplex viruses. Some embodiments relate to a method of treating a tumor or cancer where both a EGFR CAR expressing cell and an oncolytic herepes simplex are administered to a patient in need thereof. In some embodiments, the EGFR CAR expressing cells are administered simultaneously with the oncolytic herpes simplex virus; in other embodiments, the EGFR CAR expressing cells are administered before or after administration of the oncolytic herpes simplex virus.

Kits comprising one or more of the above compositions are further provided. Instructions to use them diagnostically or therapeutically are further provided.

BRIEF DESCRIPTION OF THE DRAWINGS

(FIG. 1A) Surface EGFR expression on glioma cell lines (U251, LN229, and Gli36dEGFR) and glioma stem cells (GB30, GB83, GB326, GB1123, GB84V3SL, GB157V3SL, and GB19) was monitored by flow cytometry. NK cell lines NKL and NK-92 serve as negative controls. (FIG. 1B). Determination of EGFR mRNA expression by RT-PCR in glioma cell lines and glioma stem cells specified in FIG. 1A. Flow plots and data are representative of three independent experiments.

(FIG. 2A) Schematic representation of the EGFR-CAR lentiviral construct. (FIG. 2B) Expression of chimeric EGFR scFv on the surface of NK-92 and NKL cells transduced either with the EGFR-CAR construct (NK-92-EGFR-CAR and NKL-EGFR-CAR, respectively) or the empty vector construct (EV). Cells were FACS-sorted by GFP expression, then analyzed by flow cytometry after the cells were stained with an anti-mouse Fab antibody (solid lines) or IgG isotype control (dashed lines). SP, signal peptide; VH, heavy chain; VL, light chains; ScFv, single chain variable fragment. Flow plots and data are representative of three independent experiments.

(FIG. 3A) Cytotoxic activity of empty vector (EV)-transduced or EGFR-CAR-transduced NK-92 and NKL cells against Gli36dEGFR, LN229 or U251 cells using a standard chromium-51 release assay. (FIG. 3B) IFN-γ release of empty vector EV-transduced or EGFR-CAR-transduced NK-92 and NKL cells in the absence or presence of Gli36dEGFR, LN229 or U251 cells using ELISA assay. Representative data of three independent experiments are shown. *p<0.05; **p<0.01.

(FIG. 4A) Cytotoxic activity of NK-92-EV or NK-92-EGFR-CAR cells (upper panel) and NKL-EV or NKL-EGFR-CAR cells (lower panel) against GB1123, GB30, GB157V3SL, and GB84V3SL GB stem cells using chromium-51 release assay. (FIG. 4B) ELISA analysis of IFN-γ secretion by NK-92-EGFR-CAR or NK-92-EV cells (upper panel) and NKL-EV or NKL-EGFR-CAR cells (lower panel) when co-cultured with GB stem cells. Representative data of three independent experiments are shown. *p<0.05; **p<0.01.

(FIG. 5A) Flow cytometry using an anti-EGFR antibody (solid line) or IgG isotype control (dotted line) to detect EGFR expression on the surface of GB19 cells transfected with an empty vector or vectors containing wtEGFR or EGFRvIII. (FIG. 5B) Cytotoxicity of NK-92-EV or NK-92-EGFR-CAR (upper panel) and NKL-EV or NKL-EGFR-CAR (lower panel) against the GB19, GB19-wtEGFR, and GB19-EGFRvIII cells shown in FIG. 5A. The GB19 cells were incubated with NK-92 or NKL cells at various Effector/Target (E/T) ratios for 4 h. Tumor lysis was determined using chromium-51 release assay. (FIG. 5C) NKL-EV or NKL-EGFR-CAR (left) and NK-92-EGFR-CAR or NK-92-EV cells (right) were co-cultured with equal numbers of GB19-Vector or GB19-EGFR cells for 24 h. Supernatants were then harvested for measurement of IFN-γ secretion using ELISA. Flow plots and data are representative of three independent experiments. *p<0.05, **p<0.01.

(FIG. 6A) Brain bioluminescence imaging of mice bearing GB30 tumors. NSG mice were inoculated with luciferase-expressing GB30 cells via stereotaxic injection (day 0). Seven days after inoculation, mice were intracranially infused once with empty vector-transduced NK-92 cells (NK-92-EV), EGFR-CAR-transduced NK-92 cells (NK-92-EGFR-CAR) or Hank's buffered salt solution (HBSS; negative control). (FIG. 6B) Quantification summary of units of photons per second per mouse from FIG. 6A. * indicates p<0.05. (FIG. 6C) GB30-bearing mice treated with NK-92-EGFR-CAR cells showed significantly increased overall survival compared to the mice treated with NK-92-EV cells or HBSS (** p<0.01), as determined by Kaplan-Meier survival curves (n=5 for each group). (FIG. 6D) Determination of presence of CD56$^+$CD3$^-$ human EGFR-CAR NK-92 cells by flow cytometry in liver, lung, blood, spleen, bone marrow (BM), and brain 3 days after intracranial injection of the CAR NK cells into brain of GB30-bearing mice. (FIG. 6E) Determination of EGFR-CAR expression by RT-PCR in liver, lung, blood, spleen, bone marrow (BM), and brain 3 days after intracranial injection of the CAR NK cells into brain of GB30-bearing mice. NC=negative control (no DNA template was added); PC=positive control, EGFR-CAR NK-92 cells. *p<0.05, **p<0.01.

(FIG. 7A) Brain bioluminescence imaging of mice bearing U251 tumors. NSG mice were intracranially implanted with $10^5$ luciferase-expressing U251 cells via stereotaxic injection (day 0). Day 10, 40, 70 after inoculation, mice were intracranially infused with NK-92-EV cells, NK-92-EGFR-CAR cells or HBSS as negative control. Brain bioluminescence imaging of mice was taken on Day 100. (FIG. 7B) Quantification summary of units of photons per second per mouse from FIG. 7A. ** indicates p<0.01. (FIG. 7C) U251-bearing mice treated with NK-92-EGFR-CAR cells showed significantly increased overall survival compared to the mice treated with NK-92-EV cells (* p<0.05), or HBSS ** p<0.01), as determined by Kaplan-Meier survival curves (n=5 for each group).

FIGS. 8A-8B show that EGFR-CAR primary NK cells display enhanced eradication of $EGFR^+$ GB cells and patient-derived GB stem cells. (FIG. 8A) EGFR-CAR-modified primary NK cells (primary NK-CAR) displayed augmented cytolytic activity towards $EGFR^+$ Gli36dEGFR and U251 GB cell lines in comparison with mock-transduced primary NK cells (primary NK-EV). (FIG. 8B) EGFR-CAR-modified NK cell (primary NK-CAR) showed enhanced cytotoxicity towards $EGFR^+$-patient-derived GB30 and GB157V3SL stem cells in comparison with mock-transduced primary NK cells (primary NK-EV). Data presented are representative of three experiments with similar results, examining NK cells isolated from different healthy donors. *p<0.05; **p<0.01.

FIGS. 9A-9C show that enhanced target recognition of NK-92-EGFR-CAR cells depends on expression of EGFR on the cell surface. (FIG. 9A) Flow cytometric analysis using anti-EGFR antibody (solid line) or IgG isotype control (dotted line) of 293T cells transduced with empty vector (EV; left), wtEGFR (center) or EGFRvIII (right). (FIG. 9B) Cytotoxicity of NK-92-EV or NK-92-EGFR-CAR (top panel) and NKL-EV or NKL-EGFR-CAR (lower panel) against 293T-EV (left), 293T-EGFR (center), and 293T-EGFRvIII (right) cells. 293T cells were incubated with NK cells at various Effector/Target (E/T) ratios for 4 h. Tumor lysis was determined using chromium-51 release assay. (FIG. 9C) After coincubation of target cells and effector cells for 24 h, supernatants from the co-cultures were measured for IFN-γ secretion using ELISA. Data presented are representative of three experiments with similar results. *p<0.05; **p<0.01.

FIGS. 10A-10B show that the effects of NK-92-EGFR-CAR cells are blunted by an EGFR blocking antibody (Ab). (FIG. 10A) Cytotoxicity of NK-92-EV or NK-92-EGFR-CAR against GB30 cells (Left) or U251 cells (Right) pretreated with an EGFR-specific monoclonal antibody 528 or an IgG-matched isotype control antibody. Target cells were incubated with pre-treated NK-92-EV or NK-92-EGFR-CAR cells at various Effector/Target (E/T) ratios for 4 h. Tumor lysis was determined using chromium-51 release assay. (FIG. 10B) After co-incubation of target cells and effector cells for 24 h, supernatants from the co-cultures were measured for IFN-γ secretion using ELISA. Data presented are representative of three experiments with similar results. *p<0.05; **p<0.01. Ab=EGFR-specific monoclonal antibody 528; iso=IgG-matched isotype control antibody.

FIG. 15B depicts MTS assays of oHSV-1 cytotoxicity against breast cancer ca lines, MDA-MB-231, MDA-MB-468 or MCF-7, after co-cultured of them for different time periods. FIG. 15C shows measurement of luciferase levels in the media of the co-culture of MDA-MB-231-CBRluc-EGFP cells and oHSV-1.

FIGS. 16A-16B reveal that the combinational treatment of EGFR-CAR NK-92 cells and oHSV-1 results in more efficient eradication of breast cancer tumor cells in vitro. Tumor cells were treated with CAR cells alone, oHSV-1 alone, EGFR-CAR NK-92 cells for 4 h followed by oHSV-1 (CAR+oHSV), or oHSV for 4 h followed by EGFR-CAR NK-92 cells (oHSV+CAR). Eradication of MDA-MB-231 tumor cells expressing CBRluc-EGFP was measured by luciferase release to supernatants at different time points (FIG. 16A). Regardless of the order, the EGFR-CAR NK-92 cells in combination with oHSV-1 (CAR+oHSV or oHSV+CAR) eradicated more MDA-MB-231 tumor cells than EGFR-CAR NK-92 cells alone (CAR) or oHSV-1 alone (oHSV), determined by the relative light units of luciferase remained in the MDA-MB-231-CBRluc-EGFP cells on day 4 after co-cultured. ** P<0.01 (FIG. 16B). Data are representative of three independent experiments FIGS. 17A-17B demonstrate that EGFR-CAR transduced NK-92 cells inhibit MDA-MB-231 tumor growth with prolonged survival of the tumor-bearing mice. Brain bioluminescence imaging of mice bearing BCBM tumors. NSG mice were inoculated with MDA-MB-231-CBRluc-EGFP cells via stereotaxic injection (day 0). 10 days after inoculation, mice were intracranially infused once with EGFR-CAR NK-92, oHSV-1, NK-92-EV, or HBSS. The mice of combined treatment group were injected with oHSV-1 on day 15. Four weeks after inoculation with MDA-MB-231-CBRluc-EGFP cells, the mice were intraperitoneally infused with D-luciferin and imaged using the In Vivo Imaging System (FIG. 17A). MDA-MB-231-CBRluc-EGFP tumor-bearing mice were intratumorally treated with EGFR-CAR NK-92 cells followed by oHSV-1 injection (CAR+oHSV), EGFR-CAR NK-92 cells alone (CAR), oHSV-1 alone, or HBSS control. As a result, EGFR-CAR NK-92 cells followed by oHSV-1 injection showed significantly increased overall survival than the rest of treatments as determined by Kaplan-Meier survival curves (n=5 for each group) (FIG. 17B).

DETAILED DESCRIPTION

Figure 1A:
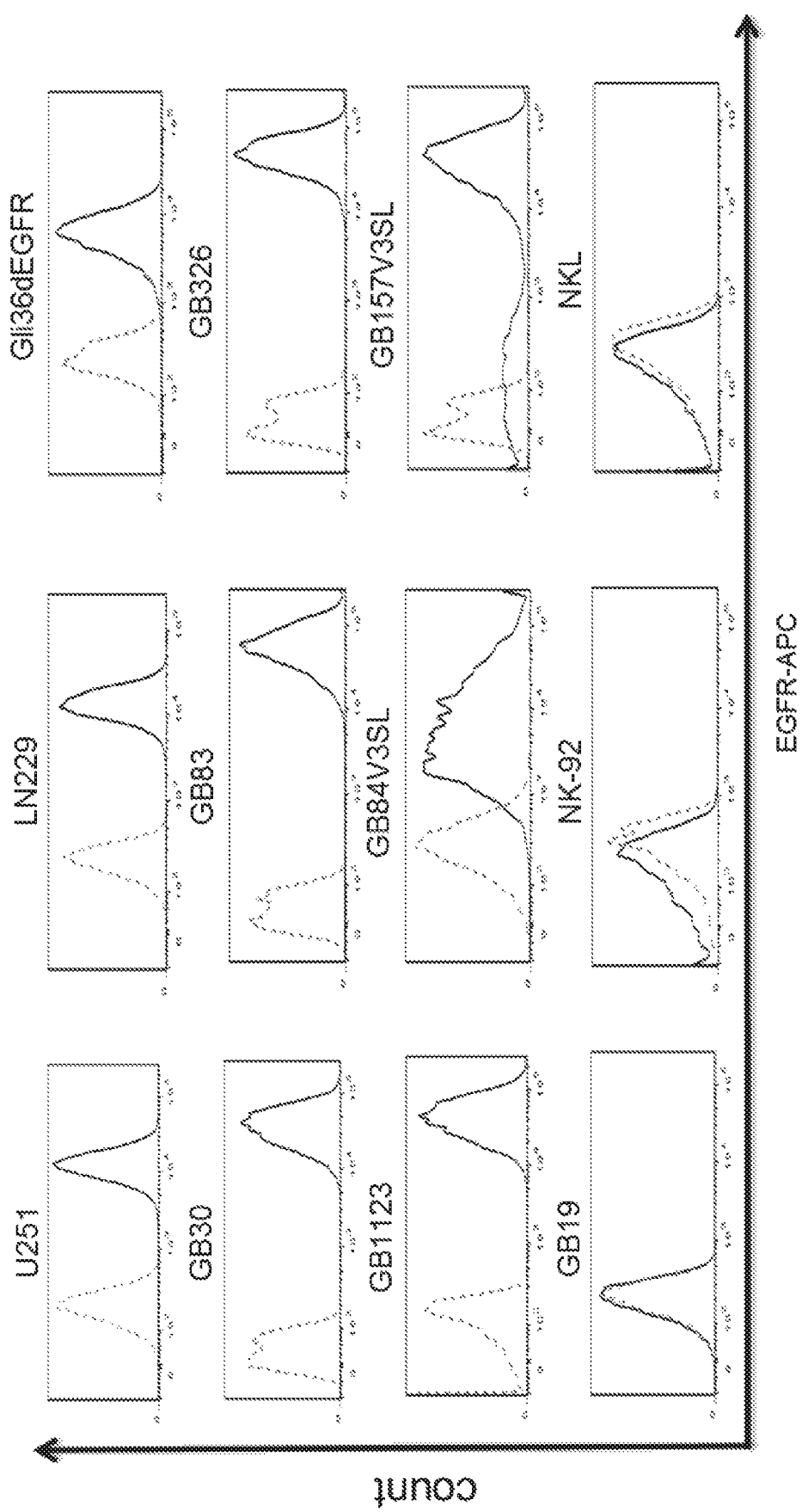
FIGS. 1A-1B show expression of EGFR on GB and GB stem cells.

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual,* 3rd edition; the series Ausubel et al. eds. (2007) *Current Protocols in Molecular Biology;* the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach;* Harlow and Lane eds. (1999) *Antibodies, A Laboratory Manual;* Freshney (2005) *Culture of Animal Cells: A Manual of Basic Technique,* 5th edition; Gait ed. (1984) *Oligonucleotide Synthesis;* U.S. Pat. No. 4,683,195; Hames and Higgins eds. (1984) *Nucleic Acid Hybridization;* Anderson (1999) *Nucleic Acid Hybridization;* Hames and Higgins eds. (1984) *Transcription and Translation; Immobilized Cells and Enzymes* (IRL Press (1986)); Perbal (1984) *A Practical Guide to Molecular Cloning;* Miller and Calos eds. (1987) *Gene Transfer Vectors for Mammalian Cells* (Cold Spring Harbor Laboratory); Makrides ed. (2003) *Gene Transfer and Expression in Mammalian Cells;* Mayer and Walker eds. (1987) *Immunochemical Methods in Cell and Molecular Biology* (Academic Press, London); and Herzenberg et al. eds (1996) *Weir's Handbook of Experimental Immunology.*

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W.H. Freeman & Co., New York, 1997.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds EGFR will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.:

Hinge domain: IgG1 heavy chain hinge sequence:

(SEQ ID NO: 1)
CTCGAGCCCAAATCTTGTGACAAAACTCACACATGCCCACCGTGCCCG

Transmembrane domain: CD28 transmembrane region:

(SEQ ID NO: 2)
TTTTGGGTGCTGGTGGTGGTTGGTGGAGTCCTGGCTTGCTATAGCTTGCT

AGTAACAGTGGCCTTTATTATTTTCTGGGTG

Intracellular domain: 4-1BB co-stimulatory signaling region:

(SEQ ID NO: 3)
AAACGGGGCAGAAAGAAACTCCTGTATATATTCAAACAACCATTATGAGA

CCAGTACAAACTACTCAAGAGGAAGATGGCTGTAGCTGCCGATTTCCAGA

AGAAGAAGAAGGAGGATGTGAACTG

Intracellular domain: CD28 co-stimulatory signaling region:

(SEQ ID NO: 4)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

Intracellular domain: CD3 zeta signaling region:

(SEQ ID NO: 5)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non-limiting examples of such domains are provided herein.

The acronym "EGFR" stands for Epidermal Growth Factor Receptor. EGFR also is known as ErbB-1 and HER1. It is the cell surface receptors of the epidermal growth factor family of cell surface receptors. The term "EGFR" also refers to a specific protein fragment associated with this name and any other molecules that have analogous biological function that share at least 70%, or alternatively at least 80% amino acid sequence identity, preferably 90% sequence identity, more preferably at least 95% amino acid sequence identity with any isoform of EGFR, as disclosed herein. Isoform 1 is the canoncial sequence; thus, all positional information that follows refers to the amino acid sequence disclosed below.

EGFR Isoform 1, Uniprot P00533-1:

(SEQ ID NO: 6)
MRPSGTAGAALLALLAALCPASRALEEKKVCQGTSNKLTQLGTFEDHFLS

LQRMFNNCEVVLVNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGSDSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTLDHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIAG

Binding sites include but are not limited to positions 745 and 855; active sites include but are not limited to position 837; and other sites of interest include but are not limited to position 1016. EGFR Isoform 2 (Uniprot P00533-2) has an FL to LS substitution at position 404 to 405 and is missing the region from position 406 to 1210. EGFR Isoform 4 (Uniprot P00533-4) has a C to S substitution at position 628 and is missing the region from position 629 to 1210. EGFR Isoform 3 (Uniprot P00533-3) differs from positons 628 to 705 and is missing the region from position 706 to 1210, in accordance with the sequence below.

EGFR Isoform 3, Uniprot P00533-3:

(SEQ ID NO: 7)
MRPSGTAGAALLALLAALCPASRALEEKKVCQGTSNKLTQLGTFEDHFLS

LQRMFNMCEVVLGNLEITYVQRNYDLSFLKTIQEVAGYNLIALNTVERIP

LENLQIIRGNMYYENSYALAVLSNYDANKTGLKELPNRNLQEILHGAVRF

SNNPALCNVESIQWRDIVSSDFLSNMSMNDFQNHLGSCQKCDPSCPNGSC

WGAGEENCQKLTKIICAQQCSGRCRGKSPSDCCHNQCAAGCTGPRESDCL

VCRKFRDEATCKDTCPPLMLYNPTTYQMDVNPEGKYSFGATCVKKCPRNY

VVTDHGSCVRACGADSYEMEEDGVRKCKKCEGPCRKVCNGIGIGEFKDSL

SINATNIKHFKNCTSISGDLHILPVAFRGDSFTHTPPLDPQELDILKTVK

EITGFLLIQAWPENRTDLHAFENLEIIRGRTKQHGQFSLAVVSLNITSLG

LRSLKEISDGDVIISGNKNLCYANTINWKKLFGTSGQKTKIISNRGENSC

KATGQVCHALCPSPEGCWGPEPRDCVSCRNVSRGRECVDKCNLLEGEPRE

FVENSECIQCHPECLPQAMNITCTGRGPDNCIQCAHYIDGPHCVKTCPAG

VMGENNTLVWKYADAGHVCHLCHPNCTYGPGNESLKAMLFCLFKLSSCNQ

SNDGSVSHQSGSPAAQESCLGWIPSLLPSEFQLGWGGCSHLHAWPSASVI

ITASSCH

EGFRvIII is a mutant form of EGFR that is reported to be expressed in a considerable proportion of patients with glioblastoma multiforme (GB). Gan et al. 205350-5370 report that the mutant form is expressed in other tumors as well. The term "mutant EGFR" may refer to EGFRvIII or a specific protein fragment associated with this name and any other molecules that have analogous biological function that share at least 70%, or alternatively at least 80% amino acid sequence identity, preferably 90% sequence identity, more preferably at least 95% amino acid sequence identity with the EGFRvIII, as shown herein or an equivalent thereof as further defined herein.

EGFRvIII, Uniprot P00533[30-297]:

```
                                              (SEQ ID NO: 8)
MRPSGTAGAA  LLALLAALCP  ASRALEEKKV  CQGTSNKLTQ

LGTFEDHFLS  LQRMFNNCEV  VLGNLEITYV  QRNYDLSFLK

TIQEVAGYVL  IALNTVERIPLENLQIIRGN  MYYENSYALA

VLSNYDANKT  GLKELPMRNL  QEILHGAVRF  SNNPALCNVE

SIQWRDIVSS  DFLSNMSMDF  QNHLGSCQKC

DPSCPNGSWGAGEENCQKL  TKIICAQQCS  GRCRGKSPSD

CCHNQCAAGC  TGPRESDCLV  CRKFRDEATC  KDTCPPLMLY

NPTTYQMDVN  PEGKYSFGAT  CVKKCPRNYV  VTDHGSCVRA

CGADSYEMEE  DGCRKCKKCE  GPCRKVCNGI  GIGEFKDSLS

INATNIKHFK  NCTSISGDLH  ILPVAFRGDS  FTHTPPLDPQ

ELDILKTVKE  ITGFLLIQAW  PENRTDLHAF  ENLEIIRGRT

KQHGQFSLAV  VSLNITSLGL  RSLKEISDGD  VIISGNKNLC

YANTINWKKL  FGTSGQKTKI  ISNRGENSCK  ATGQVCHALC

SPEGCWGPEP  RDCVSCRNVS  RGRECVDKCN  LLEGEPREFV

ENSECIQCHP  ECLPQMANIT  CTGRGPDNCI  QCAHYIDGPH

CVKTCPAGVN  GENNTLVWKY  ADAGHVCHLC  HPNCTYGCTG

PGLEGCPTNG  PKIPSIATGM  VGALLLLLVV  ALGIGLFMRR

RHIVRKRTLR  RLLQERELVE  PLTPSGEAPN  QALLRILKET

EFKKIKVLGS  GAFGTVYKGL  WIPEGEKVKI

PVAIKELREATSPKANKEIL  DEAYVMASVD  NPHVCRLLGI

CLTSTVQLIT  QLMPFGCLLDYVREHKDNIG  SQYLLNWCVQ

IAKGMNYLED  RRLVHRDLAA  RNVLVKTPQHVKITDFGLAK

LLGAEEKEYH  AEGGKVPIKW  MALESILHRI

YTHQSDVWSYGVTVWELMTF  GSKPYDGIPA  SEISSILEKG

ERLPQPPICT  IDVYMIMVKC  WMIDADSRPK  FRELIIEFSK

MARDPQRYLV  IQGDERMHLPLMDEEDMDDV  VDADEYLIPQ

QGFFSSPSTS  RTPLLSSLSA  TSNNSTVACIDRNGLQSCPI

KEDSFLQRYS  SDPTGALTED  SIDDTFLPVP

EYINQSVPKRPAGSVQNPVY  HNQPLNPAPS  RDPHYQDPHS

TAVGNPEYLN  TVQPTCVNSTFDSPAHWAQK  GSHQISLDNP

DYQQDFFPKE  AKPNGIFKGS  TAENAEYLRVAPQSSEFIGA
```

The term "mutant EGFR" may also refer to a natural variant of any isoform of EGFR including but not limited variants with one or more of the following mutations: R to Q at position 98, P to R at position 266, G to D at position 428, R to K at position 521, V to I a position 674, E to A at position 709, E to G at position 709, E to K at position 709, G to A at position 719, G to C at position 719, G to D at position 719, G to S at position 719, G to S at position 724, E to K at position 734, ELREATS (SEQ ID NO: 9) to D at positions 746 to 752, ELREAT (SEQ ID NO: 10) to A at positions 746 to 751, a deletion from positions 746 to 750, a deletion at position 746, a deletion from positions 747 to 751, a deletion from positions 747 to 749, L to F at position 747, R to P at position 748, a deletion from positions 752 to 759, S to I at position 768, V to M at position 769, Q to R at position 787, T to M at position 790, L to V at position 833, V to L at position 834, H to L at position 835, L to V at position 838, L to M at position 858, L to R at position 858, L to Q at position 861, G to E at position 873, R to G at position 962, H to P at position 988, L to R at position 1034, A to V at position 1210, and/or a different amino acid substitution or deletion at any one of the specific positions.

A "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CD8 α hinge domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. The sequences associated with the CD8 α hinge domain are provided in Pinto, R. D. et al. (2006) Vet. Immunol. Immunopathol. 110:169-177. Non-limiting examples of such include:

Human CD8 alpha hinge domain, (SEQ ID NO: 11)
PAKPTTTPAPRPPTPAPTIASQPLSLRPEACRPAAGGAVHTRGLDFACD
IY Mouse CD8 alpha hinge domain, (SEQ ID NO: 12)
KVNSTTTKPVLRTPSPVHPTGTSQPQRPEDCRPRGSVKGTGLDFACDIY Cat CD8 alpha hinge domain, (SEQ ID NO: 13)
PVKPTTTPAPRPPTQAPITTSQRVSLRPGTCQPSAGSTVEASGLDLSCD
IY As used herein, the term "CD8 α transmembrane domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α transmembrane domain sequence as shown herein. The fragment sequences associated with the amino acid positions 183 to 203 of the human T-cell surface glycoprotein CD8 alpha chain (NCBI Reference Sequence: NP_001759.3), or the amino acid positions 197 to 217 of the mouse T-cell surface glycoprotein CD8 alpha chain (NCBI Reference Sequence: NP_001074579.1), and the amino acid positions190 to 210 of the rat T-cell surface glycoprotein CD8 alpha chain (NCBI Reference Sequence: NP_113726.1) provide additional example sequences of the CD8 α transmembrane domain. The sequences associated with each of the listed NCBI are provided as follows:

Human CD8 alpha transmembrane domain:

(SEQ ID NO: 14)
IYIWAPLAGTCGVLLLSLVIT

Mouse CD8 alpha transmembrane domain:

(SEQ ID NO: 15)
IWAPLAGICVALLLSLIITLI

Rat CD8 alpha transmembrane domain:

(SEQ ID NO: 16)
IWAPLAGICAVLLLSLVITLI

As used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown herein. The example sequences of the 4-1BB costimulatory signaling region are provided in U.S. Publication 20130266551A1 (filed as U.S. application Ser. No. 13/826,258). The sequence of the 4-1BB costimulatory signaling region associated disclosed in the U.S. App. No. U.S. Ser. No. 13/826,258 is disclosed as follows:

The 4-1BB costimulatory signaling region:

(SEQ ID NO: 17)
KRGRKKLLYIFKQPFMRPVQTTQEEDGCSCRFPEEEEGGCEL

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM_009444056.1 provide additional, non-limiting, example sequences of the CD28 transmembrane domain. The sequences associated with each of the listed accession numbers are provided as follows the sequence mentioned herein above.

As used herein, the term "CD28 costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the CD28 costimulatory signaling region sequence shown herein. The CD28 costimulatory region comprises an transmembrane domain and an intracellular domain. The example sequences CD28 costimulatory signaling domain are provided in U.S. Pat. No. 5,686,281; Geiger, T. L. et al., Blood 98: 2364-2371 (2001); Hombach, A. et al., J Immunol 167: 6123-6131 (2001); Maher, J. et al. Nat Biotechnol 20: 70-75 (2002); Haynes, N. M. et al., J Immunol 169: 5780-5786 (2002); Haynes, N. M. et al., Blood 100: 3155-3163 (2002). Non-limiting examples include residues 114-220 of the below CD28 Sequence:

(SEQ ID NO: 18)
MLRLLLALNL FPSIQVTGNK ILVKQSPMLV AYDNAVNLSC

KYSYNLFSRE FRASLHKGLDSAVEVCVVYG NYSQQLQVYS

KTGFNCDGKL GNESVTFYLQ NLYVNQTDIY

FCKIEVMYPPPYLDNEKSNG TIIHVKGKHL CPSPLFPGPS

KPFWVLVVVG GVLACYSLLVTVAFIIFWVR SKRSRLLHSD

YMNMTPRRPG PTRKHYQPYA PPRDFAAYRS, and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide sequence provided below.

ICOS costimulatory signaling region:

```
                                          (SEQ ID NO: 19)
ACAAAAAAGA AGTATTCATC CAGTGTGCAC GACCCTAACG

GTGAATACAT GTTCATGAGA GCAGTGAACA CAGCCAAAAA

ATCCAGACTC ACAGATGTGA CCCTA
```

As used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include the exemplary sequence provided below.

OX40 costimulatory signaling region, SEQ ID NO:20:

```
AGGGACCAG AGGCTGCCCC CCGATGCCCA CAAGCCCCCT

GGGGGAGGCA GTTTCCGGAC CCCCATCCAA GAGGAGCAGG

CCGACGCCCA CTCCACCCTG GCCAAGATC
```

As used herein, the term "CD3 zeta signaling domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD3 zeta signaling domain sequence as shown herein. The example sequences of the CD3 zeta signaling domain are provided in U.S. App. No. U.S. Ser. No. 13/826,258. The sequence associated with the CD3 zeta signaling domain is listed as follows:

```
                                          (SEQ ID NO: 21)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
```

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™), CA46 (ATCC® CRL-1648™), DG-75 [D.G.-75] (ATCC® CRL-2625™), DS-1 (ATCC® CRL-11102™), EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines deived from anaplastic and large cell lymphomas, e.g., DEL, DL-40, FE-PD, JB6, Karpas 299, Ki-JK, Mac-2A Ply1, SR-786, SU-DHL-1, -2, -4, -5,-6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (https://www.dsmz.de/).

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK-92 (ATCC, CRL-2407) and NKL (described in Robertson et al. (1996) 24(3): 406-414) are specific examples of NK cells. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multistranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term signal peptide or signal polypeptide intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "isolated cell" generally refers to a cell that is substantially separated from other cells of a tissue. "Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

As used herein, the term "isolated cell" generally refers to a cell that is substantially separated from other cells of a tissue. The term includes prokaryotic and eukaryotic cells. "Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "autologous," in reference to cells refers to cells that are isolated and infused back into the same subject (recipient or host). "Allogeneic" refers to non-autologous cells.

An "effective amount" or "efficacious amount" refers to the amount of an agent, or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

As used herein, the term "cancer" refers to any one of a group of diseases involving abnormal cell growth with the potential to invade or spread to other parts of the body. Cancer can affect different parts of the body of a subject. Non-limiting examples of cancer include breast cancer, ovarian cancer, leukemia, lymphoma, glioblastoma, and astrocytoma. In certain embodiments, cancers originating in the brain and/or metastases of cancers from other parts of the body that occur in the brain are of relevance to this disclosure. For example, "glioblastoma" (GB) is a tumor arising from astrocytes that is highly malignant; it is suspected that this is because of rapid reproduction of cells and angiogenesis. A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov, last visited on May 1, 2008. Typically, a patient is given a subsequent chemotherapy regimen because the patient did not show a positive clinical or sub-clinical response to the first line therapy or the first line therapy has stopped.

In one aspect, the term "equivalent" or "biological equivalent" of an antibody or fragment thereof means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody and an antigen with a binding affinity of at least $10^{-6}$ M. In certain aspects, antibodies bind with affinities of at least about $10^{-7}$M, and preferably $10^{-8}$ M, $10^{-9}$M, $10^{-10}$ $10^{-11}$M, or M, $10^{-12}$ M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. Non-limiting examples of linker sequences are known in the art, e.g., GGGGSGGGGSGGGG (SEQ ID NO: 22); the tripeptide EFM; or Glu-Phe-Gly-Ala-Gly-Leu-Val-Leu-Gly-Gly-Gln-Phe-Met (SEQ ID NO: 23)

As used herein, the term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

As used herein, the term "WPRE" or "Woodchuck Hepatitis Virus (WHP) Post-transcriptional Regulatory Element" refers to a specific nucleotide fragment associated with this name and any other molecules that have analogous biological function that share at least 70%, or alternatively at least 80% amino acid sequence identity, preferably 90% sequence identity, more preferably at least 95% sequence identity with the WPRE sequence as shown herein. For example, WPRE refers to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Journal of Virology, Vol. 72, p. 5085-5092, 1998). The analysis using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Journal of Virology, Vol. 73, p. 2886-2892, 1999). In a broad sense, elements such as WPRE that increase the efficiency of amino acid translation by stabilizing mRNAs are also thought to be enhancers.

The term "oncolytic" as used in reference to a virus describes a virus that preferentially infects and kills cancer cells. A "herpes virus" refers to any member of the family herpesviridae, including but not limited to herpes simplex viruses (like HSV-1 and HSV-2). Non-limiting exemplary oncolytic herpes viruses and use thereof are described herein. For example, G207, HSV1716, NV1020, Talimogene laherparvec ("T-VEC" or "Oncovex-GMCSF") have all been tested in clinical trials. See Varghese et al. (2002) *Cancer Gene Therapy.* 9(12):967-978.

List of Abbreviations

CAR: chimeric antigen receptor
IRES: internal ribosomal entry site
MFI: mean fluorescence intensity
MOI: multiplicity of infection
PBMC: peripheral blood mononuclear cells
PBS: phosphate buffered saline
scFv: single chain variable fragment
GB: glioblastoma
BCBM: breast cancer brain metastasis
oHSV: oncolytic herpes simplex virus

MODES FOR CARRYING OUT THE DISCLOSURE

Chimeric Antigen Receptors and Uses Thereof
  Compositions
  The present disclosure provides chimeric antigen receptors (CAR) that bind to wild-type and/or mutant EGFR comprising, or consisting essentially of, an extracellular and intracellular domain. The extracellular domain comprises a target-specific binding element otherwise referred to as the antigen binding domain. The intracellular domain or cytoplasmic domain comprises a costimulatory signaling region and a zeta chain portion. The CAR may optionally further comprise a spacer domain of up to 300 amino acids, preferably 10 to 100 amino acids, more preferably 25 to 50 amino acids. In one aspect, the present disclosure provides a chimeric antigen receptor (CAR) that comprises, or alternatively consists essentially of, or yet further consists of: (a) an antigen binding domain of an anti-EGFR antibody that recognizes either or both wild type and/or mutant Epidermal Growth Factor Receptor (EGFR) ("wt EGFR and/or mutant EGFR"); (b) a hinge domain polypeptide; (c) a costimulatory molecule or polypeptide; and (d) a CD3 zeta signaling domain.

Antigen Binding Domain. In certain aspects, the present disclosure provides a CAR that comprises, or alternatively consists essentially thereof, or yet consists of, an antigen binding domain specific to wild-type and/or mutant EGFR. In one aspect the mutant EGFR is EGFRvIII. In some embodiments, the antigen binding domain comprises, or alternatively consists essentially thereof, or yet consists of the antigen binding domain of a wt and/or mutant EGFR antibody. In further embodiments, the antigen binding domain comprises, or alternatively consists essentially of, or yet further consists of, the heavy chain variable region and light chain variable region of an anti-EGFR antibody that in turn, comprises, or alternatively consists essentially thereof, or yet consists of, the antigen binding domain the anti-EGFR antibody. Light chain and heavy chain variable regions for anti-EGFR antibodies are known in the art and described above.

In some embodiments, the heavy chain variable region of the antibody comprises, or consists essentially thereof, or consists of:

(SEQ ID NO: 24)
Q V Q L Q Q S G S E M A R P G A S V K L P C K A S

G D T F T S Y W M H W V K Q R H G H G P E W I G N

I Y P G S G G T N Y A E K F K N K V T L T V D R S

S R T V Y M H L S R L T S E D S A V Y Y C T R S G

G P Y F F D Y W G Q G T T L T V S S, or an equivalent thereof, or a polynucleotide encoded by the polypeptide:

(SEQ ID NO: 25)
GACATTCTAATGACCCAATCTCCACTCTCCCTGCCTGTCAGTCTTGGAGA

TCAAGCCTCCTACCTGCAAAGGCCAGGCCAGTCTCCAAAGCTCCTGATCT

ACAAAGTTTCCGACCGATTTTACCTGCAAAGGCCAGGCCAGTCTCCAAAG

CTCCTGATCTACAAAGTTTCCGACCGATTTTCTGGGGTCCCAGACAGGTT

CAGTGGCAGTGGATCAGGGACAGATTTCACACTCAAGATCAGCAGAGTAG

AGGCTGAGGATCTGGGAATTTATTACTGCTTTCAAGGTTCACATATTCCT

CCCACGTTCGGAGGGGGGACCAAGCTGGAAATCAAACGTGCGGCC, or an equivalent thereof.

The polypeptide or equivalents of each thereof, can be followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In other aspect, the LC variable region comprises, or alternatively consists essentially of, or yet further consists of:

(SEQ ID NO: 26)
D I L M T Q S P L S L P V S L G D Q A S I S C R S

S Q N I V H N N G I T Y L E W Y L Q R P G Q S P K

L L I Y K V S D R F S G V P D R F S G S G S G T D

F T L K I S R V E A E D L G I Y Y C F Q G S H I P

P T F G G G T K L E I K R A A, or an equivalent thereof, or a polypeptide encoded by the polynucleotide:

(SEQ ID NO: 27)
CAGGTCCAGCTGCAGCAGTCTGGGTCTGAGATGGCGAGGCCTGGAGCTTC

AGTGAAGCTGCCCTGCAAGGCTTCTGGCGACACATTCACCAGTTACTGGA

TGCACTGGGTGAAGCAGAGGCATGGACATGGCCCTGAGTGGATCGGAAAT

ATTTATCCAGGTAGTGGTGGTACTAACTACGCTGAGAAGTTCAAGAACAA

GGTCACTCTGACTGTAGACAGGTCCTCCCGCACAGTCTACATGCACCTCA

GCAGGCTGACATCTGAGGACTCTGCGGTCTATTATTGTACAAGATCGGGG

GGTCCCTACTTCTTTGACTACTGGGGCCAAGGCACCACTCTCACAGTCTC

CTCC, or an equivalent thereof.

The polypeptide or equivalents of each thereof, can be followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

An equivalent thereof comprises an polypeptide having at least 80% amino acid identity to the CAR or a polypeptide that is encoded by a polynucleotide that hybridizes under conditions of high stringency to the complement of a polynucleotide encoding the CAR, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

Alternative embodiments include one or more of the CDRs (e.g., CDR1, CDR2, CDR3) from the LC variable region with appropriate CDRs from other EGFR antibody CDRs. And equivalents of each thereof. Accordingly, and as an example, the CDR1 and CDR2 from the LC variable region can be combined with the CDR3 of another anti-EGFR antibody's LC variable region, and in some aspects, can include an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

Transmembrane Domain. The transmembrane domain may be derived either from a natural or from a synthetic source. Where the source is natural, the domain may be derived from any membrane-bound or transmembrane protein. Transmembrane regions of particular use in this invention may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In one aspect, the transmembrane domain is a CD28 transmembrane domain, non-limiting examples of such are described above. In another aspect, the transmembrane domain is a CD8a transmembrane domain that is linked to a CD8a hinge domain.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the TCR and co-receptors as well as derivatives or variants thereof can function as intracellular signaling domains for use in a CAR. Intracellular signaling domains of particular use in this invention may be derived from CD8a, CD28, FcR, TCR, CD3, CDS, CD22, CD79a, CD79b, CD66d. Since signals generated through the TCR are alone insufficient for full activation of a T cell, a secondary or co-stimulatory signal may also be required. Thus, the intracellular region of a co-stimulatory signaling molecule, including but not limited to CD8a, CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, to may also be included in the cytoplasmic domain of the CAR. In one aspect, the intracellular domain is a CD28 intracellular domain. In another aspect, it is a CD8a intracellular domain.

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, and CD3-zeta protein.

In specific embodiments, the CAR comprises, or alternatively consists essentially thereof, or yet consists of an antigen binding domain of an antibody that binds EGFR and mutant EGFR, a hinge domain, a costimulatory signaling region, and a CD3 zeta signaling domain. In further embodiments, the costimulatory signaling region comprises either or both a CD28 costimulatory signaling region and/or a 4-1BB costimulatory signaling region. The CAR can further comprise a signal polypeptide.

In some embodiments, the CAR can further comprise a detectable marker or purification marker.

Also provided herein is an isolated complex comprising the EGFR CAR and an EGFR protein or a fragment thereof and/or a mutant EGFR protein or a fragment thereof. Yet further provided is an isolated complex comprising the CAR as described herein a cell expressing wt EGFR and/or mutant EGFR.

Polynucleotides and Host Cells

This disclosure also provide isolated nucleic acids encoding the EGFR CAR as described above and the complements of these sequences. The nucleic acids can be DNA, RNA or modified nucleic acids. The nucleic acids can be incorporated into a vector, e.g., a plasmid or viral vector, e.g., a lentiviral vector, an adenoviral vector, or an adeno-associated viral vector. In one aspect the vector is the pCDH vector.

This disclosure also provides isolated host cells (prokaryotic or eukaryotic) cells comprising an EGFR CAR as described herein or a polynucleotide encoding the CAR or their complements or vectors comprising the polynucleotides or their complements. Non-limiting examples of prokaryotic cells include a bacteria, e.g., E. coli. Non-limiting examples of eukaryotic cells include, T cells, NK cells, stem cells, 293 T cells NK-92 cells and NKL cells. The cells can be from any species, e.g., an animal, a mammal, a human, a murine, an equine, a bovine, a feline or a canine. The cells can be isolated from the patient to be treated. They therefore can be autologous or allogeneic. The transformed isolated cells can be used diagnostically or therapeutically.

The isolated nucleic acids can further comprise a detectable marker or a purification marker. The nucleic acids can be combined with a carrier, e.g., a solid support or a pharmaceutically acceptable carrier. They are useful to prepare the CARs as described herein.

Process for Preparing CARs

Aspects of the present disclosure relate to an isolated cell comprising the EGFR CAR and methods of producing such cells. The cell is a prokaryotic or a eukaryotic cell. In one aspect, the cell is a T cell or an NK cell. The eukaryotic cell can be from any preferred species, e.g., an animal cell, a mammalian cell such as a human, an equine, a feline or a canine cell.

In specific embodiments, the isolated cell comprises, or alternatively consists essentially of, or yet further consists of an exogenous CAR comprising, or alternatively consisting essentially of, or yet further consisting of, an antigen binding domain of an antibody that specifically recognized wildtype EGFR and/or mutant EGFR, a hinge domain, a costimulatory molecule (e.g. a CD28 costimulatory signaling region and/or a 4-1BB costimulatory signaling region), and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In certain embodiments, methods of producing EGFR CAR expressing cells are disclosed comprising, or alternatively consisting essentially of: (i) transducing a cell or a population of isolated cells with a nucleic acid sequence encoding the anti-EGFR CAR. The cell can be transduced using the viral vectors as described herein or using technology described in Riet, et al. (2103) Meth. Mol. Biol. 969:187-201 entitled "Nonviral RNA transfection to transiently modify T cell with chimeric antigen receptors for adoptive therapy." In a further aspect, the method further comprises selecting for a cell that expresses the CAR by selected cells that express the EGFR binding domain. Selection can be accomplished by use of anti-EGFR antibodies to selectively recognize and bind the EGFR binding domains expressed on the surface of the cells. In some embodiments, the isolated cells are T-cells, an animal T-cell, a mammalian T-cell, a feline T-cell, a canine T-cell or a human T-cell, thereby producing EGFR CAR T-cells. In certain embodiments, the isolated cell is an NK-cell, e.g., an animal NK-cell, a mammalian NK-cell, a feline NK-cell, a canine NK-cell or a human NK-cell, thereby producing EGFR CAR NK-cells.

Sources of T or NK Cells. Prior to expansion and genetic modification of the T cells of the invention, a source of T cells is obtained may be obtain from a subject or a culture. T cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include, but are not limited to Life Technologies Dynabeads® system; STEMcell Technologies EasySep™, RoboSep™, RosetteSep™, SepMate™; Miltenyi Biotec MACS™ cell separation kits, and other commercially available cell separation and isolation kits. Particular subpopulations of immune cells may be isolated through the use of beads or other binding agents available in such kits specific to unique cell surface markers. For example, MACS™ CD4+ and CD8+ MicroBeads may be used to isolate CD4+ and CD8+ T-cells.

Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™) BCL2 Jurkat (ATCC® CRL-2899™), Neo Jurkat (ATCC® CRL-2898™); and, for NK cells, lines NK-92 (ATCC® CRL-2407™), NK-92MI (ATCC® CRL-2408™).

Vectors. CARs may be prepared using vectors. The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes.

Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In some embodiments, the isolated nucleic acid sequence encodes for a CAR comprising, or alternatively consisting essentially of, or yet further consisting of an antigen binding domain of an anti-EGFR antibody that recognizes either or both wt and mutant EGFR, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding an antigen binding domain of an anti-EGFR antibody followed by a hinge region, a CD28 costimulatory signaling region and/or a 4-1BB costimulatory signaling region followed by a CD3 zeta signaling domain. In a further aspect, the antigen binding domain comprises a HC variable region and a LC variable region that is optionally connected by a linker polypeptide.

In some embodiments, the isolated nucleic acid comprises a polynucleotide conferring antibiotic resistance.

In some embodiments, the isolated nucleic acid sequence is comprised in a vector. In certain embodiments, the vector is a plasmid. In other embodiments, the vector is a viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome, the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Packaging vector and cell lines. CARs can be packaged into a retroviral packaging system by using a packaging vector and cell lines. The packaging plasmid includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging plasmids and retroviral vectors expressing the EGFR are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the invention this transiently transfected first population of cells is then cocultivated with mammalian target cells, for example human lymphocytes, to transduce the target cells with the foreign gene at high efficiencies. In yet another method of the invention the supernatants from the above described transiently transfected first population of cells are incubated with mammalian target cells, for example human lymphocytes or hematopoietic stem cells, to transduce the target cells with the foreign gene at high efficiencies.

In another aspect, the packaging plasmids are stably expressed in a first population of mammalian cells that are capable of producing virus, such as human embryonic kidney cells, for example 293 cells. Retroviral or lentiviral vectors are introduced into cells by either cotransfection with a selectable marker or infection with pseudotyped virus. In both cases, the vectors integrate. Alternatively, vectors can be introduced in an episomally maintained plasmid. High titer recombinant retrovirus-containing supernatants are produced.

Activation and Expansion of T or NK Cells. Whether prior to or after genetic modification of the T cells or NK cells to express a desirable CAR, the T cells or NK cells can be activated and expanded generally using generally known methods such as those described in U.S. Pat. Nos. 6,352,694; 6,534,055; 6,905,680; 6,692,964; 5,858,358; 6,887,466; 6,905,681; 7, 144,575; 7,067,318; 7, 172,869; 7,232,566; 7, 175,843; 5,883,223; 6,905,874; 6,797,514; 6,867,041. Methods of activating relevant cells are well known in the art and can be readily adapted to the present application; an exemplary method is described in the examples below. Stimulation with the EGFR antigen ex vivo can activate and expand the selected CAR expressing T-cell subpopulation. Alternatively, the T-cells may be activated in vivo by interaction with EGFR antigen. Thus, in a further aspect, this disclosure provides an isolated expanded population of cells expressing an EGFR CAR.

Isolation methods for use in relation to this disclosure include, but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 Dynabeads® may be used to activate and expand a population of isolated T-cells.

As disclosed above, chimeric antigen receptors comprise an antigen recognition moiety and a cell activation moiety. Aspects of the present disclosure related to a chimeric antigen receptor (CAR) comprising an antigen binding domain specific to wildtype and mutant EGFR.

Methods of Use

Therapeutic Application. The CAR T-cells and NK cells of the present disclosure can be used to treat tumors and cancers that express EGFR, such as gliobastoma. The EGFR CAR cells of the present disclosure can be administered either alone or in combination with diluents, known anti-cancer therapeutics (chemotherapeutics, surgery and/or radiation), and/or with other components such as cytokines or other cell populations that are immunostimulatory. The methods of this disclosure can be first-line, second-line, third-line or fourth line therapy.

Method aspects of the present disclosure relate to methods for inhibiting the growth of a tumor in a subject in need thereof and/or for treating a cancer patient in need thereof. In some embodiments, the tumor is a solid tumor. In some embodiments, the tumors/cancer is glioblastoma or a glioblastoma stem cell. In certain embodiments, these methods comprise, or alternatively consist essentially of, or yet further consist of, administering to the subject or patient an effective amount of the isolated cell as described herein, e.g., the isolated cell that comprises an EGFR CAR. In still further embodiments, the isolated cell is a T-cell or an NK cell. In some embodiments, the isolated cell is autologous to the subject or patient being treated. In a further aspect, the tumor expresses EGFR antigen and the subject has been selected for the therapy by a diagnostic, such as the one described herein. In a further aspect, the isolated cells are directly injected or infused into the brain of the subject to inhibit the growth of a gliobastoma or glioblastoma stem cells.

Pharmaceutical compositions comprising the EGFR CAR of the present invention may be administered in a manner appropriate to the disease to be treated or prevented. Any appropriate method of administration can be used, e.g., direct injection and/or systemically such as by intravenous injection. The quantity and frequency of administration will be determined by such factors as the condition of the patient, and the type and severity of the patient's disease, although appropriate dosages may be determined by clinical trials. The method of inhibiting the growth of a tumor can be applied to a subject including but not limited to human, dog, cat, horse, and other species.

In one embodiment, the disclosure provides a method for determining if a patient is likely to respond or is not likely to EGFR CAR therapy, the method comprising, or alternatively consisting essentially of, or yet further consisting of contacting a tumor sample isolated from the patient with an effective amount of an EGFR antibody and detecting the presence of any antibody bound to the tumor sample, wherein the presence of antibody bound to the tumor sample indicates that the patient is likely to respond to the EGFR CAR therapy and the absence of antibody bound to the tumor sample indicates that the patient is not likely to respond to the EGFR CAR therapy. In another embodiment, the method further comprises administering an effective amount of the EGFR CAR therapy to the patient that is determined likely to respond to the EGFR CAR therapy. In this method, the patient can suffer from a brain cancer. In some embodiments, this brain cancer is glioblastoma or a metastasis of another cancer (e.g. breast cancer). In one aspect, the sample is obtained from a subject that is diagnosed as having, suspected as having, or at risk of having cancer.

In one aspect, the detection comprises, or alternatively consists essentially of, or yet further consists of one or more of immunohistochemistry (IHC), Western blotting, Flow cytometry or ELISA.

In one aspect, the method comprises, or alternatively consists essentially of, or yet further consists of isolating the biological sample from the subject. In a further aspect, T cells or NK cells are isolated from the subject, transduced with an isolated nucleic acid encoding the EGFR CAR and an expanded population of transduced cells are prepare for administration to the subject using a method as described herein.

In one aspect, the subject is a mammal, such as a human patient.

Compositions and Carriers

Additional aspects of the invention relate to compositions comprising a carrier and one or more of the products—e.g., EGFR CAR, an isolated cell comprising a EGFR CAR, an isolated nucleic acid encoding the EGFR CAR or their complements and/or a vector comprising the isolated nucleic acid. The carriers can be solid carriers or liquid carriers such as pharmaceutically acceptable carriers.

Briefly, pharmaceutical compositions of the present invention including but not limited to any one of the claimed compositions that in one aspect comprises a cell population as described herein, in combination with one or more pharmaceutically or physiologically acceptable carriers, diluents or excipients or solid supports. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Briefly, pharmaceutical compositions of the present invention including but not limited to any one of the claimed compositions as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

Combination Therapies

Aspects of this disclosure relate to combination therapies involving the EGFR CAR expressing cells disclosed herein and an oncolytic herpes simplex virus. Clinical studies have demonstrated that oncolytic herpes viruses, when administered alone, work with limited efficacy. The experiments and disclosure provided herein demonstrate promising results for EGFR CAR expressing cells. Applicants have found that the administration of both EGFR CAR expressing cells and an oncolytic herpes simplex has a synergistic effect. Not to be bound by theory, it is suspected that EGFR CAR expressing cells may facilitate the destruction of the tumor tissue structure making cancer cells more accessible for infection and destruction by the oncolytic herpes viruses.

In some embodiments, the EGFR CAR expressing cells contemplated for use in a combination therapy are isolated immune cells, optionally selected from T cells or NK cells. In some embodiments, these EGFR CAR expressing cells are irradiated. In some embodiments, the EGFR CAR expressing cells are irradiated at a dose between 1 and 10000 cGy, such as (but not limited to) greater than, less thank, or about 1 cGy, 5 cGy, 10 cGy, 50 cGy, 100 cGy, 500 cGy, 1000 cGy, 5000 cGy, or 10000 cGy. In some embodiments, the irradiation dose is optimize the proliferation of the EGFR CAR expressing cells while maintaining their full activity up to greater than or about 12, 24, 36, 48, 60, 72, 84, 96, or more hours. In some embodiments, the EGFR CAR expressing cells are modified (through irradiation or other means) in order not to eradicate or eliminate oHSV.

In some embodiments the oncolytic herpes simplex virus is one or more of the oncolytic herpes viruses that have undergone clinical trials and are disclosed herein above. In some embodiments, the oncolytic herpes simplex virus is derived from HSV-1 or HSV-2.

In some embodiments, the EGFR CAR expressing cells are administered at the same time, before, or after the oncolytic herpes simplex virus. In some embodiments, the EGFR CAR expressing cells are administered first. In other embodiments, the oncolytic herpes simplex virus is administered first. In some embodiments, the EGFR CAR expressing cells are administered in single or multiple doses. In some embodiments the oncolytic herpes simplex viruses is administered in single or multiple doses. In one embodiment, the EGFR CAR expressing yells are administered first followed by administration of the oncolytic herpes simplex viruses over one or more days.

Kits

Further provided herein are kits comprising one or more of the EGFR CAR as described herein, an isolated nucleic acid encoding the EGFR CAR or their complements, a vector comprising the nucleic acids, an isolated cell as described herein, or an isolated complex as described herein.

The following examples are intended to illustrate and not limit this disclosure.

Experiment I—Generation and Characterization of EGFR CAR Expressing Cells

Cell Culture

Human GB cell lines [Gli36DeltaEGFR (Gli36dEGFR), U251, and LN229] and human patient-derived GB stem cells (GB1123, GB30, GB83, and GB326) (Mao, P. et al. (2013) Proc Natl Acad Sci. USA 110:8644-8649) were used in this study. GB84V3SL, GB157V3SL, and GB19 were also established from GB patients using the same protocol (Mao, P. et al. (2013) Proc Natl Acad Sci. USA 110:8644-8649). All GB cell lines, 293T cells and Phoenix cells were cultured in DMEM (Invitrogen, Grand Island, N.Y.) supplemented with 10% FBS, penicillin (100 U/ml), and streptomycin (100 µg/ml). GB stem cells were cultured in DMEM-F-12 medium supplemented with bFGF (20 ng/ml), EGF (20 ng/ml), Glutamax (1:100), B27 (1:100), heparin (5 µg/ml), penicillin (100 U/ml), and streptomycin (100 µg/ml). All stocks of the above antibiotics and cytokine stocks were purchased from Invitrogen. Human NK cell lines NK-92 and NKL were maintained in RPMI-1640 (Invitrogen) supplemented with 20% FBS, penicillin (100 U/ml), streptomycin (100 µg/ml) and 150 IU/mL recombinant human (rh) IL-2 (Hoffman-La Roche Inc., Nutley, N.J.).

Mice

Six to eight-week-old NOD.Cg-Prkdc$^{scid}$ Il2rg$^{tm1Wjl}$i/SzJ mice (NSG) mice were obtained from Jackson Laboratories (Bar Harbor, Me.). All animal work was approved by The Ohio State University Animal Care and Use Committee and the methods were carried out in accordance with the approved guidelines. Mice were monitored frequently for GB disease progression, and sacrificed when they became moribund with neurologic impairments and obvious weight loss.

Generation of Anti-EGFR CAR Lentiviral Construct

The anti-EGFR single chain variable fragment (scFv) was derived from a hybridoma cell line that produces mouse monoclonal antibody 528 recognizing both wtEGFR and EGFRvIII (Hayashi, H. et al. (2004) Cancer Immunology, Immunotherapy:CII 53:497-509; Humphrey, P. A. et al. (1990) Proc Natl Acad Sci. USA 87:4207-4211). The coding domain sequences for variable regions of heavy (VH) and light (VL) chains were amplified separately and assembled using a linker by overlapping PCR reaction. The VH-linker-VL fragment was incorporated in frame with CD28-CD3ζ portion (Pule, M. A. et al. (2005) Mol Ther. 12:933-941) that was incised from a retroviral vector. The entire anti-EGFR-scFv-CD28-CD3ζ fragment was then ligated into a lentiviral vector designated pCDH-CMV-MCS-EF1-copGFP (pCDH, System Biosciences, Mountain View, Calif.) to generate a pCDH-EGFR-scFv-CD28-CD3ζ (pCDH-EGFR-CAR) construct.

Lentivirus Production and Transduction of NK Cells

To produce lentiviruses for infection of NK cells (NK-92 and NKL), 293T cells were co-transfected with the aforementioned pCDH-EGFR-scFv-CD28-CD3ζ plasmid or a mock pCDH vector together with the packaging constructs pCMV-VSVG and pCMV-DR9 using calcium phosphate transfection reagent (Promega, Madison, Wis.). The transfection and infection procedures were modified from a previously published protocol (Chu, J. et al. (2014) Leukemia 28:917-927).

Generation of GB19 Stem Cells Stably Expressing wtEGFR or EGFRvIII

Phoenix cells were co-transfected with the pBABE-wtEGFR (a wtEGFR expression construct), or pBABE-EGFRvIII (an EGFRvIII expression construct) or a pBABE empty vector together with Sara3 packaging plasmid using calcium phosphate transfection reagent (Promega, Madison, Wis.). Two days after transfection, the infectious supernatants were harvested to infect GB19 stem cells in the presence of polybrene (8 μg/mL). Retrovirus was produced in serum-free DMEM-F12 medium for infection of GB19 stem cells, and GFP positive GB19-wtEGFR or GB19-EGFRvIII cells were then sorted using a FACS Aria II cell sorter (BD Biosciences, San Jose, Calif.).

Flow Cytometry

To evaluate NK cell surface expression of EGFR-CAR, transduced NK cells were washed with PBS containing 4% BSA, and incubated with biotin-labeled goat anti-mouse $F(ab')_2$ polyclonal antibody or normal polyclonal goat IgG antibody (Jackson ImmunoResearch, West Grove, Pa.) as an isotype control as described previously (Chu, J. et al. (2014) Leukemia 28:917-927). Then cells were washed again and stained with allophycocyanin (APC)-conjugated streptavidin (Jackson ImmunoResearch, West Grove, Pa.). To determine wtEGFR and/or EGFRvIII expression on the surface of GB cells, the cells were incubated with mouse monoclonal anti-human EGFR (clone H11, DAKO, Carpinteria, Calif.) which recognizes both wild-type EGFR and its mutant form (EGFRvIII), followed by staining with APC conjugated goat anti-mouse IgG second antibody.

Reverse Transcription PCR

To detect EGFR mRNA expression in glioma cells, RNA was extracted from the cell lines with RNeasy Mini Kit (Qiagen, Hilden, Germany) and quantified with NanoDrop (Thermo Fisher, Wilmington, Del.). Reverse transcript was produced using M-MLV reverse transcriptase (Invitrogen, Grand Island, N.Y.), and PCR was conducted with GoTaq® Flexi DNA Polymerase (Promega, Madison, Wis.). The forward primer is TGACTCCGTCCAGTATTGATCG (SEQ ID NO: 28), and the reverse primer is GCCCTTCGCACTTCTTACACTT (SEQ ID NO: 29). The PCR reaction parameters are 95° C. 5 min, 35 cycles at 95° C. 40 s, 55° C. 40 s, 72° C. 1 min, and final extension at 72° C. for 10 min.

Cytotoxicity Assay

A standard 4-h $^{51}Cr$ release assay was performed as described previously (Yu, J. et al. (2010) Blood 115:274-281). Briefly, target cells were labeled with $^{51}Cr$ and co-cultured with modified NK cells at various effector/target ratios (E/T) in the wells of 96-well V-bottom plates at 37° C. for 4 h. Supernatants were harvested and transferred into scintillation vials containing a liquid scintillation cocktail (Fisher Scientific, Waltham, Mass.), and the release of $^{51}Cr$ was measured on Beckman Liquid Scintillation Counter LS-6500. Target cells incubated in complete medium or 1% SDS were used to determine spontaneous or maximal $^{51}Cr$ release, respectively. Percentage of specific cell lysis was calculated using the standard formula: 100×(cpm experimental release−cpm spontaneous release)/(cpm maximal release−cpm spontaneous release).

IFN-γ Release Assay $1×10^6$ target cells were incubated with equal numbers of NK effector cells in 96-well V bottom plates for 24 h. Cell-free supernatants were assayed for IFN-γ secretion by enzyme-linked immunosorbent assay (ELISA) using a kit from R&D Systems (Minneapolis, Minn.) in accordance with the manufacturer's protocol. Data depicted in figures represent mean values of triplicate wells from one of three representative experiments with similar results.

Treatment of Orthotopic Human GB30 Xenografts in NSG Mice

GB30 GB stem cells were retrovirally transduced with Pinco-pGL3-luc/GFP virus expressing firefly luciferase (FFL) as previously described (He, S. et al. (2013) Blood 121:4663-4671). GFP positive cells were sorted using a FACS Aria II cell sorter (BD Biosciences, San Jose, Calif.), and were designated "GB30-FFL" cells. NSG mice were anesthetized and fixed in a stereotactic apparatus, a burr hole was drilled 2 mm lateral and 1 mm anterior to the bregma to a depth of 3.25 mm, and $5×10^4$ GB30-FFL cells in 2 μl Hank's buffered salt solution (HBSS) were implanted. On Day 7, the mice were intracranially injected with $2×10^6$ effector cells (non-irradiated), i.e. EGFR-CAR-transduced NK-92 cells (NK-92-EGFR-CAR) or mock-transduced NK-92 cells (NK-92-EV) in 5 μl HBSS. Mice treated with 5 μl HBSS only were used as control. Mice were monitored daily and euthanized when showing signs of morbidity. Two weeks after GB30-FFL cell inoculation, the mice were intraperitoneally (i.p.) infused with D-luciferin (150 mg/kg body weight; Gold Biotechnology, St. Louis, Mo.), anesthetized with isoflurane, and imaged using In Vivo Imaging System (IVIS-100, PerkinElmer, Waltham, Mass.) with living image software (PerkinElmer).

Treatment of Orthotopic Human U251 Xenografts in NSG Mice

U251 GB cells were retrovirally transduced with Pinco-pGL3-luc/GFP virus expressing firefly luciferase (FFL) as previously described (He, S. et al. (2013) Blood 121:4663-4671). GFP positive cells were sorted using a FACS Aria II cell sorter (BD Biosciences, San Jose, Calif.), and were designated "U251-FFL" cells. NSG mice were anesthetized and fixed in a stereotactic apparatus, and a burr hole was drilled 2 mm lateral and 1 mm anterior to the bregma to a depth of 3.25 mm, through which $10^5$ U251-FFL cells in 2 μl Hank's buffered salt solution (HBSS) were inoculated on day 0. On day 10, 40, 70 the mice were intracranially injected with $2×10^6$ effector cells, i.e. EGFR-CAR-transduced NK-92 cells (NK-92-EGFR-CAR) or mock-transduced NK-92 cells (NK-92-EV) in 5 μl HBSS. Mice treated with 5 μl HBSS only were used as control. Mice were monitored daily and euthanized when showing signs of morbidity. On day 100 after U251-FFL cell inoculation, the mice were intraperitoneally (i.p.) infused with D-luciferin (150 mg/kg body weight; Gold Biotechnology, St. Louis, Mo.), anesthetized with isoflurane, and imaged using In Vivo Imaging System (IVIS-100, PerkinElmer, Waltham Mass., USA) with living image software (PerkinElmer).

Organ and Tissue Distribution Assays of NK-92-EGFR-CAR Cells $2×10^6$ NK-92 EGFR-CAR cells were intracranially injected into three GB30-bearing mice 7 days after tumor implantation. Three days later, all mice were sacrificed and liver, lung, spleen, bone marrow, blood, and brain were harvested. Half of organs or tissues were used for genomic DNA isolation with a DNA isolation kit (Invitrogen, Carlsbad, Calif.), and PCR was performed with primers to amplify the EGFR-CAR scFv region. The PCR forward primer was AGGTCACTCTGACTGTAGACA (SEQ ID NO: 30), and the reverse primer was GTTCATGTAGT-CACTGTGCAG (SEQ ID NO: 31). The PCR reaction parameters were 95° C. 5 min, 35 cycles at 95° C. 40 s, 55° C. 40 s, 72° C. 1 min, and final extension at 72° C. for 10 min.

The other half of organs or tissues was used to isolate mononuclear immune cells using density gradient centrifugation in Percoll (GE Healthcare, Pittsburgh, Pa.). The collected immune cells were surface stained with V450 mouse anti-human CD3e and APC mouse anti-human CD56 antibodies (eBioscience, San Diego, Calif.) to determine the presence of NK-92-EGFR-CAR cells in a specific organ or tissue.

Statistical Analysis

Unpaired Student's t test was utilized to compare two independent groups for continuous endpoints if normally distributed. One-way ANOVA was used when three or more independent groups were compared. For non-normally distributed endpoints, such as in vivo bioluminescence intensity, a Kruskal-Wallis test was utilized to compare the median of NK-92-EGFR-CAR group to NK-92-EV and HBSS-treated groups. For survival data, Kaplan-Meier curves were plotted and compared using a log-rank test. All tests are two-sided. P values were adjusted for multiple comparisons using Bonferroni method. P values less than 0.05 were considered significant.

Generation of 293T Cell Lines Stably Expressing wtEGFR or EGFRvIII. Phoenix cells were co-transfected with the pBABE-wtEGFR (wt EGFR expression construct), pBABE-EGFRvIII (EGFRvIII expression construct), or pBABE empty vector together with Sara3 packaging plasmid using calcium phosphate transfection reagent (Promega, Madison, Wis., USA). Two days after transfection, supernatants were harvested to infect 293T cells in the presence of polybrene (8 µg/mL). GFP positive cells were sorted using a FACS Aria II cell sorter (BD Biosciences, San Jose, Calif., USA).

Lentivirus production and transduction of primary NK cells. Lentiviruses were produced as previously described (Chu, J. et al. (2014) Leukemia 28:917-927) and were concentrated by ultracentrifuge at 20,000 g for 90 minutes at 4° C. and resuspended with 1× PBS. Human primary NK cells were isolated from peripheral blood leukopacks of healthy donors (American Red Cross, Columbus, Ohio) as described previously (He, S. et al. (2013) Blood 121:4663-4671) and infected with lentiviruses (MOI=2.5) by three consecutive rounds of centrifugation at 2000 rpm and 32° C. for 2 h (gentle resuspension between rounds), and GFP positive cells were sorted using a FACS Aria II cell sorter (BD Biosciences, San Jose, Calif., USA). Standard 4-h $^{51}$Cr release assays were performed to evaluate the cytotoxicity of primary NK cells transduced with EGFR-CAR plasmid or control vector against U251 and Gli36dEGFR GB cell lines and GB30 and GB157V3SL patient-derived GB stem cells.

Antibody blocking assay. GB30 stem cells and U251 cell line were pretreated with 10 µg/ml EGFR neutralizing antibody (clone 528, EMD Millipore, Billerica, Mass.) or an isotype-matched antibody at 37° C. for 30 minutes. Standard 4-h 51Cr release assays were then performed to evaluate cytotoxicity of NK-92-EGFR-CAR cells and control cells against the 528 antibody- or IgG-pretreated target cells. IFN-γ secretion was also quantified by ELISA on cell-free supernatants after 1×10$^6$ target cells pretreated with 528 antibody- or IgG were incubated with an equal number of NK-92-EGFR-CAR cells or control cells in 96-well V bottom plates for 24 h.

Hematoxylin and Eosin (H&E) staining of brain sections of GB30-bearing mice. NSG mice were intracranially injected with 5×10$^4$ GB30 cells on day 0. On day 7, the mice were intracranially injected with 2×10$^6$ NK-92-EGFR-CAR cells in 5 µl HBSS. On day 10, the mice were sacrificed and brain tissues were harvested and immersed in 10% formalin for 24 h, and then brains were embedded in paraffin and processed for H&E staining.

Results

Figure 1B:

Expression of EGFR or EGFRvIII on GB Cell Lines and Patient-Derived GB Stem Cells To assess the surface expression of wtEGFR or EGFRvIII on a panel of GB cell lines and patient-derived GB stem cells, intact cells were stained with an EGFR-specific antibody that recognizes both wtEGFR and EGFRvIII, followed by flow cytometric analysis. As shown in FIG. 1A, EGFR was expressed on the surface of GB cell lines (Gli36dEGFR, U251, and LN229), patient-derived GB mesenchymal (MES) stem cells (GB30, GB83, GB1123 and GB326) and GB proneural (PN) stem cells (GB84V3S and GB157V3SL). To further address whether wtEGFR or EGFRvIII transcript was expressed in these cells, Applicants carried out RT-PCR with specific primers and observed that wtEGFR mRNA was expressed in two GB cell lines, U251 and LN229. EGFRvIII mRNA was detectable in the GB cell line Gli36dEGFR, and in six GB stem cells that Applicants generated from GB patients (Mao, P. et al. (2013) Proc Natl Acad Sci. USA 110:8644-8649): GB30, GB83, GB1123, GB326, GB84V3SL and GB157V3SL (FIG. 1B). In contrast, one GB stem cell, GB19 (proneural), and the two NK cell lines, NK-92 and NKL, had no detectable EGFR expression by flow cytometric analysis or RT-PCR (FIGS. 1A, 1B).

Generation of NK-92 and NKL NK Cells Expressing EGFR-CAR

Figure 2A:
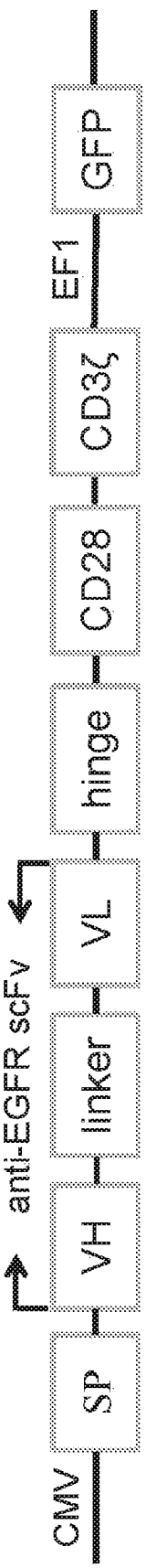
FIGS. 2A-2B show generation of an EGFR-specific CAR and detection of its expression on CAR-transduced NK cells.
Figure 2B:
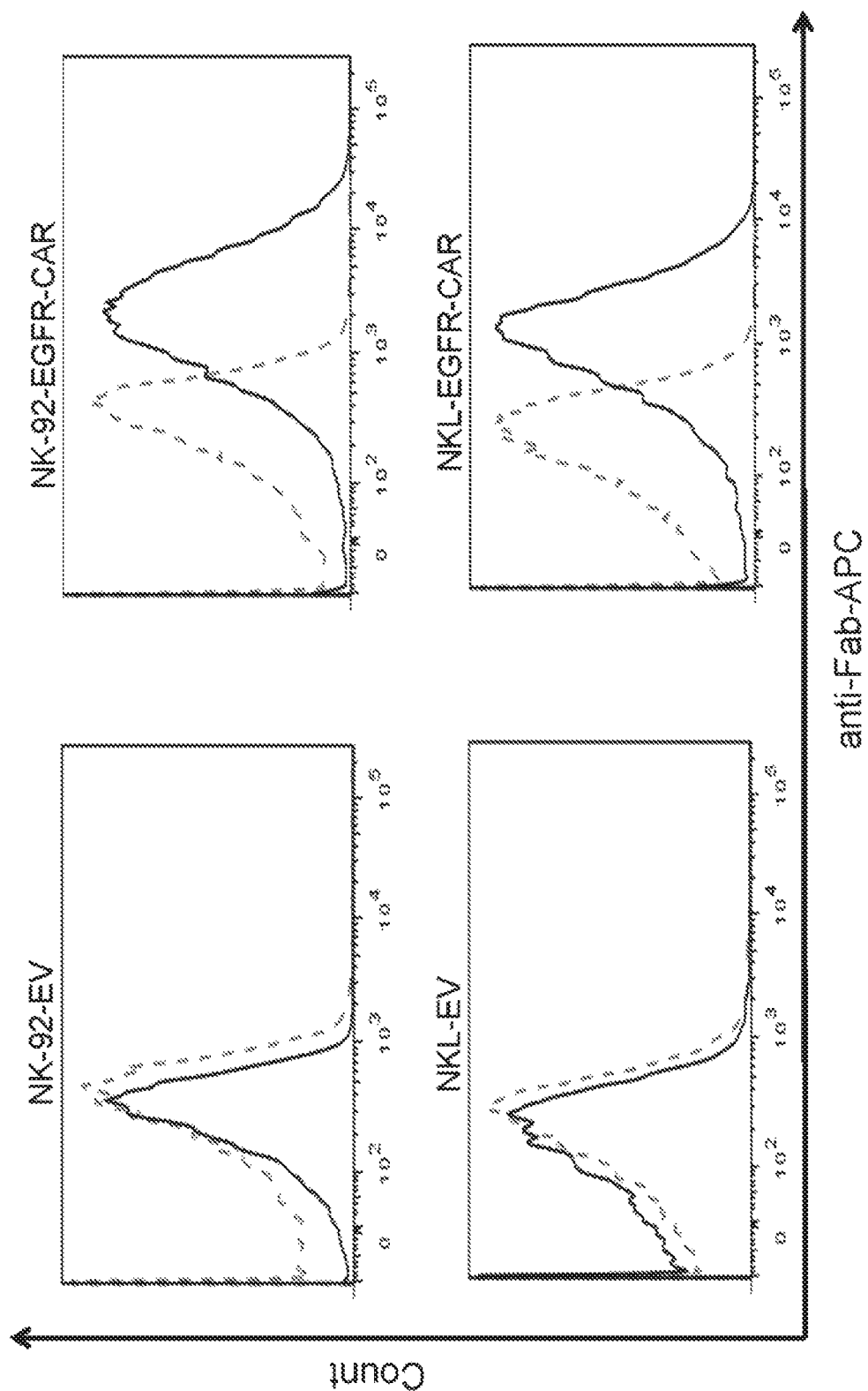

A second-generation EGFR-specific CAR construct was generated in a pCDH lentiviral vector backbone. This construct sequentially contains a signal peptide (SP), a heavy chain variable region (VH), a linker, a light chain variable region (VL), a hinge, CD28 transmembrane and intracellular domain, and CD3ζ signaling moiety (FIG. 2A). NK-92 and NKL cell lines were transduced with the EGFR-CAR construct to generate NK-92 EGFR-CAR and NKL EGFR-CAR cells respectively. The transduced cells were sorted for the expression of GFP expressed by the vector. To validate cell surface expression of EGFR-CAR on the transduced NK-92 and NKL cells, flow cytometric analysis was performed using a goat anti-mouse F(ab')$_2$ antibody that recognized the scFv portion of anti-EGFR. The data from FIG. 2B showed an obvious increase in cell surface EGFR-CAR expression in EGFR-CAR-transduced NK-92 and NKL cells over those transduced with empty vector, the latter of which had undetectable EGFR-CAR expression.

Figure 3:
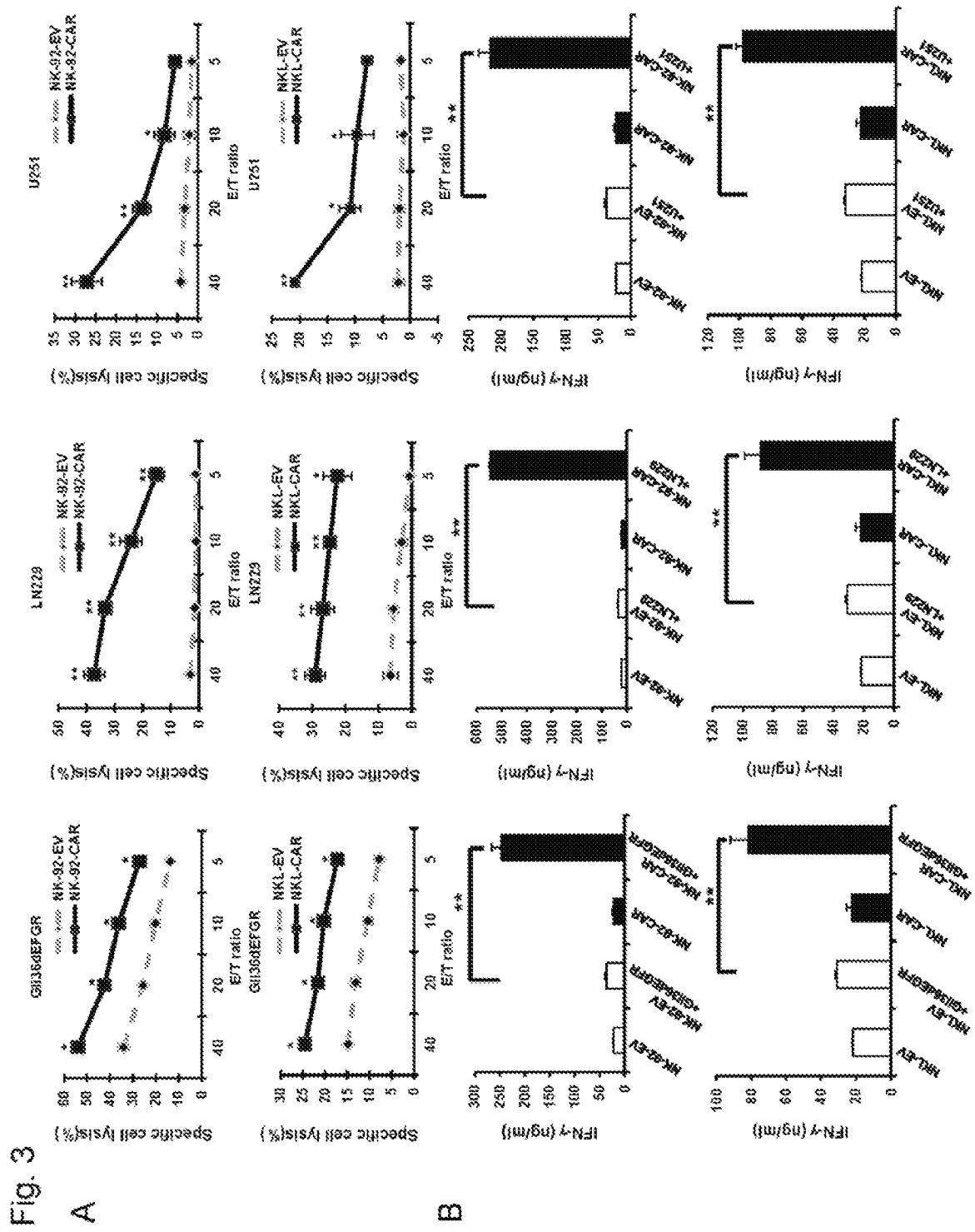
FIGS. 3A-3B show EGFR-CAR-modified NK-92 and NKL cells recognize and kill EGFR$^+$ GB cell line cells.

Efficacy of EGFR-CAR-Modified NK Cell Cytotoxicity and IFN-γ Production Against EGFR$^+$ GB Cell Lines The cytotoxicity of EGFR-CAR- and mock-transduced NK cells was assessed against GB cells using a standard chromium release assay at varying ratios of effector cells to target cells. FIGS. 3A-3B show significantly enhanced cytotoxicity of NK-92 EGFR-CAR cells against EGFR$^+$ Gli36dEGFR, U251, and LN229 cells compared to control NK-92-EV cells (FIG. 3A, upper panels) Similar data were observed in experiments using the NKL cell line transduced with EGFR-CAR (FIG. 3A, lower panels). Human primary NK cells transduced with EGFR-CAR also showed significantly more potent cytotoxicity than control cells against EGFR$^+$ Gli36dEGFR and U251 GB cell lines (FIG. 8A). To determine if the observed enhanced cytolytic activity was accompanied by a similar significant increase in IFN-γ secretion, Applicants co-cultured EGFR-CAR NK-92 cells with EGFR glioma cells (Gli36dEGFR, U251, and LN229) cells for 24 h and measured IFN-γ production by ELISA. As shown in FIG. 3B, both EGFR-CAR-modified and mock-transduced NK-92 or NKL cells spontaneously produced low or negligible levels of IFN-γ when incubated alone. Culturing these cells with EGFR+ glioma cells (Gli36dEGFR, U251 and LN229) induced IFN-γ in both EGFR-CAR and mock-transduced NK-92 or NKL cell lines, with significantly higher levels of IFN-γ produced by EGFR-CAR-modified NK-92 or NKL cells than by mock-transduced NK-92 or NKL cells, respectively (FIG. 3B). These results are in agreement with the aforementioned cytotoxicity data, and together indicate that modification with EGFR-CAR can significantly enhance NK cell effector functions in response to EGFR+ glioma cells.

Figure 4:
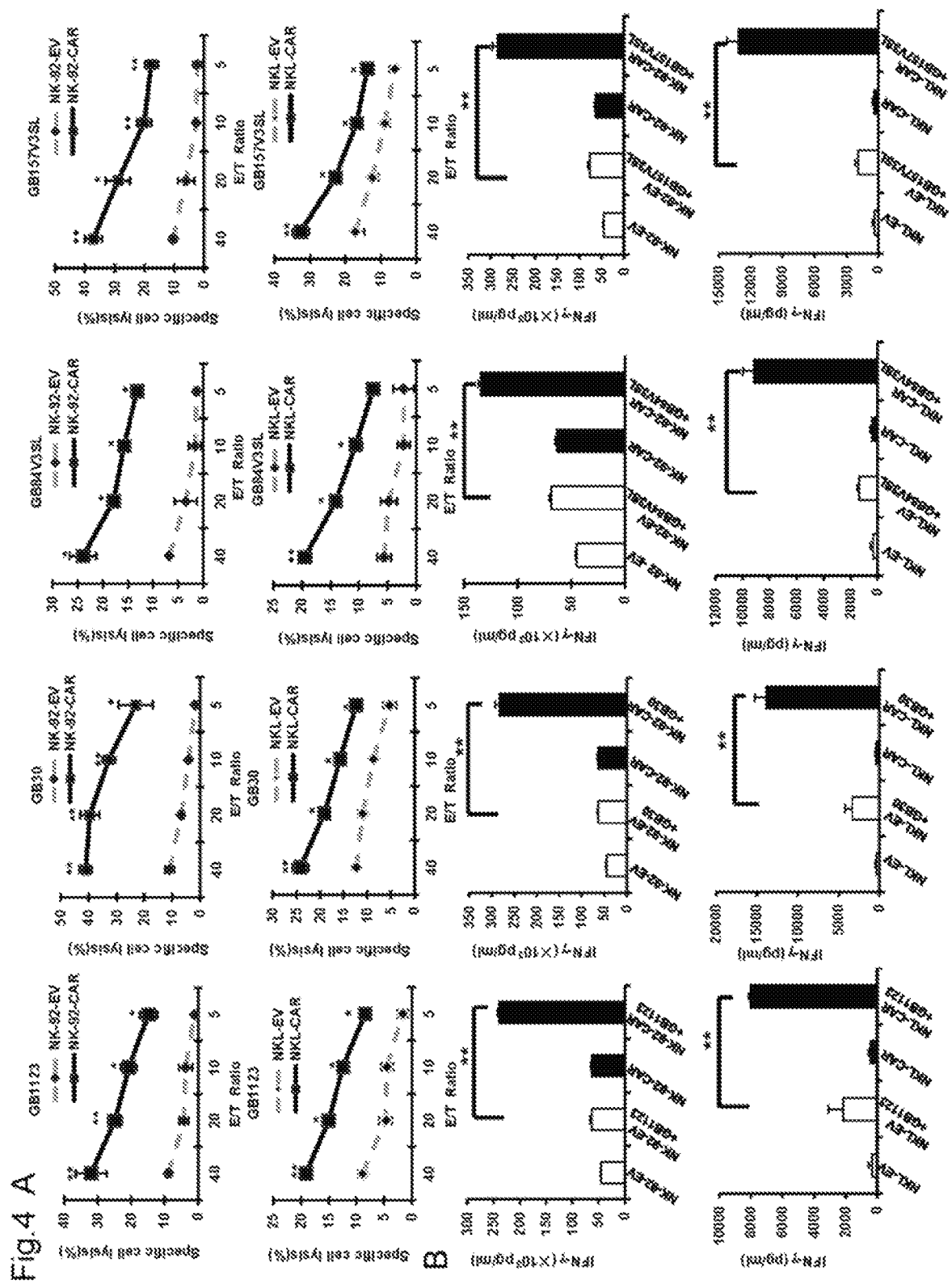
FIGS. 4A-4B show EGFR-CAR-modified NK-92 and NKL cells display enhanced lysis of EGFR$^+$ GB stem cells.

Efficacy of EGFR-CAR-Modified NK Cell Cytotoxicity and IFN-γ Production Against EGFR+ GB Stem Cells Derived from GB Patients Applicants next assessed the capacity of EGFR-CAR-modified NK-92 and NKL cells to lyse patient-derived GB stem cells with surface expression of endogenous EGFR protein. EGFR-CAR-transduced NK-92 cells demonstrated a significantly enhanced ability to kill EGFR+ GB mesenchymal stem cells (GB1123 and GB30) and GB proneural stem cells (GB157V3SL and GB84V3SL) when compared to mock-transduced NK cells (FIG. 4A, upper panels). Similar data were observed in experiments repeated using NKL cells transduced with EGFR-CAR (FIG. 4A, lower panels). Primary NK cells transduced with EGFR-CAR also showed significantly more potent cytotoxicity than control cells against patient-derived stem cells GB30 and GB157V3SL, which express EGFRvIII (FIG. 8B). Likewise, EGFR-CAR-transduced NK-92 and NKL cells produced significantly more IFN-γ when co-cultured with EGFR+ GB stem cells and compared to mock-transduced NK-92 (FIG. 4B, upper panels) and NKL cells (FIG. 4B, lower panels). These results indicate that modification of NK cells with an EGFR-CAR can significantly enhance NK cell cytotoxicity and IFN-γ production against EGFR+ GB stem cells compared to unmodified NK cell controls.

Figure 5:
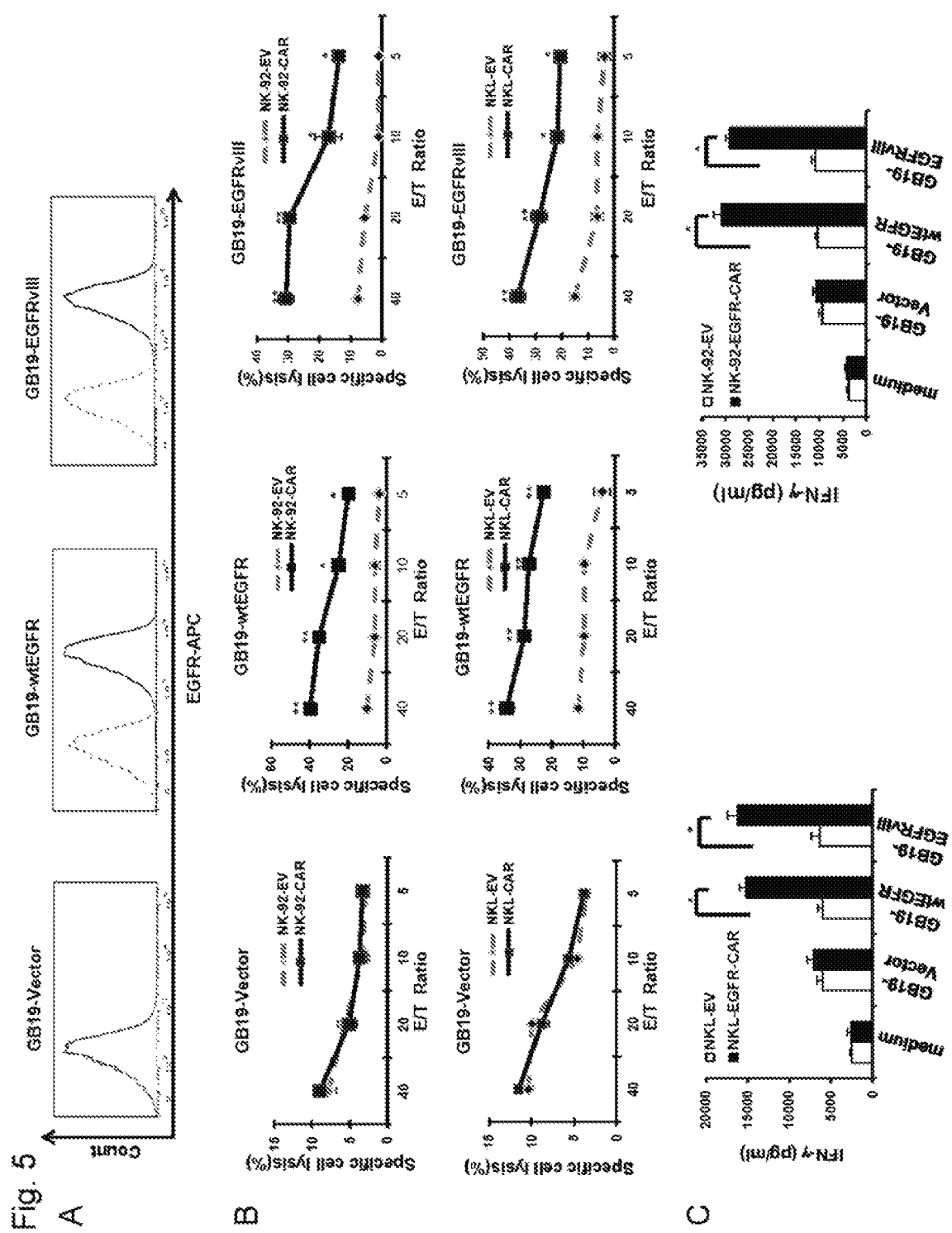
FIGS. 5A-5C show enhanced target recognition of NK-92-EGFR-CAR cells depends on expression of EGFR on cell surface.

Enhanced Cytotoxicity and IFN-γ Production of NK-92-EGFR-CAR Cells Depend on EGFR Surface Expression on Target Cells Applicants next explored whether the enhanced cytolytic activity and IFN-γ production in EGFR-CAR-transduced NK-92 or NKL cells triggered by GB cells relies on cell surface EGFR antigen expression. Of the GB cells tested, only GMB19 stem cell did not express either EGFR or EGFRvIII on their surface. Thus, Applicants utilized this cell line to investigate whether forced wtEGFR or EGFRvIII overexpression in GB19 cells was sufficient to alter their sensitivity to EGFR-CAR-transduced NK-92 or NKL cells. For this purpose, Applicants overexpressed either wtEGFR or EGFRvIII on GB19 cells by retroviral infection, confirmed by flow cytometric analysis (FIG. 5A). There was a significant increase in the cytotoxic activity of EGFR-CAR-modified NK-92 and -NKL cells towards GB19 cells exogeneously overexpressing EGFR or EGFRvIII when compared to target GB19 cells lacking EGFR expression or mock-transduced NK-92 and NKL effector cells (FIG. 5B). Likewise, EGFR-CAR-transduced NK-92 and NKL cells secreted significantly higher levels of IFN-γ when co-cultured with EGFR- or EGFRvIII-overexpressing GB19 cells when compared to target GB19 cells lacking overexpression of EGFR or mock-transduced NK-92 and NKL effector cells (FIG. 5C). These results suggest that the increased recognition and elimination of wtEGFR- or EGFRvIII-expressing GB cells by NK-92-EGFR-CAR cells occur in an EGFR-dependent manner. Also, these results were consistent with confirmative experiments showing that forced EGFR expression in 293T cells resulted in increased cytotoxicity and IFN-γ production of NK-92-EGFR-CAR cells compared to NK-92 cells transduced with the empty vector (FIGS. 9A-9C). Moreover, Applicants pre-treated GB30 and U251 cells with EGFR neutralizing antibody (the same clone as the scFv origin), followed by co-culture of the pre-treated tumor cells with mock cells or NK-92-EGFR-CAR cells. Chromium-51 release assay showed that the EGFR blocking antibody blunted the enhancements of both cytotoxicity and IFN-γ production in NK-92-EGFR-CAR when compared to an isotype-matched control antibody (FIG. 10), further confirming that the effects that Applicants identified for NK-92-EGFR-CAR cells are EGFR-dependent.

Figure 6:
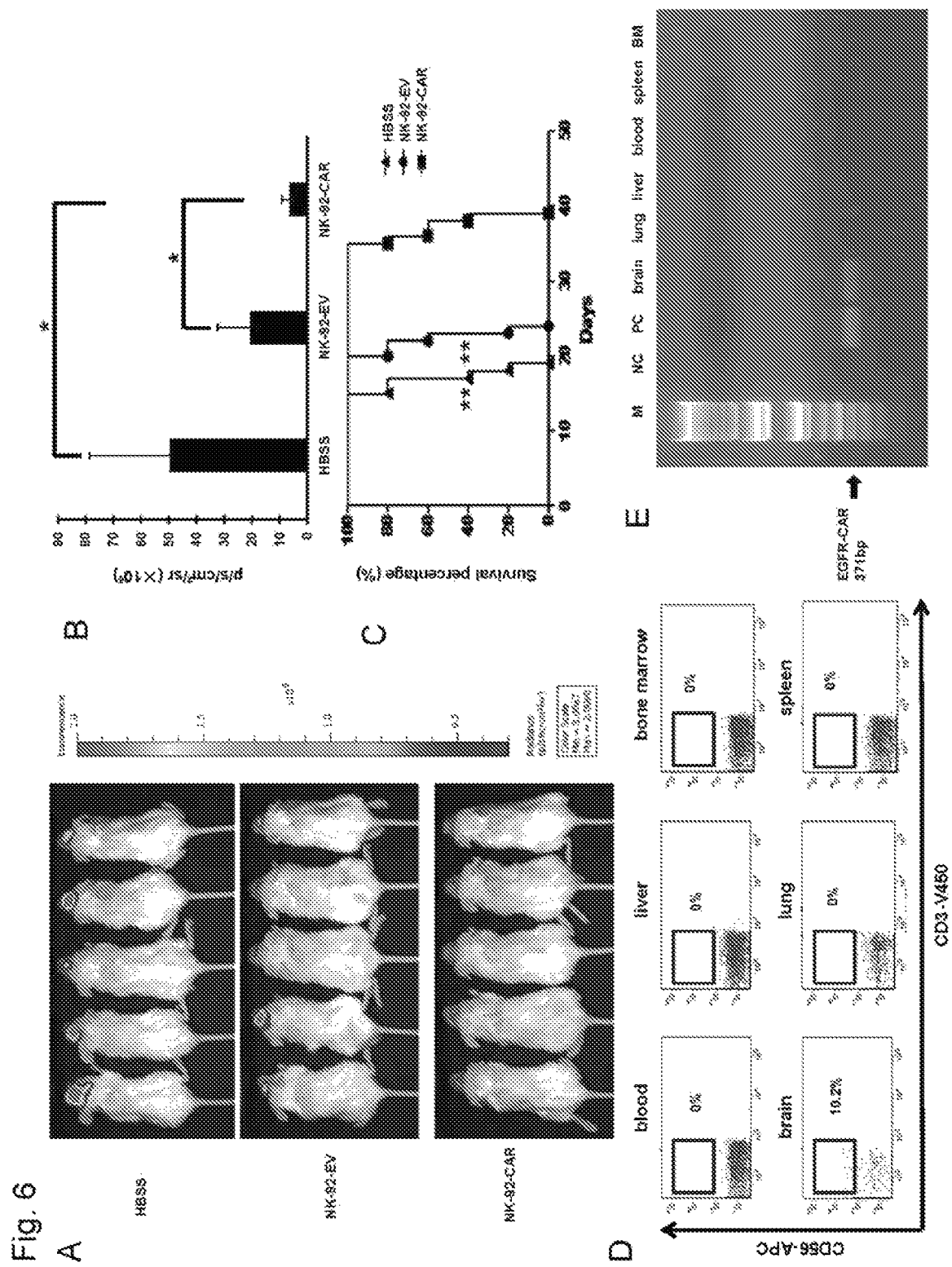
FIGS. 6A-6E show that NK-92-EGFR-CAR cells suppress in vivo growth of orthotopic human glioma stem cells, prolong the survival of glioma-bearing mice, and localize in the brain without migrating to other organ and tissues.
Figure 7:
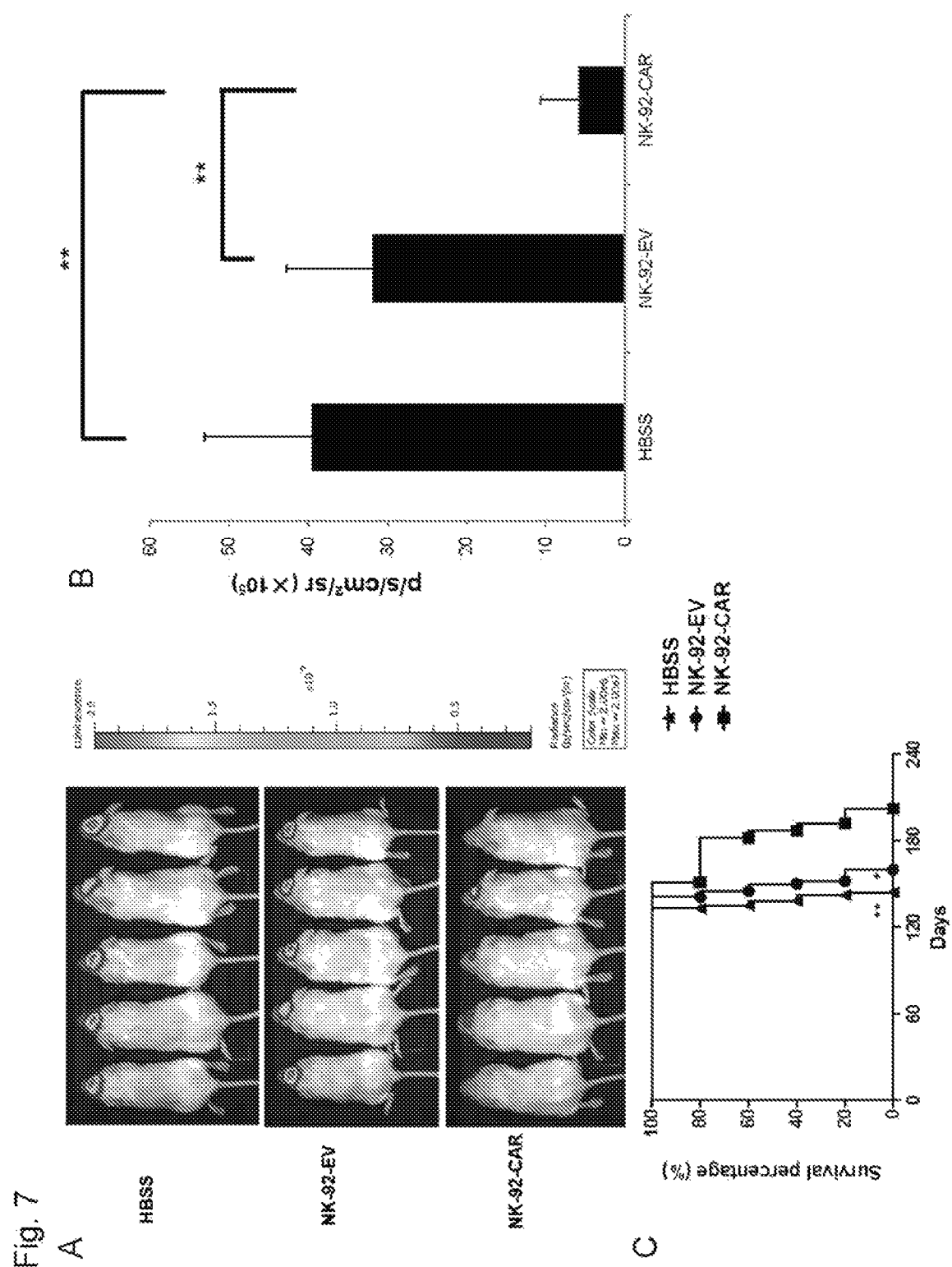
FIGS. 7A-7C show that EGFR-CAR-transduced NK-92 cells inhibit wtEGFR-expressing GB tumor growth and prolong survival of tumor-bearing mice in an orthotopic xenograft GB model.

NK-92-EGFR-CAR Cells Inhibit GB Tumor Growth and Prolong Survival of Tumor-Bearing Mice in Two Orthotopic Xenograft GB Models To further address the potential therapeutic application of NK-92-EGFR-CAR cells, Applicants examined their anti-tumor activity in vivo. Applicants established orthotopic glioma by intracranially implanting EGFRvIII-expressing GB30 glioma stem cells which had been genetically manipulated to express firefly luciferase (GB30-FFL) into the brains of NSG mice. The expression of firefly luciferase enabled us to monitor the tumor growth via in vivo bioluminescence imaging. To minimize potential systemic toxicity, Applicants injected the NK-92-EGFR-CAR intratumorally 7 days post tumor cell implantation. As shown in FIGS. 6A-6B, mice that received either EGFR-CAR- or mock-transduced NK-92 cells had significantly reduced tumor growth as determined by bioluminescence imaging, compared to those injected with HBSS. Importantly, however, the reduction in tumor growth was significantly greater in mice treated with NK-92-EGFR-CAR cells than those treated with mock-transduced NK-92 cells. In agreement with these data, mice treated with NK-92-EGFR-CAR cells survived significantly longer than mice treated with mock-transduced NK-92 cells or HBSS (median survival of 38 vs 23 days between NK-92-EGFR-CAR- and NK-92-EV-treated mice, $p<0.01$; median survival of 38 vs 17 days between NK-92-EGFR-CAR- and HBSS-treated mice, $p<0.01$) (FIG. 6C). To further address the therapeutic efficacy of NK-92-EGFR-CAR cells against wtEGFR-expressing GB tumor, Applicants established an orthotopic GB model by intracranially implanting wtEGFR-expressing U251-FFL cells into NSG mice. Applicants injected NK-92-EGFR-CAR cells, NK-92-EV cells or HBSS as a vehicle control intratumorally 10 days, 40 days and 70 days after tumor cell implantation. As shown in FIGS. 7A-7B, mice which were injected intratumorally with EGFR-CAR cells had significantly decreased tumor burden, compared to those infused with HBSS or NK-92-EV cells. Moreover, mice treated with NK-92-EGFR-CAR cells survived significantly longer than those receiving NK-92-EV cells or HBSS (median survival of 187 vs 150 days between NK-92-EGFR-CAR- and NK-92-EV cell-treated mice, $p<0.05$; median survival of 187 vs 138 days between NK-92-EGFR-CAR- and HBSS-treated mice, $p<0.01$) (FIG. 7C). Taken together, NK-92-EGFR-CAR cells could efficiently target and eliminate either wtEGFR- or EGFRvIII-expressing GB in vivo.

Assessment of NK-92-EGFR-CAR Cell Migration after Intracranial Injection

Figure 11:
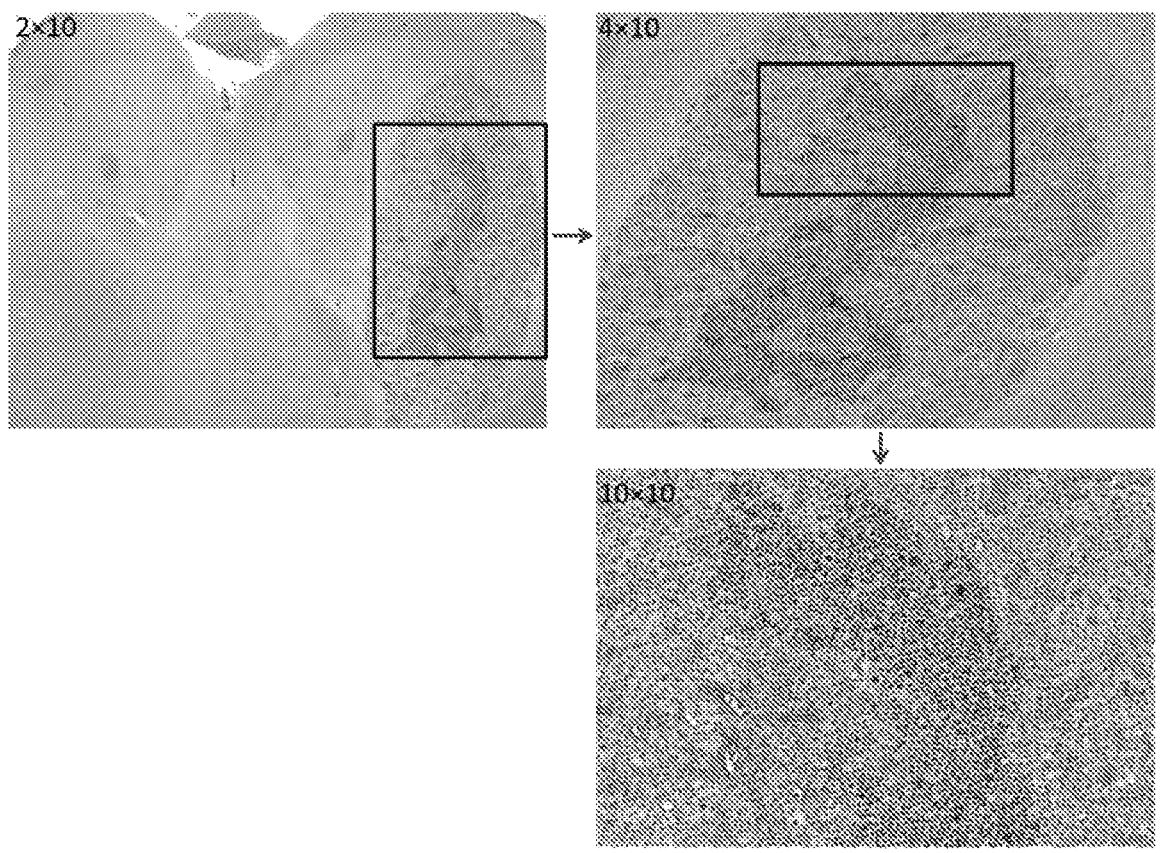
FIG. 11 shows that NK-92-EGFR-CAR cells are located in tumor area after intratumoral injection. NK-92-EGFR-CAR cells were intratumorally injected into mouse brains seven days after GB30 implantation. The mouse brains were harvested 3 days later, embedded by paraffin, and processed for Hematoxylin and Eosin (H&E) staining. H&E staining showed that NK-92-EGFR-CAR cells only existed inside tumor area. Magnifications of 20×, 40× and 100× were shown (Objective: 2×, 4× or 10×; Eyepiece: 10×).

To evaluate the safety of intracranial injection of NK-92-EGFR-CAR cells, Applicants first analyzed the systemic cell distribution after intracranial injection. Applicants undertook a flow cytometric analysis and a more sensitive PCR approach to assess the distribution of NK-92-EGFR-CAR cells in a variety of organs and tissues harvested three days after their intracranial injection into GB30-bearing mice. As shown in FIG. 6D, CD56+ cells could be identified only in the brain and constituted only 10.2% of total immune infiltrating cells in the brain. Similarly, PCR analysis was unable to detect EGFR-CAR expression in any organ site tested other than brain (FIG. 6E). Together, these data suggest that intracranial administration of NK-92-EGFR-CAR cells in an orthotopic mouse model of human GB can be performed without extracranial migration of the effector cells. Applicants next performed Hematoxylin and Eosin (H&E) staining of brain sections of GB30-bearing mice being intratumorally infused with NK-92-EGFR-CAR cells. The results showed that NK-92-EGFR-CAR cells distributed only inside the tumor (FIG. 11).

Discussion

In this study, Applicants developed a novel and promising strategy against GB, utilizing EGFR-CAR-modified human NK-92 cells to intracranially target human GB. Tumors from GB patients express either wtEGFR or both wtEGFR and EGFRvIII (Fan, Q. W. et al. (2013) Cancer Cell 24:438-449), suggesting that targeting both forms of this surface protein will have a broader application or be more effective than targeting only one. Applicants also demonstrated the in vivo efficacy and safety of intracranial injection of EGFR-CAR-modified NK-92 cells in Applicants' orthotopic preclinical model.

CAR T cells have been effectively used for treatment of refractory chronic lymphocytic leukemia and acute lymphoblastic leukemia, and represent a powerful new therapeutic modality for these highly drug-resistant tumors (Porter, D. L. et al. (2011) N Engl J Med. 365:725-733; Grupp, S. A. et al. (2013) N Engl J Med. 368:1509-1518; Brentjens, R. J. et al. (2013) Sci Transl Med. 5:177ra138; Papapetrou, E. P. et al. (2011) Nature Biotechnology 29:73-78). Also, several studies have demonstrated the use of CAR T cells to treat GB (Morgan, R. A. et al. (2012) Hum Gene Ther. 23:1043-1053; Ohno, M. et al. (2010) Cancer Sci. 101:2518-2524; Ahmed, N. et al. (2010) Clin Cancer Res. 16:474-485). But these studies only focused on targeting EGFRvIII. Moreover, CAR T cells can cause cytokine-related adverse events and tumor lysis syndrome (Grupp, S. A. et al. (2013) N Engl J Med. 368:1509-1518; Morgan, R. A. et al. (2010) Mol Ther. 18:843-851), which may result in substantial toxicity or death of patients. In addition, production of autologous CAR T cells is an expensive and time-consuming approach. Thus, utility of CAR NK cells to target both wtEGFR and EGFRvIII for GB treatment is a good alternative approach.

CAR-engineered NK cell lines (e.g. NK-92 used in this study) could potentially provide an off-the-shelf, renewable product to broadly treat different GB patients. Applicants' present study is the first to investigate the utilization of CAR-modified NK-92 cells against GB. CAR-modified NK-92 cells have been shown to effectively target other cancers. For example, Esser et al. engineered NK-92 cells to stably express CAR against disialoganglioside GD2, which is expressed at high levels on neuroblastoma (NB) cells (Esser, R. et al. (2012) J Cell Mol Med. 16:569-581). Expression of GD2-CAR on NK-92 cells enhanced specific elimination of GD2-expressing NB cells that were resistant to killing by parental NK-92 cells, demonstrating the potential clinical utility of the GD2-CAR NK cells against NB. Applicants have recently developed CS1-CAR-expressing NK-92 cells to target multiple myeloma (MM) cells and demonstrated that these engineered NK-92 cells were able to display enhanced cytolysis and IFN-γ production when co-cultured with MM cells in vitro (Chu, J. et al. (2014) Leukemia 28:917-927). Importantly, in an aggressive orthotopic MM xenograft mouse model, adoptive transfer of CS1-CAR-modified NK-92 cells efficiently impeded the dissemination of human IM9 MM cells in vivo and also significantly prolonged the overall survival of IM9-bearing mice (Chu, J. et al. (2014) Leukemia 28:917-927).

To Applicants' knowledge, this is the first study investigating the potential of CAR immune cells to target both wtEGFR and EGFRvIII for GB treatment. Applicants generated EGFR-CAR-engineered NK-92 and NKL cells as well as primary NK cells which in vitro efficiently lyse GB cells expressing either wtEGFR or EGFRvIII. Both molecules play contributory roles in gliomagenesis. EGFRvIII-expressing cells typically co-exist with wtEGFR-expressing cells in same patients. Biernat reported that 40% (8 out of 20) of EGFR GB biopsies also showed positive for EGFRvIII, but only 15% (3 out of 20) with a predominant EGFRvIII amplification, suggesting that the limited effectiveness could only be achieved for therapeutic approaches based on selective targeting of EGFRvIII (Biernat, W. et al. (2004) Brain Pathol. 14:131-136). In another study, among 58 GB tumors, 83% (48/58) stained for wtEGFR by IHC. Furthermore, 19% (11/58) of these samples were double positive for wtEGFR and EGFRvIII (Fan, Q. W. et al. (2013) Cancer Cell 24:438-449). These two studies demonstrate that a substantial portion of GB patients have wtEGFR-expressing and EGFRvIII-expressing cells. Thus, compared with therapeutic approaches to treat GB selectively targeting either wtEGFR or EGFRvIII, the EGFR-CAR NK therapy described here targets both wtEGFR and EGFRvIII. As noted above, EGFRvIII-specific CAR T cells show good anti-tumor activity against GB expressing EGFRvIII both in vitro and in vivo (Morgan, R. A. et al. (2012) Hum Gene Ther. 23:1043-1053; Ohno, M. et al. (2010) Cancer Sci. 101:2518-2524; Sampson, J. H. et al. (2014) Clin Cancer Res. 20:972-984). Applicants believe that an approach targeting both wtEGFR and EGFRvIII should be effective to treat not only GB patients with wtEGFR-expressing tumor cells alone, but also GB patients with both wtEGFR-expressing tumor cells and EGFRvIII-expressing tumor cells. For this purpose, Applicants engineered NK-92 cells to express an EGFR-CAR targeting both wtEGFR and EGFRvIII, and demonstrated that GB cells expressing wtEGFR or EGFRvIII could be efficiently eliminated in vitro and/or in vivo.

A potential challenge of targeting wtEGFR as well as EGFRvIII on glioma cells is the presence of wtEGFR on normal tissues. Systemic infusion of EGFRvIII-specific CAR T cells is believed to be relatively safe, as EGFRvIII is not expressed on normal epithelial cells that can express high levels of wtEGFR. However, systemic administration of NK-92-EGFR-CAR or primary NK cells could result in serious systemic toxicity due to their impact on normal wtEGFR-expressing cells. To minimize this risk, Applicants injected NK-92-EGFR-CAR cells intracranially to restrict their mobility, and demonstrated that these CAR cells remained undetectable in tissues other than brain. In further support of this strategy, a recent study shows that intracranial delivery of toxin-conjugated scFv from an EGFR antibody targeting both wtEGFR and EGFRvIII results in strong anti-neoplastic effects against intracranial glioblastoma xenografts expressing wtEGFR or co-expressing wtEGFR and EGFRvIII. This local administration did not cause obvious systemic toxicity (Chandramohan, V. et al. (2013) Clin Cancer Res. 19:4717-4727). In addition, Applicants' H&E staining also showed that NK-92-EGFR-CAR cells injected into implanted tumors in the brain reside in the tumor area. However, as NK-92 is a lymphoma cell line, for future clinical applications, NK-92 cells armed with CAR should be irradiated prior to infusion into patients. Several preclinical studies demonstrated that NK-92-CAR cells received 10 Gy irradiation showed similar effects in vitro and in vivo when compared with non-irradiated cells (Uherek, C. et al. (2002) Blood 100:1265-1273; Schonfeld, K. et al. (2015) Mol Ther. 23:330-338). Alternatively, EGFR-CAR primary NK cells should be considered, as Applicants showed they are also potent to eradicate GB cells. Importantly, genetically-engineered artificial antigen-presenting cells (aAPCs) expressing membrane-bound IL-15 (mbIL15) or membrane-bound IL-21 (mbIL21) have recently been used to successfully expand primary NK cells (Jordan, C. T. (2009) Cell Stem Cell 4:203-205; Brennan, C. et al. (2009) PLoS One 4:e7752).

Importantly, in Applicants' study Applicants observed high expression of endogenous EGFRvIII on the majority of patient-derived GB stem cells tested, making them more susceptible to lysis by NK-92-EGFR-CAR cells than by NK-92 cells transduced with control vector. GB stem cells are a subpopulation of tumor cells that reflect biological and pathological characteristics of primary GB, and retain the capability to undergo self-renewal, multi-lineage differentiation, and regeneration of the entire tumor population (Jordan, C. T. (2009) Cell Stem Cell 4:203-205). GB stem cells are considered to be responsible for tumor initiation, propagation, recurrence, and chemo- and radio-resistance. Targeting GB stem cells is believed to be a key aspect in the prevention of GB relapse. In fact, Applicants' in vivo data show that one time administration of NK-92-EGFR-CAR cells significantly prolongs the survival of mice implanted with patient-derived GB stem cells expressing EGFRvIII. Thus, Applicants believe Applicants' study demonstrating the use of NK-92-EGFR-CAR cells to target GB cells and GB stem cells both in vitro and in two xenograft mouse models is highly relevant to the potential treatment of relapsed human GB in the clinic.

GB is composed of distinct molecular subtypes. Mesenchymal (MES) and proneural (PN) GBs have been identified as the most important subtypes of GB (Mao, P. et al. (2013) Proc Natl Acad Sci. USA 110:8644-8649; Brennan, C. et al. (2009) PLoS One 4:e7752; Phillips, H. S. et al. (2006) Cancer Cell 9:157-173; Verhaak, R. G. et al. (2010) Cancer Cell 17:98-110). In Applicants' experiments, all MES and two of three PN GB stem cells (GSCs) that Applicants tested were positive for EGFR expression by flow cytometry. PCR analysis further demonstrated that all of these GB stem cells express EGFRvIII, while GB non-stem cell lines usually express only wtEGFR (except for ectopic over-expression of EGFRvIII in Gli36dEGFR). Consistent with these findings, Applicants' in vitro data demonstrate that EGFR-CAR NK cells display enhanced IFN-γ secretion and cytotoxicity when cultured with either PN or MES EGFR GSCs in vitro. MES GSCs are more aggressive in vitro and are capable of quickly giving rise to intracranial xenografts in vivo (Mao, P. et al. (2013) Proc Natl Acad Sci. USA 110:8644-8649). MES GSCs also exhibit remarkable resistance to radiation compared with PN GSCs (Mao, P. et al. (2013) Proc Natl Acad Sci. USA 110:8644-8649). Applicants' in vivo data demonstrated that the NK-92-EGFR-CAR cells showed efficacy in the aggressive GB30 MES GSC xenograft model.

In conclusion, Applicants have successfully generated CAR NK cells that target both wtEGFR and EGFRvIII in GB. NK cells armed with this EGFR-CAR efficiently and specifically recognize and eradicate GB cells and/or their stem cells in vitro and/or in vivo. Applicants' study supports the clinical application of EGFR-CAR-modified NK-92 cells for the treatment of relapsed GB, which may be locally administered alone or in combination with other approaches.

Experiment 2—Combination of EGFR CAR Expressing Cells and oHSV

Cell Culture

Human breast cancer cell lines MDA-MB-231, MDA-MB-468, and MCF-7, as well as 293T and Phoenix cells, were cultured in DMEM (Invitrogen, Grand Island, N.Y.) and supplemented with 10% FBS, penicillin (100 U/ml), and streptomycin (100 µg/ml) (all from Invitrogen). Human NK cell line NK-92 and primary NK cells (obtained from the American Red Cross in Columbus) were maintained in RPMI-1640 (Invitrogen) supplemented with 20% FBS, penicillin (100 U/ml), streptomycin (100 µg/ml), and 200 IU/mL recombinant human (rh) IL-2 (Gold Biotechnology, MO).

Mice

Six to eight-week-old NOD.Cg-Prkdc$^{scid}$ Il2rg$^{tm1Wjl}$/SzJ (NSG) mice were obtained from Jackson Laboratories (Bar Harbor, Me.). All animal work was approved by The Ohio State University Animal Care and Use Committee. Mice were monitored daily for disease progression and sacrificed when they became moribund with neurologic impairments or showed obvious weight loss.

Generation of EGFR-CAR Lentiviral Construct

The anti-EGFR single chain variable fragment (scFv) was derived from DNA sequences encoding a specific monoclonal antibody against both wtEGFR and EGFRvIII. See Soffietti et al. (2002) J. Neurol. 249(10):1357-1369. The VH-linker-VL fragment was incorporated in frame with the CD28-CD3ζ portion incised from a retroviral vector. The entire anti-EGFR-scFv-CD28-CD3ζ fragment was then ligated into a lentiviral vector designated as pCDH-CMV-MCS-EF1-copGFP (System Biosciences, Mountain View, Calif.) to generate the pCDH-EGFR-scFv-CD28-CD37ζ (pCDH-EGFR-CAR) construct.

Lentiviral Production and Transduction of NK-92 Cells:

To produce lentivirus for infection of NK-92 cells, 293T cells were co-transfected with the aforementioned pCDH-EGFR-scFv-CD28-CD3ζ plasmid or a mock pCDH vector together with packaging constructs pCMV-VSVG and pCMV-DR9 using calcium phosphate transfection reagent (Promega, Madison, Wis.). The transfection and infection procedures were modified from the protocol of Chu et al. (2014) Official Journal of the AACR, 20(15):3989-4000.

Generation of MDA-MB-231 Cells Stably Expressing CBRluc-EGFP:

MDA-MB-231 cells stably expressing CBRluc-EGFP was generated by retroviral transfection with the ΔU3CBRluc-EGFP vector (a generous gift from Dr. J F DiPersio) following the Chu etl al. (2014) protocol. EGFP positive breast cancer cells were then sorted using a FACS Aria II cell sorter (BD Biosciences, San Jose, Calif.) and expanded, yielding MDA-MB-231-CBRluc-EGFP cells.

Flow Cytometry Analysis:

To determine EGFR expression on the surface of breast cancer cell lines, cells were incubated with the mouse monoclonal anti-human EGFR (clone H11, DAKO) antibody, followed by staining with APC-conjugated goat anti-mouse IgG secondary antibody. The surface expression of EGFR-CAR was assessed by flow cytometry as described in Chu et al. (2014).

Hematoxylin and Eosin (HE) Staining and Immunohistochemistry (IHC) Assay:

Paraffin-embedded sections of tumor tissues from patients with both primary breast cancer and brain metastasis were stained with HE or with anti-wild-type-EGFR antibody (1:2000, DAK-H1-WT; Agilent Technologies, Santa Clara, Calif.) for IHC. An automatic immunostainer (BenchMark XT, Ventana Medical Systems, Tucson, Ariz.) was used according to the manufacturer's instructions. Sections were visualized and photographed by a Leica laser confocal microscope (SP5Wetzlar, Germany).

Cytotoxicity Assay

A standard 4-h $^{51}$Cr release assay was performed as described previously (Yu, J. et al. (2010) Blood 115:274-281). The percentage of specific cell lysis was calculated using the standard formula: 100×(cpm experimental release−cpm spontaneous release)/(cpm maximal release−cpm spontaneous release).

IFN-γ Release Assay $1 \times 10^6$ target cells were incubated with equal numbers of effector cells in the wells of 96-well V-bottom plates for 24 h. Cell-free supernatants were assayed for IFN-γ secretion by enzyme-linked immunosorbent assay (ELISA) using a kit from R&D Systems (Minneapolis, Minn.) according to the manufacturer's protocol. Data depicted in figures represent mean values of triplicate wells from one of three representative experiments with similar results.

MTS Assay

Breast cancer cell line cells ($5 \times 10^3$) were seeded in 96-well flat bottom culture plates and incubated at 37° C. in DMEM medium containing 10% FBS. At the end of treatment, cell viability was determined using a rapid, tetrazolium-based MTS (3-(4,5-dimethylthiazol-2-yl)-5-(3-carboxymethoxyphenyl)-2-(4-sulfophenyl)-2H-tetrazolium, inner salt) colorimetric assay (CellTiter 96 cell proliferation assay kit; Promega, Madison, Wis.) according to the manufacturer's instructions. See Hayon et al. (2003) Leuk. Lymphoma 44(11):1957-1962. All experiments were performed at least in triplicates on three separate occasions.

Luciferase Assay

MDA-MB-231-CBRluc-EGFP cells ($5 \times 10^3$) were seeded in 96-well flat bottom culture plates and incubated at 37° C. in DMEM medium containing 10% FBS with different treatments. At different time points, 20 µL of the culture media were collected directly for luciferase assays using the Dual-Glo Luciferase Assay System (Promega), as described in Fu et al. (2010) PLoS One. 5(7):e11867. At day 4, cell pellets were rinsed twice with PBS, and then lysed with 30 µL of 1× passive lysis buffer (Promega). Lysates were pelleted by centrifugation (13,000 rpm, 1 minute) and the supernatant was collected to measure luciferase activity.

Treatment of Breast Cancer Brain Invasion in NSG Mice

NSG mice were anesthetized and fixed in a stereotactic apparatus, and $1 \times 10^5$ MDA-MB-231-CBRluc-EGFP cells in 2 µL Hank's buffered salt solution (HBSS) were injected into mouse brain on day 0, where a burr hole was drilled 2 mm laterally and 1 mm anteriorly to the right bregma to a depth of 3.25 mm. On day 10, the mice were injected intratumorally with $2 \times 10^6$ effector cells, i.e. EGFR-CAR-transduced NK-92 cells (NK-92-EGFR-CAR) or empty vector-transduced NK-92 cells (NK-92-EV) in 5 µL HBSS. The oHSV-1 alone group was injected intratumorally with $2 \times 10^5$ plaque-forming units (pfu) oHSV-1 (rQNestin34.5)—see Kambara et al. (2005) Cancer Res. 65(7):2832-2839—in 5 µL HBSS. Mice treated with 5 µl HBSS were used as a control. On day 15, mice in the CAR plus oHSV-1 treatment group were intratumorally injected with $2 \times 10^5$ pfu oHSV-1.

Mice were monitored daily and euthanized when they showed signs of morbidity. Four weeks after inoculation with MDA-MB-231-CBRluc-EGFP cells, the mice were intraperitoneally (i.p.) infused with D-luciferin (150 mg/kg body weight; Gold Biotechnology, St. Louis, Mo., USA), anesthetized with isoflurane, and imaged using the In Vivo Imaging System (IVIS-100, PerkinElmer, Waltham Mass., USA) with living image software (PerkinElmer).

Statistics

The unpaired Student's t test was used to compare two independent groups for continuous endpoints if normally distributed with or without data transformation. One-way ANOVA was used to compare among three or more groups. For survival data, Kaplan-Meier analysis was used to estimate survival functions and log-rank test was used to compare the survival between two groups. All tests were two-sided. P values were adjusted for multiple comparisons using Holm's procedure. A P value of less than 0.05 was considered statistically significant.

Results

Figure 12:
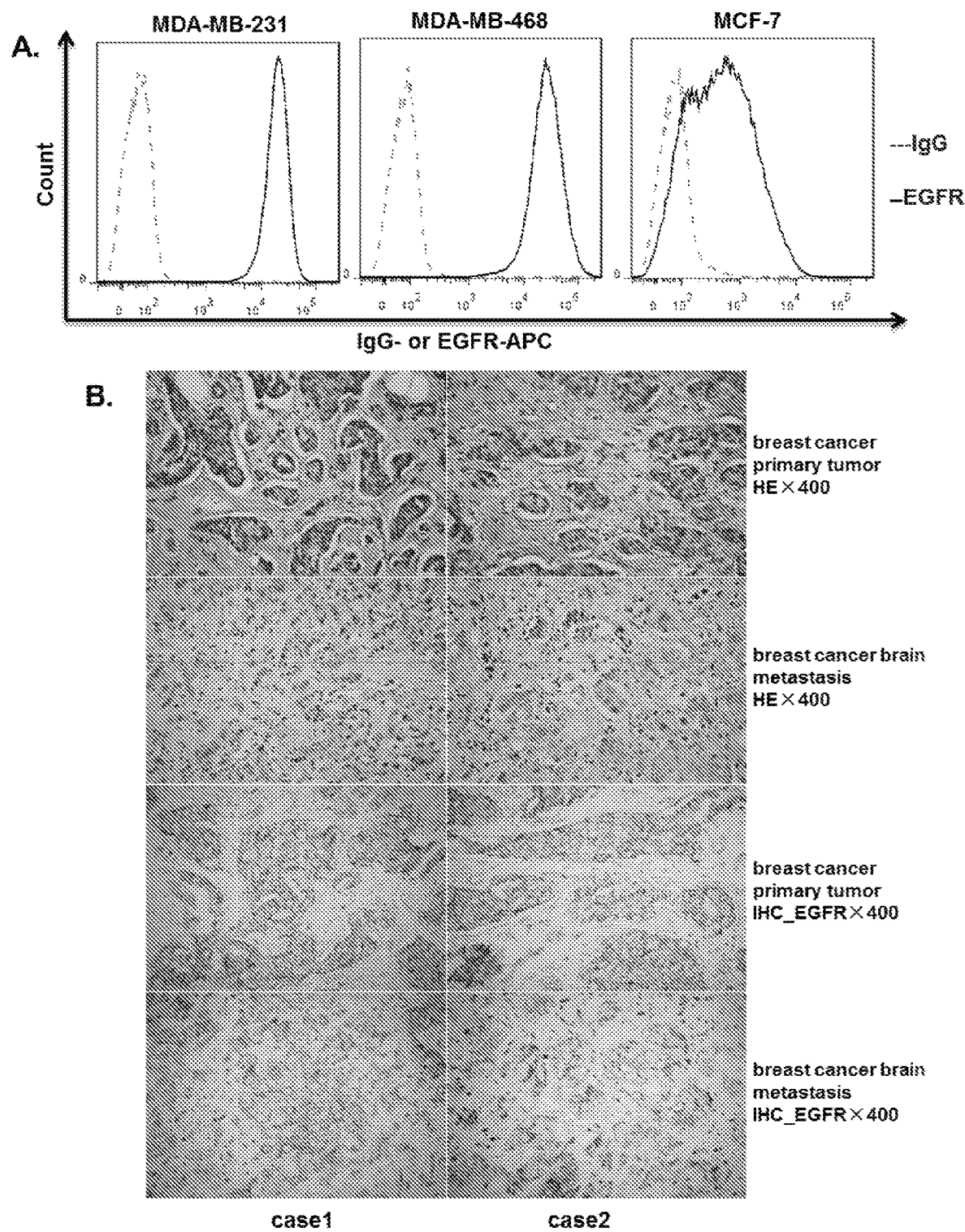
FIGS. 12A-12B depict expression of EGFR in breast cancer cell lines and tissues. Expression of EGFR on the cell surface of breast cancer cell lines (MDA-MB-231, MDA-MB-468, and MCF-7) was detected by flow cytometry (FIG. 12A). Hematoxylin and eosin (HE) staining and immunohistochemistry (IHC) of EGFR expression was performed for tumor tissues from patients with primary breast cancer and brain metastases (FIG. 12B).

Expression of EGFR in Breast Cancer Cell Lines and Primary and Metastatic Tissues To assess the surface expression of EGFR in breast cancer cell lines, cells were stained with an EGFR-specific antibody, followed by flow cytometric analysis. As shown in FIG. 12A, EGFR was expressed on the surface of MDA-MB-231, MDA-MB-468, and MCF-7 cell lines, although levels were clearly lower on MCF-7 cells. EGFR expression was then evaluated by immunohistochemistry (IHC) in primary tumor tissues and the corresponding brain metastasis lesions from two cases of patients diagnosed with metastatic breast cancer, after confirming the existence of tumor cells by hematoxylin and eosin (HE) staining (FIG. 12B, top two rows). Surface EGFR expression was observed not only on tumor cells from the primary lesions, but also on those from the brain metastases (FIG. 12B, bottom two rows).

Figure 13:
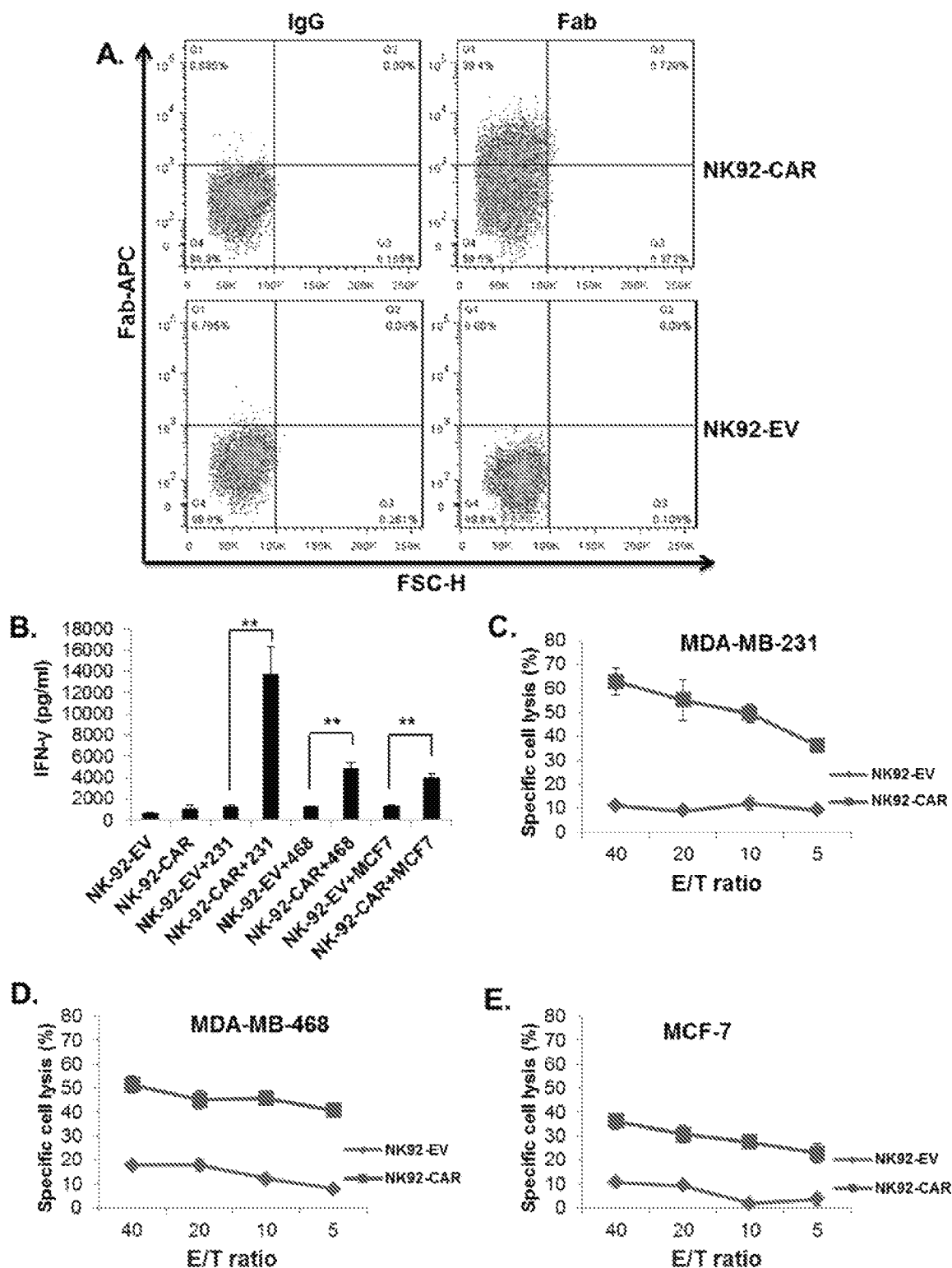
FIGS. 13A-13E demonstrate that EGFR-CAR NK-92 cells recognize and lyse EGFR positive cells of breast cancer cell lines. Expression of EGFR scFv on EGFR-CAR-transduced NK-92 cells, was determined by flow cytometry using a goat anti-mouse F(ab')$_2$ polyclonal antibody (FIG. 13A) IFN-γ release by empty vector (EV)-transduced or EGFR-CAR-transduced NK-92 cells in the absence or presence of MDA-MB-231, MDA-MB-468 or MCF-7 cells was determined using a standard ELISA assay. **P<0.01 (FIG. 13B). Cytotoxic activity of empty vector (EV)-transduced or EGFR-CAR-transduced NK-92 cells against MDA-MB-231 (FIG. 13C), MDA-MB-468 (FIG. 13D), or MCF-7 (FIG. 13E) cells was performed using a standard chromium-51 release assay. (E, effect cell; T, target cell)
Figure 14:
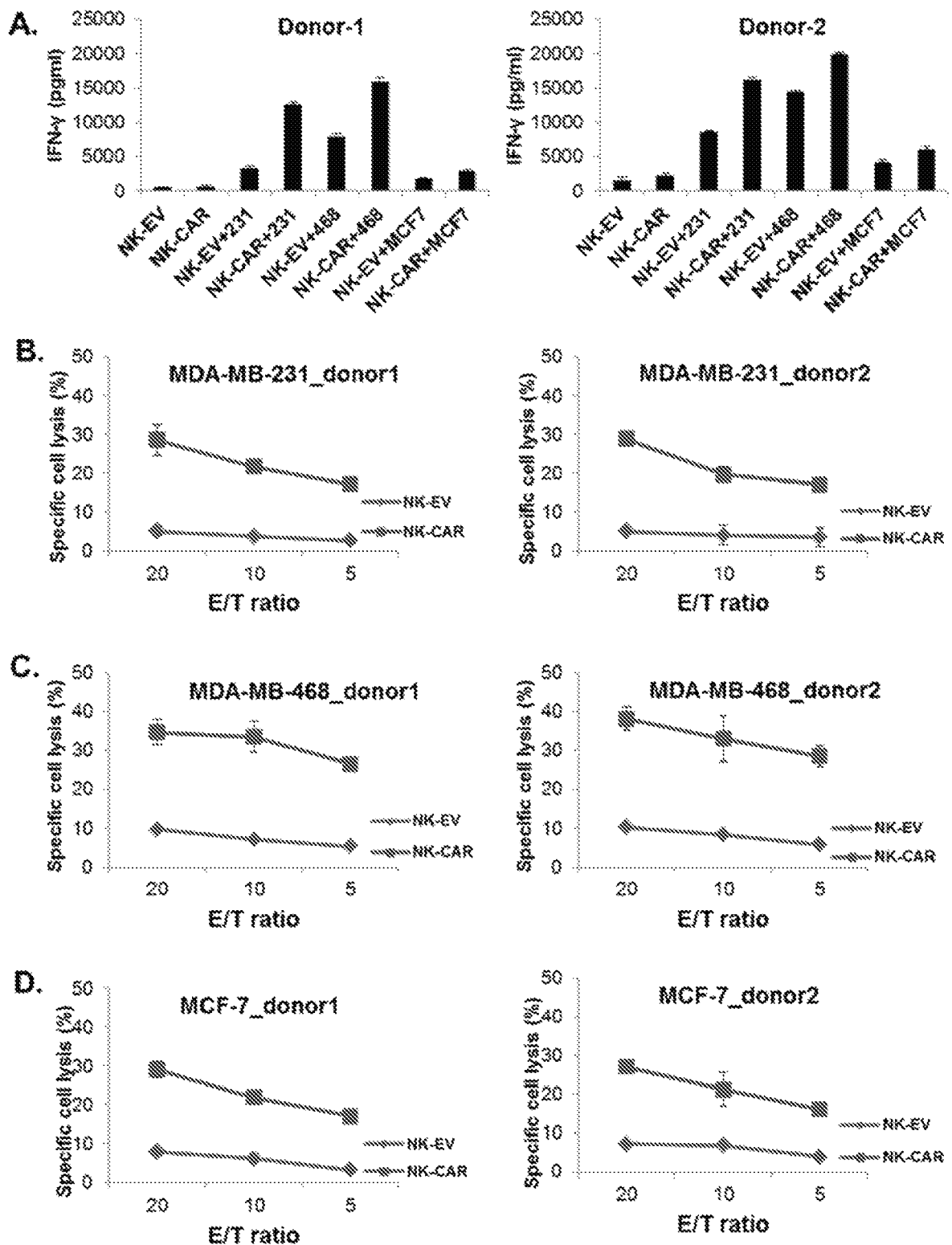
FIGS. 14A-14D depict enhanced cytotoxicity and IFN-γ production of EGFR-CAR primary NK cells when stimulated with $EGFR^+$ breast cancer cells. IFN-γ release by empty vector (EV)-transduced or EGFR-CAR-transduced primary NK cells in the absence or presence of MDA-MB-231, MDA-MB-468 or MCF-7 cells was determined using a standard ELISA assay (FIG. 14A). Cytotoxic activity of empty vector (EV)-transduced or EGFR-CAR-transduced primary NK cells against MDA-MB-231 (FIG. 14B), MDA-MB-468 (FIG. 14C), or MCF-7 (FIG. 14D) cells was performed using a standard chromium-51 release assay. (E, effect cell; T, target cell)
Figure 18:
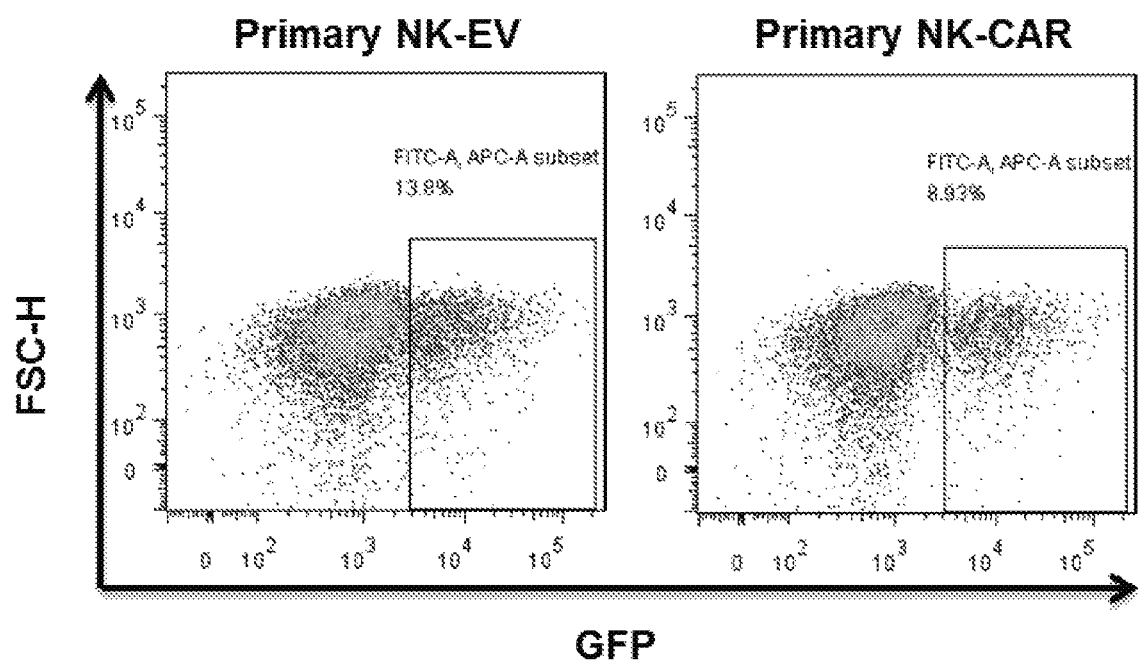
FIG. 18 shows the transduction efficiency of lentiviruses in human primary NK cells. The percentage of GFP (+) cells was determined by flow cytometry after human primary NK cells were infected with EGFR-CAR lentiviruses.
Figure 19:
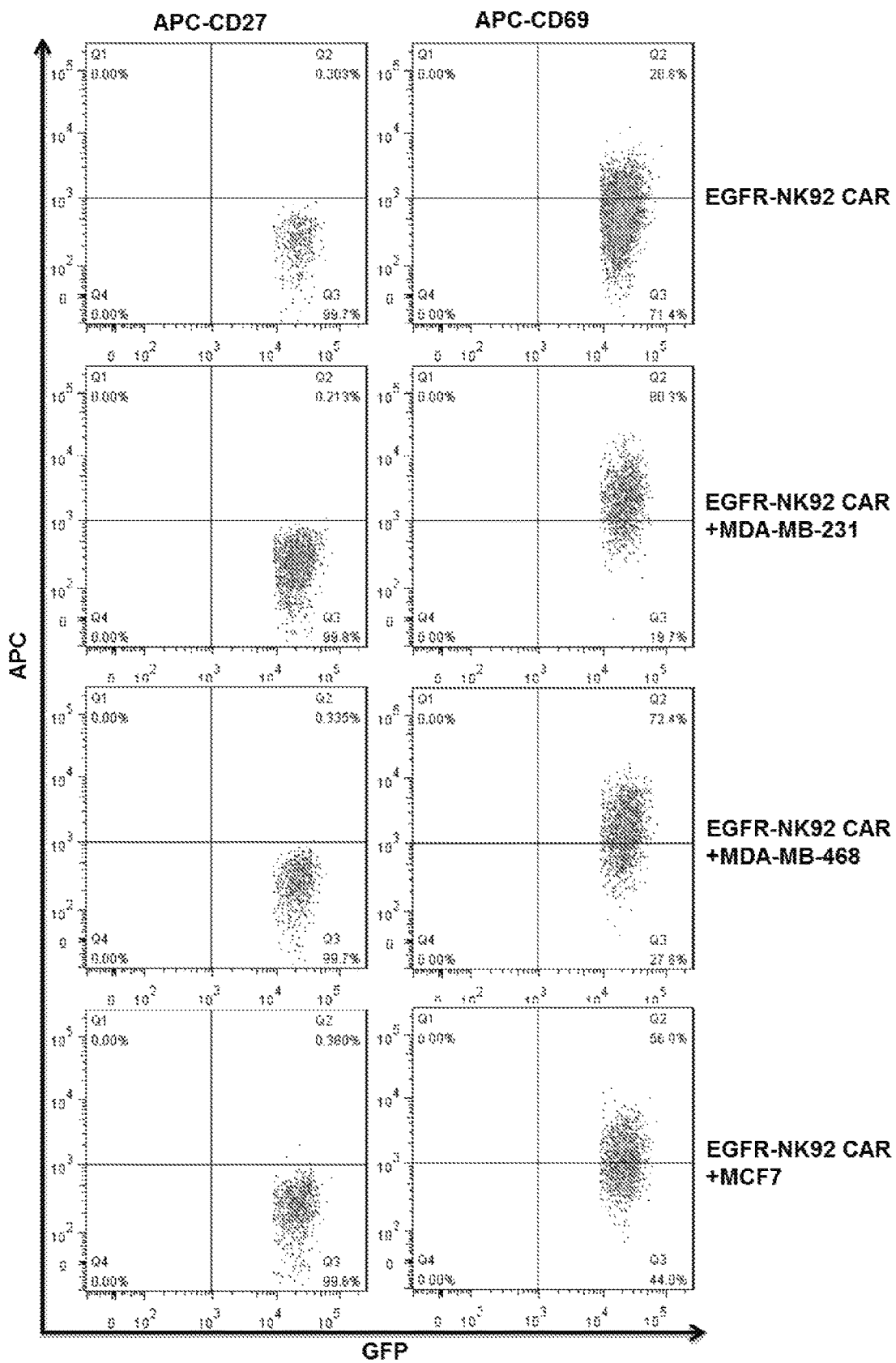
FIG. 19 shows the change in expression of activation markers on the surface of EGFR-CAR NK-92 cells in response to breast cancer cells. Surface expression of CD27 and CD69 in EGFR-CAR NK-92 cells was determined after co-culture with breast cancer cells (MDA-MB-231, MDA-MB-468 and MCF-7) overnight by flow cytometry.

Enhanced Cytotoxicity and IFN-γ Production of EGFR-CAR NK-92 and Primary NK Cells Applicants generated a second-generation EGFR-CAR construct in the pCDH lentiviral backbone. This construct sequentially contains a signal peptide, EGFR scFv, a hinge region, CD28, and CD3ζ. NK-92 and primary NK cells from healthy donors were transduced with the CAR-expressing lentiviruses and sorted based on expression of GFP by the vector. Applicants performed flow cytometric analysis using a goat anti-mouse F(ab')$_2$ antibody that recognized the scFv portion of anti-EGFR. FIG. 13A shows the expression of EGFR-CAR on the surface of EGFR-CAR-transduced NK-92 cells, which was undetectable on NK-92-EV cells (NK-92 cells transduced with the empty vector pCDH). Next, Applicants explored whether EGFR-CAR expression could confer NK-92 and primary NK cells with enhanced IFN-γ production and cytolytic activity. Applicants observed that EGFR-CAR-transduced NK-92 and primary NK cells (FIG. 18) secreted significantly higher levels of IFN-γ when co-cultured with MDA-MB-231 cells or MDA-MB-468 cells as compared to their corresponding effector cells transduced with an empty vector (FIGS. 13B, 14A). Interestingly, this change in IFN-γ secretion was less discernible when MCF-7 cells with a lower level of EGFR expression were used as targets. Moreover, upon co-culture with these three cell lines, Applicants observed a significant increase in the cytotoxic activity of EGFR-CAR-transduced NK-92 and primary donor derived NK cells compared to that of mock-transduced NK-92 effector cells (FIGS. 13C-13E) or primary NK cells, respectively (FIGS. 14B-14D). Using CD69 surface expression to measure effector cell activation, Applicants also observed that tumor cells with EGFR expression can activate EGFR-CAR-transduced NK-92 cells, with higher activation when MDA-MB-231 and MDA-MB-468 cells were used than when MCF-7 cells were used. Applicants also detected expression of CD27, another NK cell activation marker, and observed that CD27 was not expressed on the surface of EGFR-CAR NK-92 cells (FIG. 19).

Lysis of Breast Cancer Cell Lines by oHSV-1

Figure 15:
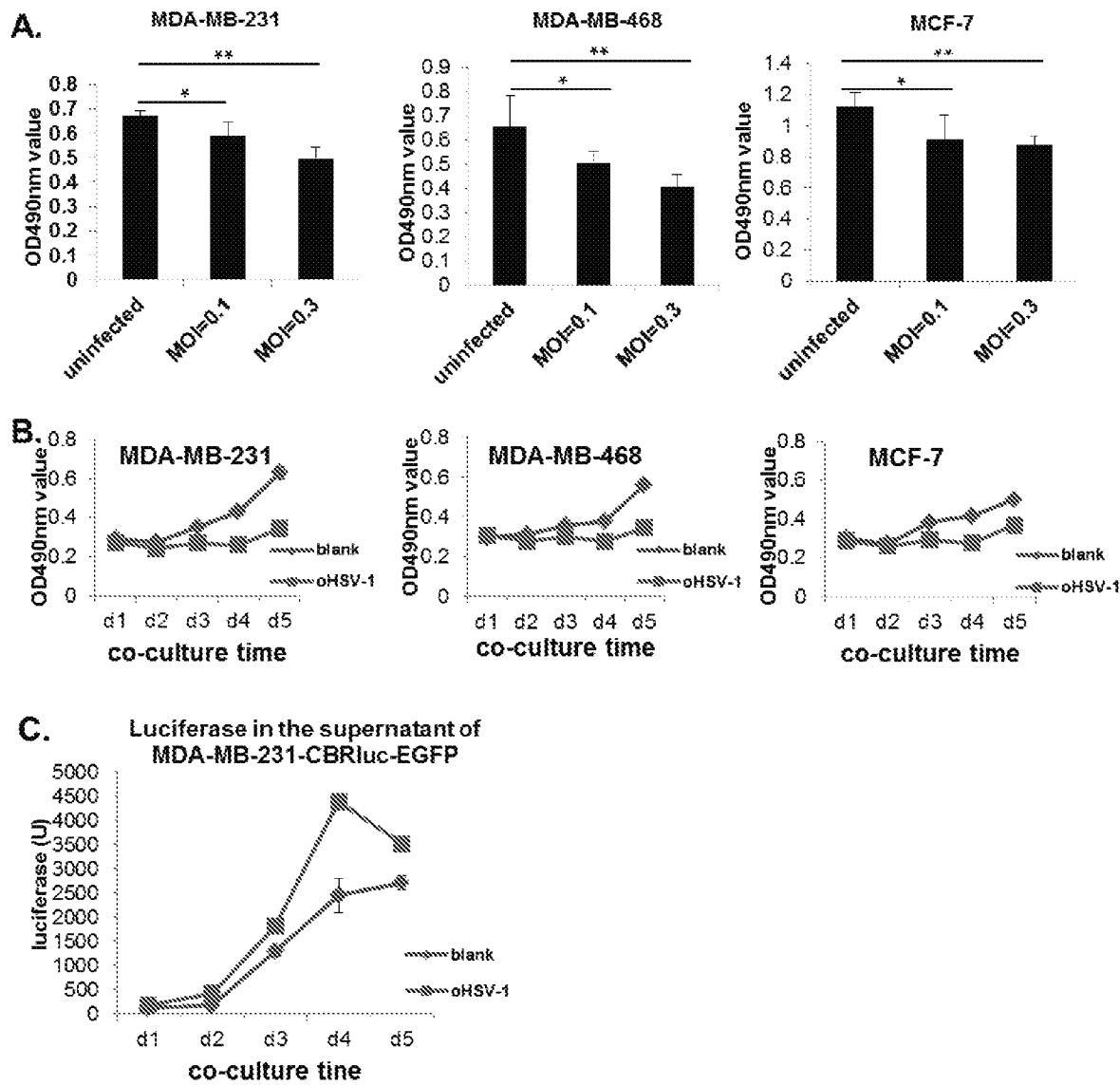
FIGS. 15A-15C show that oHSV-1 alone can lyse and eradicate breast cancer cell line tumor cells. Dose-dependent cytotoxicity of oHSV-1 to breast cancer cell lines (MDA-MB-231, MDA-MB-468 or MCF-7) after co-culture for 48 h was detected by MTS. *P<0.05; **P<0.01 (FIG. 15A).
Figure 20:
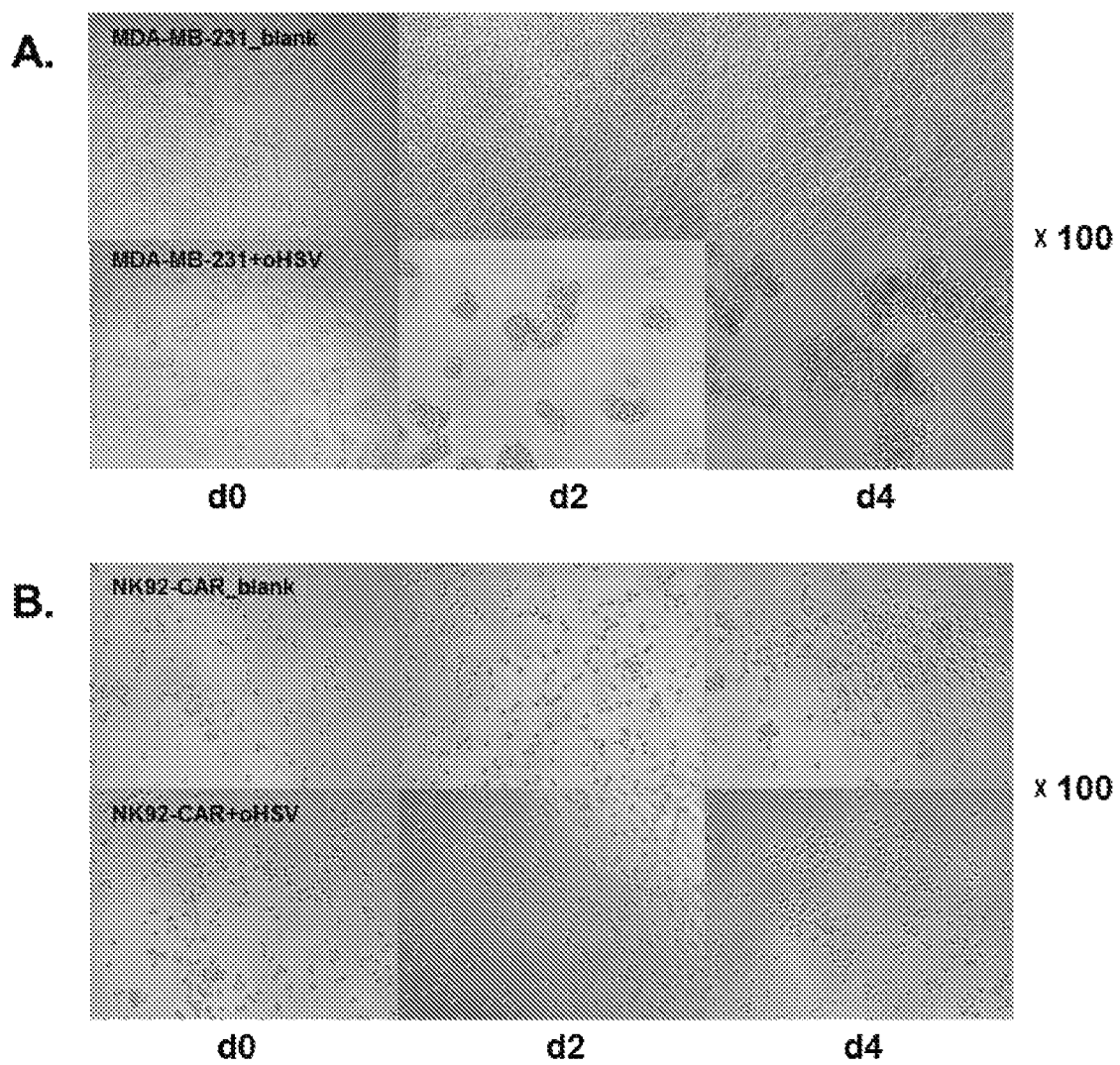
FIGS. 20A-20B demonstrate lysis of breast cancer cells by oHSV alone. Lysis of breast cancer cell line (MDA-MB-231) by oHSV after co-culture for 4 days, demonstrated by the bright images under microscope (FIG. 20A). EGFR-CAR NK92 cells were treated with oHSV-1 for 4 days, and microscopic examination showed that oHSV-1 had no obvious effect on the proliferation and viability of EGFR-CAR NK-92 cells (FIG. 20B).

Applicants explored whether oHSV-1 alone could lyse and destroy breast cancer cells, which have the capability of trafficking into the brain to form metastatic brain tumors. As shown in FIG. 15A, oHSV-1 reduced the viability of MDA-MB-231, MDA-MB-468, and MCF-7 cells in a dose-dependent fashion after co-culture for 48 h, and this effect was observed at different time points (FIG. 15B). Microscopic analysis showed that oHSV-1 alone could lyse these breast cancer cell line cells after co-culture for 4 days (FIG. 20A). This was confirmed using luciferase-expressing MDA-MB-231 cells (MDA-MB-231-CBRluc-EGFP), in which a higher level of luciferase was detected in the supernatants from the group with oHSV-1 infection compared to the mock-infected group (P<0.01 at day 4) (FIG. 15C). Meanwhile, oHSV-1 did not lyse or induce apoptosis of EGFR-CAR NK-92 effector cells, as determined by a microscopic examination (FIG. 20B).

Figure 21:
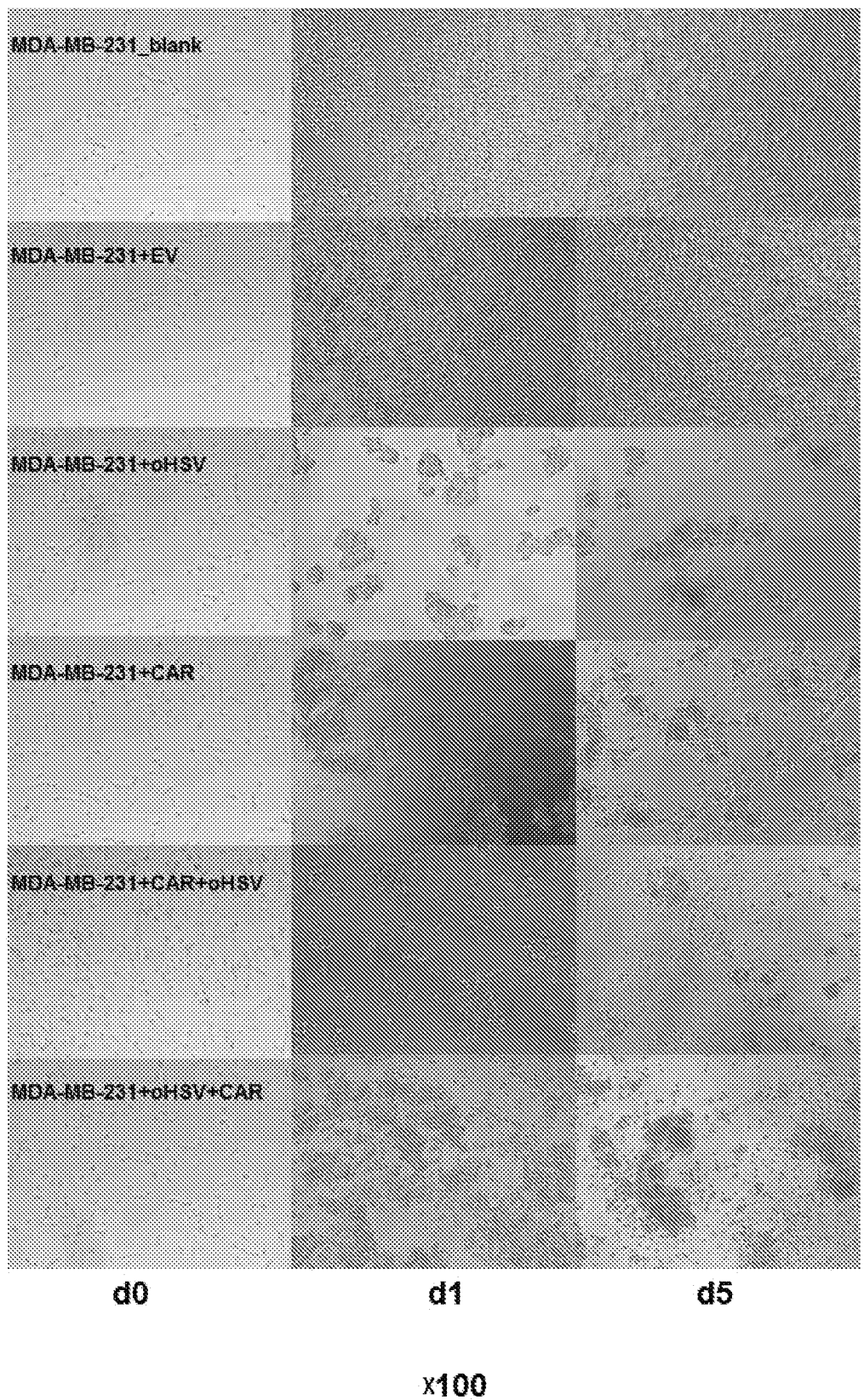
FIG. 21 depicts lysis of breast cancer cell line (MDA-MB-231) by oHSV, EGFR-CAR NK-92 cells, and their combination. "MDA-MB-231+CAR+oHSV" denotes treatment of EGFR-CAR NK-92 cells for 4 h, followed by oHSV-1 treatment. "MDA-MB-231+oHSV+CAR" denotes treatment of oHSV-1 for 4 h, followed by treatment of EGFR-CAR NK-92 cells.

EGFR-CAR NK-92 Cells in Combination with oHSV-1 Result in More Efficient Eradication of Cancer Cells In Vitro When MDA-MB-231 cells were treated with EGFR-CAR NK-92 cells alone or in combination with oHSV-1 (either treatment with EGFR-CAR NK-92 cells for 4 h followed by oHSV-1 treatment or vice versa), MTS assays indicated that the MDA-MB-231 cell line was efficiently killed under all circumstances; however, the combination of EGFR-CAR NK-92 cells with oHSV-1 resulted in more efficient killing (data not shown). Applicants then assessed killing by measuring luciferase activity in the supernatants of MDA-MB-231-CBRluc-EGFP cells following different treatments. Luciferase was found to be degraded quickly (not shown), and thus, the luciferase assay allowed us to determine dynamic, real-time killing rather than accumulative killing. Based on this, Applicants observed that EGFR-CAR NK-92 cells alone and EGFR-CAR NK-92 cells combined with oHSV-1 caused more rapid lysis than oHSV-1 alone (FIG. 5A). When measuring luciferase activity in the remaining MDA-MB-231-CBRluc-EGFP cells (cell pellets) after a co-culture for 4 days, Applicants found that EGFR-CAR NK-92 cells alone, oHSV-1 alone, or EGFR-CAR NK-92 cells combined with oHSV-1 all led to substantial killing of MDA-MB-231-CBRluc-EGFP cells, and EGFR-CAR NK-92 cells combined with oHSV-1 regardless of the order was more effective than the monotherapies (FIG. 16B). Similar results were observed by microscopic examination (FIG. 21). EGFR-CAR NK-92 cells quickly destroyed some of the MDA-MB-231 cells, but a subset of these cells still maintained their original cell shape and integrity even after 5 days. oHSV-1 first caused the target cancer cells to aggregate, then the cells were gradually lysed (FIG. 21). However, the combination of EGFR-CAR NK-92 cells and oHSV-1 resulted in more robust cell killing, especially in the CAR NK-92 cells followed by oHSV-1 treatment group (row 5, FIG. 21). Of note, consistent with $^{51}$Cr release assays (FIG. 13C) and luciferase data (FIG. 16B), microscopic analysis demonstrated that MDA-MB-231 cells were resistant to killing by NK-92-EV cells.

Figure 17:
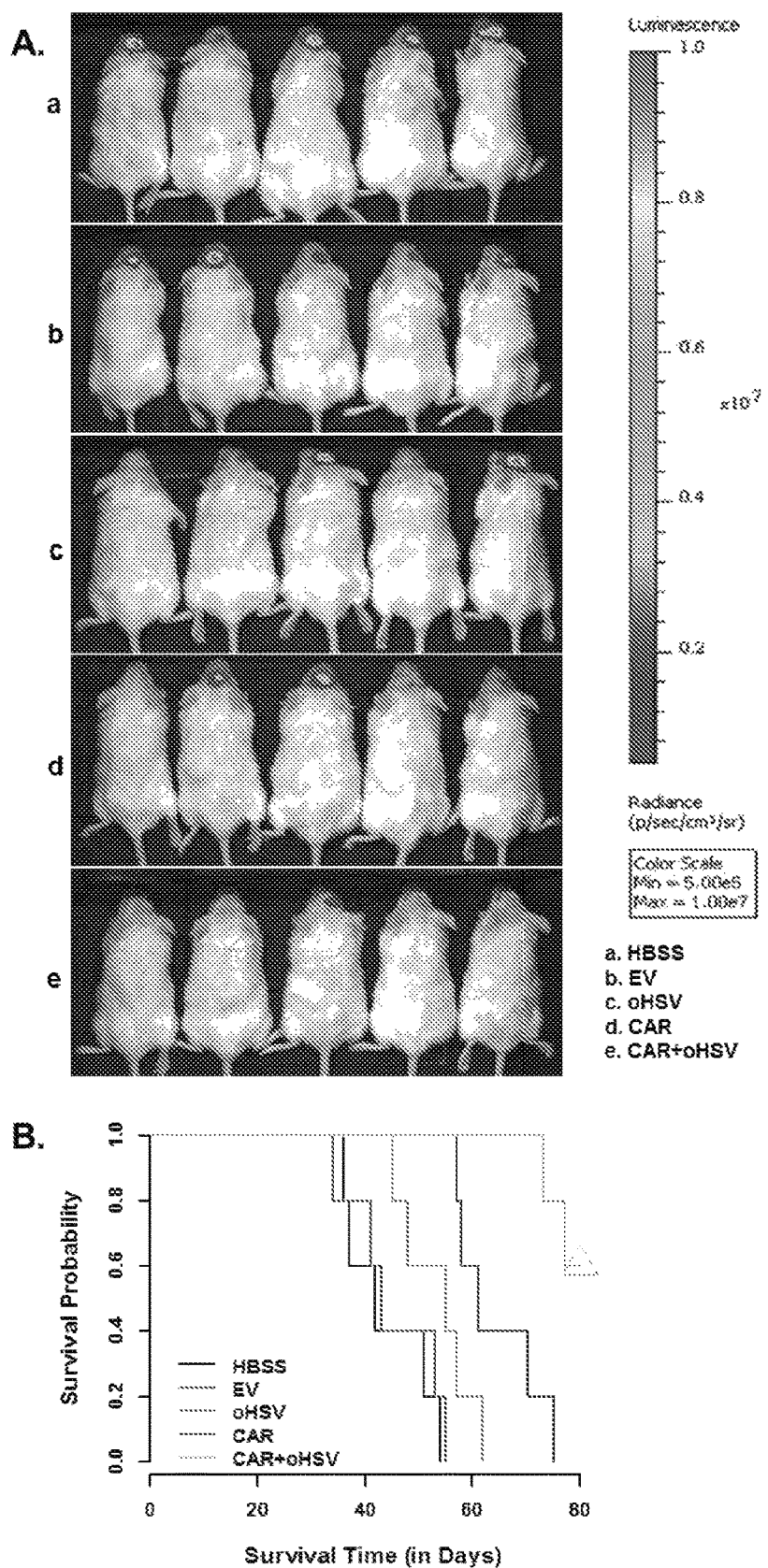
Figure 22:
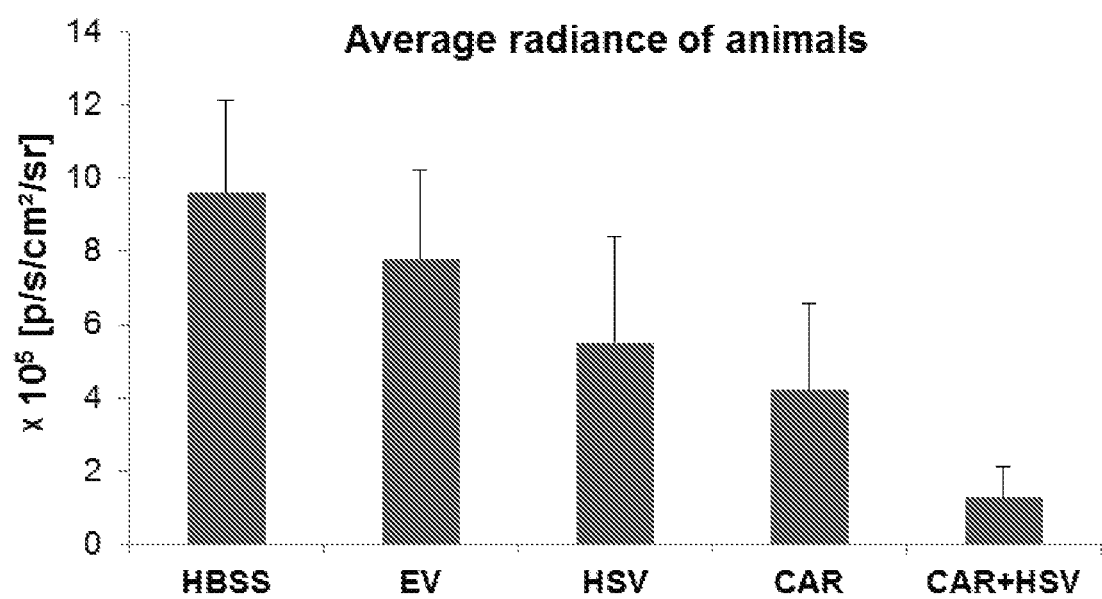
FIG. 22 shows quantification of emitted photons from intracranial xenograft GB tumors treated with vehicle, NK-92 cells, oHSV, EGFR-CAR NK-92 cells, and the combination of oHSV and EGFR-CAR NK-92 cells.

EGFR-CAR NK-92 Cells Combined with oHSV-1 Lead to More Efficient Killing of MDA-MB-231 Tumor Cells in an Intracranial Model To further support the potential therapeutic application of EGFR-CAR NK-92 cells, oHSV-1 alone, or the combination of both, Applicants examined their antitumor activity in vivo. Applicants established an intracranial model of breast cancer by implanting MDA-MB-231-CBRluc-EGFP cells into the brains of NSG mice. The expression of beetle red luciferase in the cells enabled us to monitor tumor growth via in vivo bioluminescence imaging. To minimize potential systemic toxicity, Applicants injected the non-irradiated EGFR-CAR NK-92 cells or oHSV-1 intratumorally at day 10 post-tumor cell implantation and oHSV-1 at day 15 for the group of EGFR-CAR NK-92 combined with oHSV-1. As shown in FIG. 17A and FIG. 22, mice that received either EGFR-CAR NK-92, oHSV-1, or their combination had significantly reduced tumor growth compared to those injected with mock-transduced NK-92-EV or vehicle (HBSS). Importantly, the reduction in tumor growth was more obvious in mice treated with EGFR-CAR NK-92 combined with oHSV-1 than in those treated with EGFR-CAR NK-92 alone or oHSV-1 alone. In agreement with these data, the mice treated with EGFR-CAR NK-92 plus oHSV-1 survived significantly longer than those treated with oHSV-1 alone (P<0.01), mock-transduced NK-92 (P<0.001), or HBSS (P<0.001), while the difference between the group of EGFR-CAR NK-92 plus oHSV-1 and EGFR-CAR NK-92 alone showed the same trend and was at the border of the significance threshold (P=0.0757). The median survival time of the five groups for EGFR-CAR NK-92 combined with oHSV-1, EGFR-CAR NK-92, oHSV-1, NK-92-EV and HBSS were 80, 61, 55, 43, and 42 days, respectively (FIG. 17B).

Discussion

These data demonstrate that intratumoral administration of EGFR-CAR NK-92 cells, oHSV-1, or the combination of both into mice pre-inoculated with MDA-MB-231 cells led to antitumor efficacy and their combination resulted in more efficient suppression of tumor growth and significantly longer survival of tumor-bearing mice.

Applicants believe this combination is an effective approach to target cancer. Not to be bound by theory, Applicants suspect the target of this combination approach are cancer stem cells (CSCs), a cell population responsible for relapse, treatment resistance, and metastasis in most if not all cancers. Further, Applicants posit that the disclosed approach may accommodate heterogeneous tumor populations.

That is, (considering the example of breast cancer disclosed herein above) EGFR-expressing cells are targeted by EGFR-CAR NK cells, but oHSV-1 also can kill EGFR-negative tumor cells. Breast cancer is heterogeneous for EGFR, PR, and HER2 expression. Although the breast cancer cell lines used in our experiments express wild-type EGFR, each expresses this to a different degree. Meanwhile, they have different gene expression profiling [MDA-MB-231 and MDA-MB-468: ER−, PR−, HER2− (triple negative); MCF-7: ER+, PR+/−, HER2−] and distinct biological behaviors. Triple-negative breast cancer (TNBC) is associated with an aggressive natural history as well as an increased susceptibility to metastasis Patients with TNBC lack the "traditional" therapeutic targets and have a poorer prognosis than other types of breast cancer. In fact, median survival for TNBC is only 4.9 months. The combinational approach described in this above should target BCBMs of both non-TNBC and TNBC, as oHSV is effective for the general BCBM population, while EGFR-CAR NK cells are more effective in targeting the EGFR+ populations. Such conclusions are further generalizable to essentially all type of cancers.

These data further showed that EGFR-CAR NK-92 cells can quickly target and attack breast cancer cells while oHSV-1 can slowly but constantly infect and destroy the cancer cells. EGFR-CAR NK-92 cells can usually recognize and attack target cells in several hours, but they can survive only several days because they have to be irradiated as the cell line was originally established from a patient with non-Hodgkin's lymphoma. An irradiation dose of 1000 cGy has been optimized to suppress proliferation osf NK-92 cells while maintaining full cytotoxic activity up to 48 hours post irradiation On the contrary, it may take about 4 days for oHSV to enter into target cells, replicate, and destroy the tumor cells, even though its effects can last for a long time. In addition, CAR-modified NK cells may destroy the tumor tissue structure and decrease the connection between tumor cells, increase the permeability of cancer cell membranes, and therefore enhance virus distribution and replication in cancer cells when combined with oHSV-1.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A chimeric antigen receptor (CAR) comprising: (a) an antigen binding domain of an anti-Epidermal Growth Factor Receptor (anti-EGFR) antibody that recognizes both wild type Epidermal Growth Factor Receptor (wtEGFR) and Epidermal Growth Factor Receptor variant III mutant (EGFRvIII), wherein the antigen binding domain comprises the three complementarity determining regions (CDRs) of an anti-EGFR heavy chain (HC) variable region of:

(SEQ ID NO: 24)
Q V Q L Q Q S G S E M A R P G A S V K L P C K A S

G D T F T S Y W M H W V K Q R H G H G P E W I G N

I Y P G S G G T N Y A E K F K N K V T L T V D R S

S R T V Y M H L S R L T S E D S A V Y Y C T R S G

G P Y F F D Y W G Q G T T L T V S S;

and the CDRs of an anti-EGFR light chain (LC) variable region of:

(SEQ ID NO: 26)
D I L M T Q S P L S L P V S L G D Q A S I S C R S

S Q N I V H N N G I T Y L E W Y L Q R P G Q S P K

L L I Y K V S D R F S G V P D R F S G S G S G T D

F T L K I S R V E A E D L G I Y Y C F Q G S H I P

P T F G G G T K L E I K R A A;

(b) a hinge domain polypeptide; (c) a costimulatory molecule or polypeptide; and (d) a CD3 zeta signaling domain.

2. The CAR of claim 1, wherein the costimulatory molecule comprises a molecule or polypeptide selected from the group of: a 4-1BB costimulatory signaling region, a CD28 costimulatory molecule, OX40, ICOS and CD27.

3. The CAR of claim 1, wherein the antigen binding domain of the anti-EGFR antibody comprises an anti-EGFR heavy chain (HC) variable region comprising the amino acid sequence of SEQ ID NO: 24 or an equivalent thereof having at least 80% identity to SEQ ID NO: 24; and an anti-EGFR light chain (LC) variable region comprising the amino acid sequence of SEQ ID NO: 26 or an equivalent thereof having at least 80% identity to SEQ ID NO: 26.

4. The CAR of claim 3, further comprising a linker polypeptide located between the anti-EGFR HC variable region and the anti-EGFR LC variable region.

5. The CAR of claim 4, wherein the linker polypeptide comprises SEQ ID NO:22 (GGGGSGGGGSGGGG).

6. The CAR of claim 1, further comprising a signal polypeptide to the amino terminus of the antigen binding domain.

7. The CAR of claim 1, wherein the hinge polypeptide is encoded by a polynucleotide that comprises SEQ ID NO:1 (CTCGAGCCCAAATCTTGTGACAAAACTCACACATGCCCACCGTGCCCG).

8. The CAR of claim 2, wherein the CD28 costimulatory molecule comprises a CD28 transmembrane domain and a CD28 intracellular domain.

9. The CAR of claim 1, further comprising a detectable marker or a purification marker attached to the CAR.

10. An isolated nucleic acid encoding the CAR of claim 1.

11. A vector comprising the isolated nucleic acid sequence of claim 10, that is optionally a plasmid or a viral vector.

12. The vector of claim 11, wherein the viral vector is selected from a group consisting of a retroviral vector, a lentiviral vector, an adenoviral vector, and an adeno-associated viral vector.

13. The vector of claim 11, further comprising a detectable label or a purification marker, wherein the detectable label optionally is not a naturally occurring polynucleotide.

14. An isolated cell comprising the CAR of claim 1, that is optionally a prokaryotic cell or a eukaryotic cell.

15. An isolated cell comprising the isolated nucleic acid of claim 10.

16. An isolated cell comprising the vector of claim 11.

17. The isolated cell of claim 15, wherein the cell is a prokaryotic or a eukaryotic cell.

18. The isolated cell of claim 16, wherein the cell is a prokaryotic or a eukaryotic cell.

19. The isolated cell of claim 17, wherein the eukaryotic cell is selected from an animal cell, a mammalian cell, a bovine cell, a feline cell, a canine cell, a murine cell, an equine cell or a human cell.

20. The isolated cell of claim 18, wherein the eukaryotic cell is selected from an animal cell, a mammalian cell, a bovine cell, a feline cell, a canine cell, a murine cell, an equine cell or a human cell.

21. The isolated cell of claim 14, wherein the cell is selected from the group of a T-cell, a natural killer (NK) cell, a natural killer T-cell, a stem cell, or a leukocyte derived from hematopoietic stem cells (HSC).

22. The isolated cell of claim 19, wherein the cell is selected from the group of a T-cell, a natural killer (NK) cell, a natural killer T-cell, a stem cell, or a leukocyte derived from hematopoietic stem cells (HSC).

23. The isolated cell of claim 20, wherein the cell is selected from the group of a T-cell, a natural killer (NK) cell, a natural killer T-cell, a stem cell, or a leukocyte derived from hematopoietic stem cells (HSC).

24. An isolated complex comprising the CAR of claim 1 and a wtEGFR protein or a fragment thereof or an EGFRvIII protein or a fragment thereof.

25. An isolated complex comprising the CAR of claim 1 and a cell expressing a wtEGFR or an EGFRvIII.

26. A composition comprising a carrier and one or more of the CAR of claim 1, an isolated cell comprising the CAR, an isolated nucleic acid encoding the CAR, or a vector comprising the isolated nucleic acid.

27. The composition of claim 26, wherein the carrier is a pharmaceutically acceptable carrier or a solid support.

28. A kit for treating cancer, comprising the CAR of claim 1 and instructions for use, optionally with an oncolytic herpes virus.

29. The isolated cell of claim 14, wherein the cell is a natural killer (NK) cell.

30. The isolated cell of claim 19, wherein the cell is a natural killer (NK) cell.

31. The isolated cell of claim 20, wherein the cell is a natural killer (NK) cell.

32. The CAR of claim 1, wherein the antigen binding domain of the anti-EGFR antibody comprises an anti-EGFR heavy chain (HC) variable region that consists of the amino acid sequence of SEQ ID NO: 24 or an equivalent thereof and an anti-EGFR light chain (LC) variable region that consists of the amino acid sequence of SEQ ID NO: 26, or an equivalent of thereof.

33. The CAR of claim 32, further comprising a linker polypeptide located between the HC variable region and the LC variable region.

\* \* \* \* \*

UNITED STATES PATENT AND TRADEMARK OFFICE
CERTIFICATE OF CORRECTION

PATENT NO. : 11,045,543 B2
APPLICATION NO. : 15/564166
DATED : June 29, 2021
INVENTOR(S) : Yu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 52 days.

In the Claims

Column 83, Claim 1, Line 36 should read:
and the three CDRs of an anti-EGFR light chain (LC) variable Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 31

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctcgagccca aatcttgtga caaaactcac acatgcccac cgtgcccg                    48

<210> SEQ ID NO 2
<211> LENGTH: 81
<212> TYPE: DNA
<213> ORGANISM: Unknown
<220> FEATURE:
<223> OTHER INFORMATION: Description of Unknown:
      CD28 transmembrane region sequence

<400> SEQUENCE: 2
ttttgggtgc tggtggtggt tggtggagtc ctggcttgct atagcttgct agtaacagtg       60
gcctttatta ttttctgggt g                                                81

<210> SEQ ID NO 3
<211> LENGTH: 126
<212> TYPE: DNA
<213> ORGANISM: Unknown
<220> FEATURE:
<223> OTHER INFORMATION: Description of Unknown:
      4-1BB co-stimulatory signaling region sequence
```

<400> SEQUENCE: 3

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 4
<211> LENGTH: 123
<212> TYPE: DNA
<213> ORGANISM: Unknown
<220> FEATURE:
<223> OTHER INFORMATION: Description of Unknown:
      CD28 co-stimulatory signaling region sequence

<400> SEQUENCE: 4

```
aggagtaaga ggagcaggct cctgcacagt gactacatga acatgactcc cgccgcccc    60 gggcccaccc gcaagcatta ccagccctat gccccaccac gcgacttcgc agcctatcgc   120
tcc                                                                 123
```

<210> SEQ ID NO 5
<211> LENGTH: 339
<212> TYPE: DNA
<213> ORGANISM: Unknown
<220> FEATURE:
<223> OTHER INFORMATION: Description of Unknown:
      CD3 zeta signaling region sequence

<400> SEQUENCE: 5

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240 cggagggca aggggcacga tggcctttac cagggtctca gtacagccac caaggacacc   300
tacgacgccc ttcacatgca ggccctgccc cctcgctaa                          339
```

<210> SEQ ID NO 6
<211> LENGTH: 1210
<212> TYPE: PRT
<213> ORGANISM: Homo sapiens

<400> SEQUENCE: 6

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
```

```
            115                 120                 125
Lys Thr Gly Leu Lys Glu Leu Pro Met Arg Asn Leu Gln Glu Ile Leu
        130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
530                 535                 540
```

```
Glu Pro Arg Glu Phe Val Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
                610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
                690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
                770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
                850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
945                 950                 955                 960
```

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
        980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 7
<211> LENGTH: 705
<212> TYPE: PRT
<213> ORGANISM: Homo sapiens

<400> SEQUENCE: 7

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

```
Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525
```

```
Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Ser Cys
690                 695                 700

His
705

<210> SEQ ID NO 8
<211> LENGTH: 1200
<212> TYPE: PRT
<213> ORGANISM: Homo sapiens

<400> SEQUENCE: 8

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190
```

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

```
Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
        660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
    915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Leu Met
            980                 985                 990

Asp Glu Glu Asp Met Asp Asp Val  Val Asp Ala Asp Glu  Tyr Leu Ile
    995                 1000                 1005

Pro Gln  Gln Gly Phe Phe Ser  Ser Pro Ser Thr Ser  Arg Thr Pro
    1010                 1015                 1020

Leu Leu Ser Ser Leu Ser Ala  Thr Ser Asn Asn Ser  Thr Val Ala
```

```
              1025                1030                1035
Cys Ile Asp Arg Asn Gly Leu Gln Ser Cys Pro Ile Lys Glu Asp
        1040                1045                1050

Ser Phe Leu Gln Arg Tyr Ser Ser Asp Pro Thr Gly Ala Leu Thr
        1055                1060                1065

Glu Asp Ser Ile Asp Asp Thr Phe Leu Pro Val Pro Glu Tyr Ile
        1070                1075                1080

Asn Gln Ser Val Pro Lys Arg Pro Ala Gly Ser Val Gln Asn Pro
        1085                1090                1095

Val Tyr His Asn Gln Pro Leu Asn Pro Ala Pro Ser Arg Asp Pro
        1100                1105                1110

His Tyr Gln Asp Pro His Ser Thr Ala Val Gly Asn Pro Glu Tyr
        1115                1120                1125

Leu Asn Thr Val Gln Pro Thr Cys Val Asn Ser Thr Phe Asp Ser
        1130                1135                1140

Pro Ala His Trp Ala Gln Lys Gly Ser His Gln Ile Ser Leu Asp
        1145                1150                1155

Asn Pro Asp Tyr Gln Gln Asp Phe Phe Pro Lys Glu Ala Lys Pro
        1160                1165                1170

Asn Gly Ile Phe Lys Gly Ser Thr Ala Glu Asn Ala Glu Tyr Leu
        1175                1180                1185

Arg Val Ala Pro Gln Ser Ser Glu Phe Ile Gly Ala
        1190                1195                1200

<210> SEQ ID NO 9
<211> LENGTH: 7
<212> TYPE: PRT
<213> ORGANISM: Homo sapiens

<400> SEQUENCE: 9

Glu Leu Arg Glu Ala Thr Ser
1               5

<210> SEQ ID NO 10
<211> LENGTH: 6
<212> TYPE: PRT
<213> ORGANISM: Homo sapiens

<400> SEQUENCE: 10

Glu Leu Arg Glu Ala Thr
1               5

<210> SEQ ID NO 11
<211> LENGTH: 51
<212> TYPE: PRT
<213> ORGANISM: Homo sapiens

<400> SEQUENCE: 11

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50

<210> SEQ ID NO 12
```

<211> LENGTH: 49
<212> TYPE: PRT
<213> ORGANISM: Mus musculus

<400> SEQUENCE: 12

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 13
<211> LENGTH: 51
<212> TYPE: PRT
<213> ORGANISM: Felis sp.

<400> SEQUENCE: 13

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
        50

<210> SEQ ID NO 14
<211> LENGTH: 21
<212> TYPE: PRT
<213> ORGANISM: Homo sapiens

<400> SEQUENCE: 14

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 15
<211> LENGTH: 21
<212> TYPE: PRT
<213> ORGANISM: Mus musculus

<400> SEQUENCE: 15

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 16
<211> LENGTH: 21
<212> TYPE: PRT
<213> ORGANISM: Rattus norvegicus

<400> SEQUENCE: 16

Ile Trp Ala Pro Leu Ala Gly Ile Cys Ala Val Leu Leu Leu Ser Leu
1               5                   10                  15

Val Ile Thr Leu Ile
            20

<210> SEQ ID NO 17
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 18
<211> LENGTH: 220
<212> TYPE: PRT
<213> ORGANISM: Unknown
<220> FEATURE:
<223> OTHER INFORMATION: Description of Unknown:
      CD28 polypeptide sequence

<400> SEQUENCE: 18

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 19
<211> LENGTH: 105
<212> TYPE: DNA
<213> ORGANISM: Unknown
<220> FEATURE:

<223> OTHER INFORMATION: Description of Unknown:
      ICOS costimulatory signaling region sequence

<400> SEQUENCE: 19
acaaaaaaga agtattcatc cagtgtgcac gaccctaacg gtgaatacat gttcatgaga    60
gcagtgaaca cagccaaaaa atccagactc acagatgtga cccta                  105

<210> SEQ ID NO 20
<211> LENGTH: 108
<212> TYPE: DNA
<213> ORGANISM: Unknown
<220> FEATURE:
<223> OTHER INFORMATION: Description of Unknown:
      OX40 costimulatory signaling region sequence

<400> SEQUENCE: 20
agggaccaga ggctgccccc cgatgcccac aagccccctg ggggaggcag tttccggacc    60
cccatccaag aggagcaggc cgacgcccac tccaccctgg ccaagatc               108

<210> SEQ ID NO 21
<211> LENGTH: 112
<212> TYPE: PRT
<213> ORGANISM: Unknown
<220> FEATURE:
<223> OTHER INFORMATION: Description of Unknown:
      CD3 zeta signaling domain sequence

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser Gly Gly Gly Gly Ser Gly Gly Gly Gly
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Phe Gly Ala Gly Leu Val Leu Gly Gly Gln Phe Met
1               5                   10

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Gln Ser Gly Ser Glu Met Ala Arg Pro Gly Ala
1               5                   10                  15

Ser Val Lys Leu Pro Cys Lys Ala Ser Gly Asp Thr Phe Thr Ser Tyr
            20                  25                  30

Trp Met His Trp Val Lys Gln Arg His Gly His Gly Pro Glu Trp Ile
        35                  40                  45

Gly Asn Ile Tyr Pro Gly Ser Gly Gly Thr Asn Tyr Ala Glu Lys Phe
    50                  55                  60

Lys Asn Lys Val Thr Leu Thr Val Asp Arg Ser Ser Arg Thr Val Tyr
65                  70                  75                  80

Met His Leu Ser Arg Leu Thr Ser Glu Asp Ser Ala Val Tyr Tyr Cys
                85                  90                  95

Thr Arg Ser Gly Gly Pro Tyr Phe Phe Asp Tyr Trp Gly Gln Gly Thr
            100                 105                 110

Thr Leu Thr Val Ser Ser
        115

<210> SEQ ID NO 25
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacattctaa tgacccaatc tccactctcc ctgcctgtca gtcttggaga tcaagcctcc      60
tacctgcaaa ggccaggcca gtctccaaag ctcctgatct acaaagtttc cgaccgattt     120
tacctgcaaa ggccaggcca gtctccaaag ctcctgatct acaaagtttc cgaccgattt     180
tctggggtcc cagacaggtt cagtggcagt ggatcaggga cagatttcac actcaagatc     240
agcagagtag aggctgagga tctgggaatt tattactgct ttcaaggttc acatattcct     300
cccacgttcg agggggggac caagctggaa atcaaacgtg cggcc                    345

<210> SEQ ID NO 26
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Leu Met Thr Gln Ser Pro Leu Ser Leu Pro Val Ser Leu Gly
1               5                   10                  15

Asp Gln Ala Ser Ile Ser Cys Arg Ser Ser Gln Asn Ile Val His Asn
            20                  25                  30

```
Asn Gly Ile Thr Tyr Leu Glu Trp Tyr Leu Gln Arg Pro Gly Gln Ser
         35                  40                  45

Pro Lys Leu Leu Ile Tyr Lys Val Ser Asp Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Phe Gln Gly
                 85                  90                  95

Ser His Ile Pro Pro Thr Phe Gly Gly Gly Thr Lys Leu Glu Ile Lys
            100                 105                 110

Arg Ala Ala
        115

<210> SEQ ID NO 27
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtccagc tgcagcagtc tgggtctgag atggcgaggc ctggagcttc agtgaagctg     60
ccctgcaagg cttctggcga cacattcacc agttactgga tgcactgggt gaagcagagg    120
catggacatg ccctgagtg atcggaaat atttatccag gtagtggtgg tactaactac     180
gctgagaagt tcaagaacaa ggtcactctg actgtagaca ggtcctcccg cacagtctac    240
atgcacctca gcaggctgac atctgaggac tctgcggtct attattgtac aagatcgggg    300
ggtccctact tctttgacta ctggggccaa ggcaccactc tcacagtctc ctcc          354

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgactccgtc cagtattgat cg                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcccttcgca cttcttacac tt                                              22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
```

```
aggtcactct gactgtagac a                                      21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttcatgtag tcactgtgca g                                      21
```